United States Patent
Pace et al.

(10) Patent No.: US 11,051,725 B2
(45) Date of Patent: Jul. 6, 2021

(54) ANALYTE SENSOR DEVICES, CONNECTIONS, AND METHODS

(71) Applicant: ABBOTT DIABETES CARE INC., Alameda, CA (US)

(72) Inventors: Louis Pace, San Carlos, CA (US); Peter G. Robinson, Alamo, CA (US); Udo Hoss, Castro Valley, CA (US); Samuel Mason Curry, San Francisco, CA (US); Phillip William Carter, Oakland, CA (US); Vincent Michael DiPalma, Oakland, CA (US); Amit Mhatre, Sunnyvale, CA (US); Jennifer Olson, San Francisco, CA (US); Manuel Luis Miguel Donnay, San Francisco, CA (US); Marc Barry Taub, Mountain View, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 16/951,656

(22) Filed: Nov. 18, 2020

(65) Prior Publication Data

US 2021/0068722 A1     Mar. 11, 2021

Related U.S. Application Data

(63) Continuation of application No. 15/908,616, filed on Feb. 28, 2018, which is a continuation of application
(Continued)

(51) Int. Cl.
*A61B 5/00*     (2006.01)
*A61B 5/145*     (2006.01)
(Continued)

(52) U.S. Cl.
CPC ........ *A61B 5/14503* (2013.01); *A61B 5/0004* (2013.01); *A61B 5/145* (2013.01);
(Continued)

(58) Field of Classification Search
CPC ... A61B 5/14503; A61B 5/145; A61B 5/0004; A61B 5/1451; A61B 5/14532;
(Continued)

(56) References Cited

U.S. PATENT DOCUMENTS

| 3,132,123 A | 5/1964 | Harris, Jr. et al. |
| 3,260,656 A | 7/1966 | Ross, Jr. |

(Continued)

FOREIGN PATENT DOCUMENTS

| CA | 2291105 | 12/1998 |
| CN | 1202872 | 5/2005 |

(Continued)

OTHER PUBLICATIONS

Alcock, S. J., et al., "Continuous Analyte Monitoring to Aid Clinical Practice", IEEE Engineering in Medicine and Biology Magazine, 1994, pp. 319-325.

(Continued)

*Primary Examiner* — Christian Jang
(74) *Attorney, Agent, or Firm* — One LLP

(57) ABSTRACT

Devices associated with on-body analyte sensor units are disclosed. These devices include any of packaging and/or loading systems, applicators and elements of the on-body sensor units themselves. Also, various approaches to connecting electrochemical analyte sensors to and/or within associated on-body analyte sensor units are disclosed. The connector approaches variously involve the use of unique sensor and ancillary element arrangements to facilitate
(Continued)

assembly of separate electronics assemblies and sensor elements that are kept apart until the end user brings them together.

27 Claims, 64 Drawing Sheets

Related U.S. Application Data

No. 15/610,334, filed on May 31, 2017, now Pat. No. 9,931,066, which is a continuation of application No. 15/193,499, filed on Jun. 27, 2016, now Pat. No. 9,693,713, which is a continuation of application No. 13/710,460, filed on Dec. 11, 2012, now Pat. No. 9,402,570.

(60) Provisional application No. 61/569,287, filed on Dec. 11, 2011.

(51) Int. Cl.
  *A61B 5/15* (2006.01)
  *A61B 5/151* (2006.01)
  *A61B 5/157* (2006.01)
  *H04L 29/08* (2006.01)
  *A61B 50/30* (2016.01)

(52) U.S. Cl.
  CPC .......... *A61B 5/1411* (2013.01); *A61B 5/1451* (2013.01); *A61B 5/14532* (2013.01); *A61B 5/157* (2013.01); *A61B 5/150022* (2013.01); *A61B 5/15087* (2013.01); *A61B 5/15105* (2013.01); *A61B 5/15144* (2013.01); *A61B 5/150305* (2013.01); *A61B 5/150335* (2013.01); *A61B 5/150358* (2013.01); *A61B 5/150389* (2013.01); *A61B 5/150503* (2013.01); *A61B 5/150748* (2013.01); *A61B 5/150877* (2013.01); *A61B 5/6849* (2013.01); *A61B 50/3001* (2016.02); *H04L 67/12* (2013.01); *A61B 2560/0406* (2013.01); *A61B 2560/0443* (2013.01); *A61B 2560/063* (2013.01); *A61B 2562/16* (2013.01); *A61B 2562/242* (2013.01)

(58) Field of Classification Search
  CPC ........ A61B 2562/16; A61B 2560/0406; A61B 2560/0443
  See application file for complete search history.

(56) References Cited

U.S. PATENT DOCUMENTS

| | | |
|---|---|---|
| 3,522,807 A | 8/1970 | Millenbach |
| 3,581,062 A | 5/1971 | Aston |
| 3,653,841 A | 4/1972 | Klein |
| 3,670,727 A | 6/1972 | Reiterman |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,949,388 A | 4/1976 | Fuller |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danniger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,245,634 A | 1/1981 | Albisser et al. |
| 4,247,297 A | 1/1981 | Berti et al. |
| 4,294,258 A | 10/1981 | Bernard |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,353,888 A | 10/1982 | Sefton |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,450,842 A | 5/1984 | Zick et al. |
| 4,458,686 A | 7/1984 | Clark, Jr. |
| 4,461,691 A | 7/1984 | Frank |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,619,754 A | 10/1986 | Niki et al. |
| 4,619,793 A | 10/1986 | Lee |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardien |
| 4,637,403 A | 1/1987 | Garcia et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,663,824 A | 5/1987 | Kenmochi |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,466 A | 8/1987 | Rau |
| 4,698,057 A | 10/1987 | Joishy |
| 4,703,756 A | 11/1987 | Gough et al. |
| 4,711,245 A | 12/1987 | Higgins et al. |

(56) References Cited

U.S. PATENT DOCUMENTS

| | | |
|---|---|---|
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Gough |
| 4,781,683 A | 11/1988 | Wozniak et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,848,351 A | 7/1989 | Finch |
| 4,854,322 A | 8/1989 | Ash et al. |
| 4,871,351 A | 10/1989 | Feingold |
| 4,871,440 A | 10/1989 | Nagata et al. |
| 4,874,500 A | 10/1989 | Madou et al. |
| 4,890,622 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,921,199 A | 5/1990 | Villavecs |
| 4,923,586 A | 5/1990 | Katayama et al. |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guibeau et al. |
| 4,938,860 A | 7/1990 | Wogoman |
| 4,944,299 A | 7/1990 | Silvian |
| 4,950,378 A | 8/1990 | Nagara |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Curry |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,055,171 A | 10/1991 | Peck |
| 5,058,592 A | 10/1991 | Whisler |
| 5,070,535 A | 12/1991 | Hochmair et al. |
| 5,082,550 A | 1/1992 | Rishpon et al. |
| 5,082,786 A | 1/1992 | Nakamoto |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,126,034 A | 6/1992 | Carter et al. |
| 5,133,856 A | 7/1992 | Yamaguchi et al. |
| 5,135,003 A | 8/1992 | Souma |
| 5,140,985 A | 8/1992 | Schroeder et al. |
| 5,141,868 A | 8/1992 | Shanks et al. |
| 5,161,532 A | 11/1992 | Joseph |
| 5,165,407 A | 11/1992 | Wilson et al. |
| 5,174,291 A | 12/1992 | Schoonen et al. |
| 5,190,041 A | 3/1993 | Palti |
| 5,192,416 A | 3/1993 | Wang et al. |
| 5,198,367 A | 3/1993 | Aizawa et al. |
| 5,202,261 A | 4/1993 | Musho et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,229,282 A | 7/1993 | Yoshioka et al. |
| 5,234,835 A | 8/1993 | Nestor et al. |
| 5,238,729 A | 8/1993 | Debe |
| 5,246,867 A | 9/1993 | Lakowicz et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,271,815 A | 12/1993 | Wong |
| 5,279,294 A | 1/1994 | Anderson |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,293,546 A | 3/1994 | Tadros et al. |
| 5,293,877 A | 3/1994 | O'Hara et al. |
| 5,299,571 A | 4/1994 | Mastrototaro |
| 5,320,098 A | 6/1994 | Davidson |
| 5,320,725 A | 6/1994 | Gregg et al. |
| 5,322,063 A | 6/1994 | Allen et al. |
| 5,337,747 A | 8/1994 | Neftei |
| 5,340,722 A | 8/1994 | Wolfbeis et al. |
| 5,342,789 A | 8/1994 | Chick et al. |
| 5,352,348 A | 10/1994 | Young et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,387,327 A | 2/1995 | Khan |
| 5,390,671 A | 2/1995 | Lord et al. |
| 5,391,250 A | 2/1995 | Cheney, II et al. |
| 5,395,504 A | 3/1995 | Saurer et al. |
| 5,400,782 A | 3/1995 | Beaubiah |
| 5,408,999 A | 4/1995 | Singh et al. |
| 5,411,647 A | 5/1995 | Johnson et al. |
| 5,425,361 A | 6/1995 | Fenzlein et al. |
| 5,431,160 A | 7/1995 | Wilkins |
| 5,431,921 A | 7/1995 | Thombre |
| 5,437,999 A | 8/1995 | Dieboid et al. |
| 5,462,645 A | 10/1995 | Albery et al. |
| 5,469,846 A | 11/1995 | Khan |
| 5,472,317 A | 12/1995 | Field et al. |

(56) References Cited

U.S. PATENT DOCUMENTS

| | | |
|---|---|---|
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,527,288 A | 6/1996 | Gross et al. |
| 5,531,878 A | 7/1996 | Vadgama et al. |
| 5,545,191 A | 8/1996 | Mann et al. |
| 5,549,368 A | 8/1996 | Shields |
| 5,551,427 A | 9/1996 | Altman |
| 5,560,357 A | 10/1996 | Faupei et al. |
| 5,562,713 A | 10/1996 | Silvian |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,575,563 A | 11/1996 | Chiu et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halli et al. |
| 5,589,326 A | 12/1996 | Deng et al. |
| 5,593,852 A | 1/1997 | Heller et al. |
| 5,596,150 A | 1/1997 | Arndt et al. |
| 5,601,435 A | 2/1997 | Quy |
| 5,609,575 A | 3/1997 | Larson et al. |
| 5,613,978 A | 3/1997 | Harding |
| 5,617,851 A | 4/1997 | Lipkovker |
| 5,628,310 A | 5/1997 | Rao et al. |
| 5,628,890 A | 5/1997 | Carter et al. |
| 5,632,557 A | 5/1997 | Simons |
| 5,640,954 A | 6/1997 | Pfeiffer et al. |
| 5,651,869 A | 7/1997 | Yoshioka et al. |
| 5,653,239 A | 8/1997 | Pompei et al. |
| 5,660,163 A | 8/1997 | Schulman et al. |
| 5,665,071 A | 9/1997 | Wyrick |
| 5,665,222 A | 9/1997 | Heller et al. |
| 5,670,031 A | 9/1997 | Hintsche et al. |
| 5,680,858 A | 10/1997 | Hansen et al. |
| 5,682,233 A | 10/1997 | Brinda |
| 5,695,623 A | 12/1997 | Michel et al. |
| 5,708,247 A | 1/1998 | McAleer et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,733,044 A | 3/1998 | Rose et al. |
| 5,735,285 A | 4/1998 | Albert et al. |
| 5,741,211 A | 4/1998 | Renirie et al. |
| 5,749,656 A | 5/1998 | Boehm et al. |
| 5,766,131 A | 6/1998 | Kondo et al. |
| 5,771,001 A | 6/1998 | Cobb |
| 5,772,586 A | 6/1998 | Heinonen et al. |
| 5,779,665 A | 7/1998 | Mastrototaro et al. |
| 5,791,344 A | 8/1998 | Schulman et al. |
| 5,800,420 A | 9/1998 | Gross et al. |
| 5,807,375 A | 9/1998 | Gross et al. |
| 5,814,020 A | 9/1998 | Gross |
| 5,820,551 A | 10/1998 | Hill et al. |
| 5,820,622 A | 10/1998 | Gross et al. |
| 5,822,715 A | 10/1998 | Worthington et al. |
| 5,827,184 A | 10/1998 | Netherty et al. |
| 5,840,020 A | 11/1998 | Heinonen et al. |
| 5,842,983 A | 12/1998 | Abel et al. |
| 5,851,197 A | 12/1998 | Marano et al. |
| 5,858,001 A | 1/1999 | Tsals et al. |
| 5,865,804 A | 2/1999 | Bachynsky |
| 5,885,211 A | 3/1999 | Eppstein et al. |
| 5,899,855 A | 5/1999 | Brown |
| 5,924,979 A | 7/1999 | Sedlow et al. |
| 5,925,021 A | 7/1999 | Castellano et al. |
| 5,931,814 A | 8/1999 | Alex et al. |
| 5,948,006 A | 9/1999 | Mann |
| 5,951,521 A | 9/1999 | Mastrototaro et al. |
| 5,954,643 A | 9/1999 | Van Antwerp |
| 5,954,685 A | 9/1999 | Tierny |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,987,353 A | 11/1999 | Khatchatrian et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,017,335 A | 1/2000 | Burnham |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,049,727 A | 4/2000 | Crothall |
| 6,056,718 A | 5/2000 | Funderburk et al. |
| 6,068,399 A | 5/2000 | Tseng |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A | 7/2000 | Funderburk et al. |
| 6,102,896 A | 8/2000 | Roser |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,129,666 A | 10/2000 | DeLuca et al. |
| 6,134,461 A | 10/2000 | Say et al. |
| 6,143,164 A | 11/2000 | Heller et al. |
| 6,159,147 A | 12/2000 | Lichter et al. |
| 6,162,611 A | 12/2000 | Heller et al. |
| 6,175,752 B1 | 1/2001 | Say et al. |
| 6,186,982 B1 | 2/2001 | Gross et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,331,244 B1 | 12/2001 | Lewis et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,368,141 B1 | 4/2002 | Van Antwerp et al. |
| 6,368,274 B1 | 4/2002 | Van Antwerp et al. |
| 6,377,828 B1 | 4/2002 | Chaiken et al. |
| 6,379,301 B1 | 4/2002 | Worthington et al. |
| 6,409,740 B1 | 6/2002 | Kuhr et al. |
| 6,413,393 B1 | 7/2002 | Van Antwerp et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,437,679 B1 | 8/2002 | Roques |
| 6,440,068 B1 | 8/2002 | Brown et al. |
| 6,445,374 B2 | 9/2002 | Albert et al. |
| 6,478,736 B1 | 11/2002 | Mault |
| 6,482,176 B1 | 11/2002 | Wich |

(56) References Cited

U.S. PATENT DOCUMENTS

| | | |
|---|---|---|
| 6,484,045 B1 | 11/2002 | Holker et al. |
| 6,484,046 B1 | 11/2002 | Say et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,566 B2 | 6/2003 | Effenhauser |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,666,849 B1 | 12/2003 | Marshall et al. |
| 6,668,196 B1 | 12/2003 | Villegas et al. |
| 6,676,290 B1 | 1/2004 | Lu |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,830,551 B1 | 12/2004 | Uchigaki et al. |
| 6,837,858 B2 | 1/2005 | Cunningham et al. |
| 6,837,885 B2 | 1/2005 | Koblish et al. |
| 6,837,988 B2 | 1/2005 | Leong et al. |
| 6,849,052 B2 | 2/2005 | Uchigaki et al. |
| 6,854,882 B2 | 2/2005 | Chen |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,959,211 B2 | 10/2005 | Rule et al. |
| 6,968,294 B2 | 11/2005 | Gutta et al. |
| 6,971,274 B2 | 12/2005 | Olin |
| 6,971,999 B2 | 12/2005 | Py et al. |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,024,245 B2 | 4/2006 | Lebel et al. |
| 7,025,743 B2 | 4/2006 | Mann et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,097,637 B2 | 8/2006 | Triplett et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,340,287 B2 | 3/2008 | Mason et al. |
| 7,340,309 B2 | 3/2008 | Miazga et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,407,493 B2 | 8/2008 | Cane |
| 7,416,541 B2 | 8/2008 | Yuzhakov et al. |
| 7,424,318 B2 | 9/2008 | Brister et al. |
| 7,455,663 B2 | 11/2008 | Bikovsky |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,604,592 B2 | 10/2009 | Freeman et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,666,149 B2 | 2/2010 | Simons et al. |
| 7,682,338 B2 | 3/2010 | Griffin |
| 7,697,967 B2 | 4/2010 | Stafford |
| 7,699,807 B2 | 4/2010 | Faust et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,344 B2 | 6/2010 | Moberg et al. |
| 7,763,042 B2 | 7/2010 | Iio et al. |
| 7,822,454 B1 | 10/2010 | Alden et al. |
| 7,850,652 B2 | 12/2010 | Liniger et al. |
| 7,896,844 B2 | 3/2011 | Thalmann et al. |

(56) References Cited

U.S. PATENT DOCUMENTS

| | | |
|---|---|---|
| 7,955,297 B2 | 6/2011 | Radmer et al. |
| 7,985,203 B2 | 7/2011 | Haueter et al. |
| 8,172,805 B2 | 5/2012 | Mogensen et al. |
| 8,262,618 B2 | 9/2012 | Scheurer |
| 8,409,145 B2 | 4/2013 | Raymond et al. |
| 8,870,822 B2 | 10/2014 | Thalmann et al. |
| 8,880,138 B2 | 11/2014 | Cho |
| 9,007,781 B2 | 4/2015 | Moein et al. |
| 9,215,992 B2 | 12/2015 | Donnay et al. |
| 9,295,786 B2 | 3/2016 | Gottlieb et al. |
| 2001/0056262 A1 | 12/2001 | Cabiri et al. |
| 2002/0013538 A1 | 1/2002 | Teller |
| 2002/0019022 A1 | 2/2002 | Dunn et al. |
| 2002/0019606 A1 | 2/2002 | Lebel et al. |
| 2002/0022855 A1 | 2/2002 | Bobroff et al. |
| 2002/0023852 A1 | 2/2002 | McIvor et al. |
| 2002/0042090 A1 | 4/2002 | Heller et al. |
| 2002/0055711 A1 | 5/2002 | Lavi et al. |
| 2002/0057993 A1 | 5/2002 | Maisey et al. |
| 2002/0066764 A1 | 6/2002 | Perry et al. |
| 2002/0076966 A1 | 6/2002 | Carron et al. |
| 2002/0082487 A1 | 6/2002 | Kollias et al. |
| 2002/0103499 A1 | 8/2002 | Perez et al. |
| 2002/0106709 A1 | 8/2002 | Potts et al. |
| 2002/0119711 A1 | 8/2002 | Van Antwerp et al. |
| 2002/0124017 A1 | 9/2002 | Mault |
| 2002/0128594 A1 | 9/2002 | Das et al. |
| 2002/0130042 A1 | 9/2002 | Moerman et al. |
| 2002/0151796 A1 | 10/2002 | Koulik |
| 2002/0151816 A1 | 10/2002 | Rich et al. |
| 2002/0154050 A1 | 10/2002 | Krupp et al. |
| 2002/0161288 A1 | 10/2002 | Shin et al. |
| 2002/0165462 A1 | 11/2002 | Westbrook et al. |
| 2002/0169369 A1 | 11/2002 | Ward et al. |
| 2002/0198444 A1 | 12/2002 | Ughigaki et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0042137 A1 | 3/2003 | Mao et al. |
| 2003/0060753 A1 | 3/2003 | Starkweather et al. |
| 2003/0065308 A1 | 4/2003 | Lebel et al. |
| 2003/0069510 A1 | 4/2003 | Semler |
| 2003/0078481 A1 | 4/2003 | McIvor et al. |
| 2003/0078560 A1 | 4/2003 | Miller et al. |
| 2003/0083686 A1 | 5/2003 | Freeman et al. |
| 2003/0097092 A1 | 5/2003 | Flaherty |
| 2003/0100040 A1 | 5/2003 | Bonnecaze et al. |
| 2003/0109775 A1 | 6/2003 | O'Neil et al. |
| 2003/0134347 A1 | 7/2003 | Heller et al. |
| 2003/0135333 A1 | 7/2003 | Aceti et al. |
| 2003/0144581 A1 | 7/2003 | Conn et al. |
| 2003/0144608 A1 | 7/2003 | Kojima et al. |
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0199910 A1 | 10/2003 | Boecker et al. |
| 2003/0212379 A1 | 11/2003 | Bylund et al. |
| 2003/0217966 A1 | 11/2003 | Tapsak et al. |
| 2003/0225361 A1 | 12/2003 | Sabra |
| 2004/0002382 A1 | 1/2004 | Kovelman et al. |
| 2004/0010207 A1 | 1/2004 | Flaherty et al. |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0064133 A1 | 4/2004 | Miller et al. |
| 2004/0096959 A1 | 5/2004 | Stiene et al. |
| 2004/0106858 A1 | 6/2004 | Say et al. |
| 2004/0106859 A1 | 6/2004 | Say et al. |
| 2004/0116847 A1 | 6/2004 | Wall |
| 2004/0116865 A1 | 6/2004 | Bengtsson |
| 2004/0116866 A1 | 6/2004 | Gorman et al. |
| 2004/0122353 A1 | 6/2004 | Shahmirian et al. |
| 2004/0122489 A1 | 6/2004 | Mazar et al. |
| 2004/0133164 A1 | 7/2004 | Funderbunk et al. |
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |
| 2004/0147996 A1 | 7/2004 | Miazga et al. |
| 2004/0152622 A1 | 8/2004 | Keith et al. |
| 2004/0158207 A1 | 8/2004 | Hunn et al. |
| 2004/0167801 A1 | 8/2004 | Say et al. |
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |
| 2004/0210122 A1 | 10/2004 | Sleburg |
| 2004/0223985 A1 | 11/2004 | Dunfield et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0254433 A1 | 12/2004 | Bandis et al. |
| 2004/0254434 A1 | 12/2004 | Goodnow et al. |
| 2004/0267300 A1 | 12/2004 | Mace et al. |
| 2005/0003470 A1 | 1/2005 | Nelson et al. |
| 2005/0004494 A1 | 1/2005 | Perez et al. |
| 2005/0006122 A1 | 1/2005 | Burnette |
| 2005/0010269 A1 | 1/2005 | Lebel et al. |
| 2005/0027177 A1 | 2/2005 | Shin et al. |
| 2005/0027180 A1 | 2/2005 | Goode, Jr. et al. |
| 2005/0031689 A1 | 2/2005 | Shults et al. |
| 2005/0043598 A1 | 2/2005 | Goode, Jr. et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0106713 A1 | 5/2005 | Phan et al. |
| 2005/0112169 A1 | 5/2005 | Brauker et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154410 A1 | 7/2005 | Conway et al. |
| 2005/0165404 A1 | 7/2005 | Miller |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0199494 A1 | 9/2005 | Say et al. |
| 2005/0203360 A1 | 9/2005 | Brauker et al. |
| 2005/0222518 A1 | 10/2005 | Dib |
| 2005/0222599 A1 | 10/2005 | Czernecki et al. |
| 2005/0235156 A1 | 10/2005 | Drucker et al. |
| 2005/0236277 A9 | 10/2005 | Imran et al. |
| 2005/0239154 A1 | 10/2005 | Feldman et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245844 A1 | 11/2005 | Mace et al. |
| 2005/0277164 A1 | 12/2005 | Drucker et al. |
| 2005/0283114 A1 | 12/2005 | Bresina et al. |
| 2005/0287620 A1 | 12/2005 | Heller et al. |
| 2006/0001538 A1 | 1/2006 | Kraft et al. |
| 2006/0004303 A1 | 1/2006 | Weidenhaupt et al. |
| 2006/0009727 A1 | 1/2006 | O'Mahony et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |

(56) References Cited

U.S. PATENT DOCUMENTS

| | | |
|---|---|---|
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0047220 A1 | 3/2006 | Sakata et al. |
| 2006/0081469 A1 | 4/2006 | Lee |
| 2006/0129173 A1 | 6/2006 | Wilkinson |
| 2006/0155210 A1 | 7/2006 | Beckman et al. |
| 2006/0155317 A1 | 7/2006 | List et al. |
| 2006/0166629 A1 | 7/2006 | Reggiardo |
| 2006/0173444 A1 | 8/2006 | Choy et al. |
| 2006/0189863 A1 | 8/2006 | Peyser et al. |
| 2006/0189939 A1 | 8/2006 | Gonnelli et al. |
| 2006/0195029 A1 | 8/2006 | Shults et al. |
| 2006/0200181 A1 | 9/2006 | Fukuzawa et al. |
| 2006/0200970 A1 | 9/2006 | Brister et al. |
| 2006/0222566 A1 | 10/2006 | Brauker et al. |
| 2006/0224171 A1 | 10/2006 | Sakata et al. |
| 2006/0226985 A1 | 10/2006 | Goodnow et al. |
| 2006/0247508 A1 | 11/2006 | Fennell |
| 2006/0253086 A1 | 11/2006 | Moberg et al. |
| 2006/0258929 A1 | 11/2006 | Goode, Jr. et al. |
| 2006/0264888 A1 | 11/2006 | Moberg et al. |
| 2006/0276724 A1 | 12/2006 | Freeman et al. |
| 2006/0282042 A1 | 12/2006 | Walters et al. |
| 2006/0287591 A1 | 12/2006 | Ocvirk et al. |
| 2007/0016381 A1 | 1/2007 | Kamath et al. |
| 2007/0027381 A1 | 2/2007 | Stafford |
| 2007/0038044 A1 | 2/2007 | Dobbles et al. |
| 2007/0060814 A1 | 3/2007 | Stafford |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0088377 A1 | 4/2007 | Levaughn et al. |
| 2007/0106135 A1 | 5/2007 | Sloan et al. |
| 2007/0110124 A1 | 5/2007 | Zaragoza et al. |
| 2007/0123819 A1 | 5/2007 | Mernoe et al. |
| 2007/0149875 A1 | 6/2007 | Ouyang et al. |
| 2007/0156094 A1 | 7/2007 | Safabash et al. |
| 2007/0163880 A1 | 7/2007 | Woo et al. |
| 2007/0173706 A1 | 7/2007 | Neinast et al. |
| 2007/0173741 A1 | 7/2007 | Deshmukh et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0213611 A1 | 9/2007 | Simpson et al. |
| 2007/0235331 A1 | 10/2007 | Simpson et al. |
| 2007/0244368 A1 | 10/2007 | Bayloff et al. |
| 2007/0244398 A1 | 10/2007 | Lo et al. |
| 2007/0249922 A1 | 10/2007 | Peyser et al. |
| 2007/0255302 A1 | 11/2007 | Koeppel et al. |
| 2008/0004512 A1 | 1/2008 | Funderburk et al. |
| 2008/0004573 A1 | 1/2008 | Kaufmann et al. |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0021666 A1 | 1/2008 | Goode, Jr. et al. |
| 2008/0027474 A1 | 1/2008 | Curry et al. |
| 2008/0029391 A1 | 2/2008 | Mao et al. |
| 2008/0031941 A1 | 2/2008 | Pettersson |
| 2008/0033254 A1 | 2/2008 | Kamath et al. |
| 2008/0033268 A1 | 2/2008 | Stafford |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0064937 A1 | 3/2008 | McGarraugh et al. |
| 2008/0064941 A1 | 3/2008 | Funderburk et al. |
| 2008/0064944 A1 | 3/2008 | VanAntwerp et al. |
| 2008/0065646 A1 | 3/2008 | Zhang et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097246 A1 | 4/2008 | Stafford |
| 2008/0108942 A1 | 5/2008 | Brister et al. |
| 2008/0112848 A1 | 5/2008 | Huffstodt et al. |
| 2008/0114280 A1 | 5/2008 | Stafford |
| 2008/0119707 A1 | 5/2008 | Stafford |
| 2008/0133702 A1 | 6/2008 | Sharma et al. |
| 2008/0154205 A1 | 6/2008 | Wojcik |
| 2008/0161664 A1 | 7/2008 | Mastrototaro et al. |
| 2008/0167578 A1 | 7/2008 | Bryer et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0214481 A1 | 9/2008 | Challoner et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0255440 A1 | 10/2008 | Eilersen et al. |
| 2008/0262469 A1 | 10/2008 | Brister et al. |
| 2008/0269673 A1 | 10/2008 | Butoi et al. |
| 2008/0275313 A1 | 11/2008 | Brister et al. |
| 2008/0283396 A1 | 11/2008 | Wang et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0005659 A1 | 1/2009 | Kollias et al. |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0036915 A1 | 2/2009 | Karbowniczek et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0054866 A1 | 2/2009 | Teisen-Simony et al. |
| 2009/0062633 A1 | 3/2009 | Brauker et al. |
| 2009/0062635 A1 | 3/2009 | Brauker et al. |
| 2009/0069658 A1 | 3/2009 | Say et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0088614 A1 | 4/2009 | Taub |
| 2009/0088787 A1 | 4/2009 | Koike et al. |

(56) References Cited

U.S. PATENT DOCUMENTS

| | | |
|---|---|---|
| 2009/0099436 A1 | 4/2009 | Brister et al. |
| 2009/0102678 A1 | 4/2009 | Mazza et al. |
| 2009/0105569 A1 | 4/2009 | Stafford |
| 2009/0118592 A1 | 5/2009 | Klitgaard |
| 2009/0124877 A1 | 5/2009 | Shariati et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0124979 A1 | 5/2009 | Raymond et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielson |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0171182 A1 | 7/2009 | Stafford |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198215 A1 | 8/2009 | Chong et al. |
| 2009/0203981 A1 | 8/2009 | Brauker et al. |
| 2009/0204341 A1 | 8/2009 | Brauker et al. |
| 2009/0212766 A1 | 8/2009 | Olson et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0259118 A1 | 10/2009 | Feldman et al. |
| 2009/0259201 A1 | 10/2009 | Hwang et al. |
| 2009/0259202 A1 | 10/2009 | Leeflang et al. |
| 2009/0270765 A1 | 10/2009 | Ghesquire et al. |
| 2009/0287073 A1 | 11/2009 | Boock et al. |
| 2009/0287074 A1 | 11/2009 | Shults et al. |
| 2009/0292184 A1 | 11/2009 | Funderburk et al. |
| 2009/0292185 A1 | 11/2009 | Funderburk et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2010/0004597 A1 | 1/2010 | Glyn et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022863 A1 | 1/2010 | Mogensen et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0036281 A1 | 2/2010 | Doi |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0106088 A1 | 4/2010 | Yodfat et al. |
| 2010/0113894 A1 | 5/2010 | Brenneman et al. |
| 2010/0119693 A1 | 5/2010 | Tapsak et al. |
| 2010/0121169 A1 | 5/2010 | Petisce et al. |
| 2010/0168677 A1 | 7/2010 | Gabriel et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode, Jr. et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0186069 A1 | 7/2010 | Brister et al. |
| 2010/0186070 A1 | 7/2010 | Brister et al. |
| 2010/0186071 A1 | 7/2010 | Simpson et al. |
| 2010/0186072 A1 | 7/2010 | Goode, Jr. et al. |
| 2010/0186075 A1 | 7/2010 | Brister et al. |
| 2010/0191082 A1 | 7/2010 | Brister et al. |
| 2010/0198033 A1 | 8/2010 | Krulevitch et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0204653 A1 | 8/2010 | Gryn et al. |
| 2010/0212583 A1 | 8/2010 | Brister et al. |
| 2010/0214104 A1 | 8/2010 | Goode, Jr. et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0240975 A1 | 9/2010 | Goode, Jr. et al. |
| 2010/0240976 A1 | 9/2010 | Goode, Jr. et al. |
| 2010/0256471 A1 | 10/2010 | Say et al. |
| 2010/0261987 A1 | 10/2010 | Kamath et al. |
| 2010/0262201 A1 | 10/2010 | He et al. |
| 2010/0274107 A1 | 10/2010 | Boock et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0324392 A1 | 12/2010 | Yee et al. |
| 2010/0324403 A1 | 12/2010 | Brister et al. |
| 2010/0331642 A1 | 12/2010 | Bruce et al. |
| 2010/0331644 A1 | 12/2010 | Neale et al. |
| 2010/0331647 A1 | 12/2010 | Shah et al. |
| 2010/0331648 A1 | 12/2010 | Kamath et al. |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009727 A1 | 1/2011 | Mensinger et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0040256 A1 | 2/2011 | Bobroff et al. |

(56) References Cited

U.S. PATENT DOCUMENTS

| | | |
|---|---|---|
| 2011/0040263 A1 | 2/2011 | Hordum et al. |
| 2011/0046456 A1 | 2/2011 | Hordum et al. |
| 2011/0046467 A1 | 2/2011 | Simpson et al. |
| 2011/0054275 A1 | 3/2011 | Stafford |
| 2011/0060196 A1 | 3/2011 | Stafford |
| 2011/0073475 A1 | 3/2011 | Kastanos et al. |
| 2011/0077490 A1 | 3/2011 | Simpson et al. |
| 2011/0082484 A1 | 4/2011 | Saravia et al. |
| 2011/0106126 A1 | 5/2011 | Love et al. |
| 2011/0118579 A1 | 5/2011 | Goode, Jr. et al. |
| 2011/0118580 A1 | 5/2011 | Goode, Jr. et al. |
| 2011/0124992 A1 | 5/2011 | Brauker et al. |
| 2011/0124997 A1 | 5/2011 | Goode, Jr. et al. |
| 2011/0125410 A1 | 5/2011 | Goode, Jr. et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0137257 A1 | 6/2011 | Gyrn et al. |
| 2011/0144465 A1 | 6/2011 | Shults et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0190603 A1 | 8/2011 | Stafford |
| 2011/0190614 A1 | 8/2011 | Brister et al. |
| 2011/0191044 A1 | 8/2011 | Stafford |
| 2011/0201910 A1 | 8/2011 | Rasdal et al. |
| 2011/0201911 A1 | 8/2011 | Johnson et al. |
| 2011/0218414 A1 | 9/2011 | Kamath et al. |
| 2011/0231107 A1 | 9/2011 | Brauker et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0253533 A1 | 10/2011 | Shults et al. |
| 2011/0257521 A1 | 10/2011 | Fraden |
| 2011/0257895 A1 | 10/2011 | Brauker et al. |
| 2011/0263958 A1 | 10/2011 | Brauker et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0288574 A1* | 11/2011 | Curry .............. A61B 5/150511 606/185 |
| 2011/0290645 A1 | 12/2011 | Brister et al. |
| 2011/0313543 A1 | 12/2011 | Brauker et al. |
| 2011/0319729 A1 | 12/2011 | Donnay et al. |
| 2011/0319733 A1 | 12/2011 | Stafford |
| 2011/0319738 A1 | 12/2011 | Woodruff et al. |
| 2011/0319739 A1 | 12/2011 | Kamath et al. |
| 2011/0320130 A1 | 12/2011 | Valdes et al. |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0108934 A1 | 5/2012 | Valdes et al. |
| 2012/0108983 A1 | 5/2012 | Banet et al. |
| 2012/0123385 A1 | 5/2012 | Edwards et al. |
| 2012/0143135 A1 | 6/2012 | Cole et al. |
| 2012/0184909 A1 | 7/2012 | Gyrn et al. |
| 2012/0296327 A1 | 11/2012 | Hutchins et al. |
| 2013/0047981 A1 | 2/2013 | Bacon |
| 2013/0150691 A1 | 6/2013 | Pace et al. |

FOREIGN PATENT DOCUMENTS

| | | |
|---|---|---|
| DE | 4401400 | 7/1995 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1177802 | 2/2002 |
| EP | 0987982 | 1/2007 |
| EP | 2060284 | 5/2009 |
| EP | 2201969 | 6/2010 |
| EP | 2327362 | 6/2011 |
| EP | 2335587 | 6/2011 |
| JP | 11-506629 | 6/1999 |
| JP | 2004-520103 | 7/2004 |
| JP | 2004/520898 | 7/2004 |
| WO | WO-1991/015993 | 10/1991 |
| WO | WO-1992/013271 | 8/1992 |
| WO | WO-1994/020602 | 9/1994 |
| WO | WO-1996/025089 | 8/1996 |
| WO | WO-1998/035053 | 8/1998 |
| WO | WO-1998/056293 | 12/1998 |
| WO | WO-1999/033504 | 7/1999 |
| WO | WO-1999/056613 | 11/1999 |
| WO | WO-2000/049940 | 8/2000 |
| WO | WO-2000/059370 | 10/2000 |
| WO | WO-2000/078992 | 12/2000 |
| WO | WO-2001/052935 | 7/2001 |
| WO | WO-2001/054753 | 8/2001 |
| WO | WO-2002/016905 | 2/2002 |
| WO | WO-2002/050534 | 6/2002 |
| WO | WO-2002/058537 | 8/2002 |
| WO | WO-2003/028784 | 4/2003 |
| WO | WO-2003/076893 | 9/2003 |
| WO | WO-2003/082091 | 10/2003 |
| WO | WO-2004/028337 | 4/2004 |
| WO | WO-2004/060436 | 7/2004 |
| WO | WO-2004/061420 | 7/2004 |
| WO | WO-2004/098684 | 11/2004 |
| WO | WO-2004/112602 | 12/2004 |
| WO | WO-2005/084534 | 9/2005 |
| WO | WO-2005/089103 | 9/2005 |
| WO | WO-2006/024671 | 3/2006 |
| WO | WO-2006/042811 | 4/2006 |
| WO | WO-2006/108809 | 10/2006 |
| WO | WO-2007/002189 | 1/2007 |
| WO | WO-2007/089738 | 8/2007 |
| WO | WO-2007/140783 | 12/2007 |
| WO | WO-2008/014792 | 2/2008 |
| WO | WO-2008/065646 | 6/2008 |
| WO | WO-2008/133702 | 11/2008 |
| WO | WO-2009/062675 | 5/2009 |
| WO | WO-2009/068661 | 6/2009 |
| WO | WO-2010/112521 | 10/2010 |
| WO | WO-2011/002815 | 1/2011 |
| WO | WO-2011/015659 | 2/2011 |
| WO | WO 2011/025549 A1 | 3/2011 |
| WO | WO 2011/119896 A1 | 9/2011 |

OTHER PUBLICATIONS

Armour, J. C., et al., "Application of Chronic Intravascular Blood Glucose Sensor in Dogs", Diabetes, vol. 39, 1990, pp. 1519-1526.

Aussedat, B., et al., "A User-Friendly Method for Calibrating a Subcutaneous Glucose Sensor-Based Hypoglycaemic Alarm", Biosensors & Bioelectronics, vol. 12, No. 11, 1997, pp. 1061-1071.

Bennion, N., et al., "Alternate Site Glucose Testing: A Crossover Design", Diabetes Technology & Therapeutics, vol. 4, No. 1, 2002, pp. 25-33.

Bindra, D. S., et al., "Design and in Vitro Studies of a Needle-Type Glucose Sensor for Subcutaneous Monitoring", Analytical Chemistry, vol. 63, No. 17, 1991, pp. 1692-1696.

Bindra, D. S., et al., "Pulsed Amperometric Detection of Glucose in Biological Fluids at a Surface-Modified Gold Electrode", Analytical Chemistry, vol. 61, No. 22, 1989, pp. 2566-2570.

Bobbioni-Harsch, E., et al., "Lifespan of Subcutaneous Glucose Sensors and Their Performances During Dynamic Glycaemia Changes in Rats", Journal of Biomedical Engineering, vol. 15, 1993, pp. 457-463.

Cass, A. E., et al., "Ferrocene-Medicated Enzyme Electrode for Amperometric Determination of Glucose", Analytical Chemistry, vol. 56, No. 4, 1984, pp. 667-671.

Claremont, D. J., et al., "Biosensors for Continuous In Vivo Glucose Monitoring", Proceedings of the Annual International Conference of the IEEE Engineering in Medicine and Biology Society, vol. 10, 1988.

(56) References Cited

OTHER PUBLICATIONS

Clark Jr., L. C., et al., "Electrode Systems for Continuous Monitoring in Cardiovascular Surgery", Annals New York Academy of Sciences, 1962, pp. 29-45.

Clark Jr., L. C., et al., "Long-term Stability of Electroenzymatic Glucose Sensors Implanted in Mice", American Society of Artificial Internal Organs Transactions, vol. XXXIV, 1988, pp. 259-265.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Csoregi, E., et al., "Design, Characterization, and One-Point in Vivo Calibration of a Subcutaneously Implanted Glucose Electrode", Analytical Chemistry, vol. 66, No. 19, 1994, pp. 3131-3138.

Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care Inc. Freestyle Navigator Continuous Glucose Monitor Pamphlet, 2004.

Gregg, B. A., et al., "Cross-Linked Redox Gels Containing Glucose Oxidase for Amperometric Biosensor Applications", Analytical Chemistry, vol. 62, No. 3, 1990, pp. 258-263.

Gunasingham, et al., "Electrochemically Modulated Optrode for Glucose", Biosensors & Bioelectronics, vol. 7, 1992, pp. 353-359.

Harrison, D. J., et al., "Characterization of Perfluorosulfonic Acid Polymer Coated Enzyme Electrodes and a Miniatureized Integrated Potentiostat for Glucose Analysis in Whole Blood", Analytical Chemistry, vol. 60, No. 19, 1988, pp. 2002-2007.

Heller, A., "Electrical Connection Enzyme Redox Centers to Electrodes", Journal of Physical Chemistry, vol. 96, No. 9, 1990, pp. 3579-3587.

Ikeda, T., et al., "Artificial Pancreas—Investigation of the Stability of Glucose Sensors Using a Telemetry System" (English translation of abstract), Jpn. J. Artif. Organs, vol. 19, No. 2, 1990, pp. 889-892.

Isermann, R., "Supervision, Fault-Detection and Fault-Diagnosis Methods—An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

Johnson, K. W., "Peripheral Circulation", John Wiley & Sons, 1978, pp. 19889.

Johnson, K. W., et al., "In vivo Evaluation of an Electroenzymatic Glucose Sensor Implanted in Subcutaneous Tissue", Biosensors & Bioelectronics, vol. 7, 1992, pp. 709-714.

Jungheim, K., et al., "How Rapid Does Glucose Concentration Change in Daily Life of Patients with Type 1 Diabetes?", Diabetologia, 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Koudelka, M., et al., "In-Vivo Behaviour of Hypodermically Implanted Microfabricated Glucose Sensors", Biosensors & Bioelectronics, vol. 6, 1991, pp. 31-36.

Lager, W., et al., "Implantable Electrocatalytic Glucose Sensor", Hormone Metabolic Research, vol. 26, 1994, pp. 526-530.

Maidan, R., et al., "Elimination of Electrooxidizable Interferant-Produced Currents in Amperometric Biosensors", Analytical Chemistry, vol. 64, No. 23, 1992, pp. 2889-2896.

Mastrototaro, J. J., et al., "An Electroenzymatic Glucose Sensor Fabricated on a Flexible Substrate", Sensors and Actuators B, vol. 5, 1991, pp. 139-144.

McKean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.

Minimed Technologies, "Tape Tips and Other Infusion Site Information", 1995.

Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, vol. 7, 1992, pp. 345-352.

Moatti-Sirat, D., et al., "Reduction of Acetaminophen Interference in Glucose Sensors by a Composite Nafion Membrane: Demonstration in Rats and Man", Diabetologia, vol. 37, 1994, pp. 610-616.

Moatti-Sirat, D., et al., "Towards Continuous Glucose Monitoring: In Vivo Evaluation of a Miniaturized Glucose Sensor Implanted for Several Days in Rat Subcutaneous Tissue", Diabetologia, vol. 35, 1992, pp. 224-330.

Ohara, T. J., et al., "Glucose Electrodes Based on Cross-Linked $[Os(bpy)_2Cl]^{+/2+}$ Complexed Poly(1-Vinylimidazole) Films", Analytical Chemistry, vol. 65, No. 23, 1993, pp. 3512-3517.

Olievier, C. N., et al., "In Vivo Measurement of Carbon Dioxide Tension with a Miniature Electrodes", Pflugers Archiv: European Journal of Physiology, vol. 373, 1978, pp. 269-272.

Pickup, J., et al., "Implantable Glucose Sensors: Choosing the Appropriate Sensing Strategy", Biosensors, vol. 3, 1987/88, pp. 335-346.

Pickup, J., "Developing Glucose Sensors for In Vivo Use", Tibtech, vol. 11, 1993, pp. 285-291.

Pickup, J., et al., "Potentially-Implantable, Amperometric Glucose Sensors with Mediated Electron Transfer: Improving the Operating Stability", Biosensors, vol. 4, 1989, pp. 109-119.

Pickup, J., et al., "In Vivo Molecular Sensing in Diabetes Mellitus: An Implantable Glucose Sensor with Direct Electron Transfer", Diabetologia, vol. 32, 1989, pp. 213-217.

Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.

Poitout, V., et al., "A Glucose Monitoring System for on Line Estimation in Man of Blood Glucose Concentration Using a Miniaturized Glucose Sensor Implanted in the Subcutaneous Tissue and a Wearable Control Unit", Diabetolgia, vol. 36, 1993, pp. 658-663.

Poitout, V., et al., "Calibration in Dogs of a Subcutaneous Miniaturized Glucose Sensor Using a Glucose Meter for Blood Glucose Determination", Biosensors & Bioelectronics, vol. 7, 1992, pp. 587-592.

Poitout, V., et al., "In Vitro and In Vivo Evaluation in Dogs of a Miniaturized Glucose Sensor", ASAIO Transactions, vol. 37, No. 3, 1991, pp. M298-M300.

Quinn, C. P., et al., "Kinetics of Glucose Delivery to Subcutaneous Tissue in Rats Measured with 0.3-mm Amperometric Microsensors", The American Physiological Society, 1995, pp. E155-E161.

Ratner, B. D., "Reducing Capsular Thickness and Enhancing Angiogenesis Around Implant Drug Release Systems", Journal of Controlled Release, vol. 78, 2002, pp. 211-218.

Reach, G., et al., "Can Continuous Glucose Monitoring Be Used for the Treatment of Diabetes?", Analytical Chemistry, vol. 64, No. 6, 1992, pp. 381-386.

Rebrin, K., et al., "Automated Feedback Control of Subcutaneous Glucose Concentration in Diabetic Dogs", Diabetologia, vol. 32, 1989, pp. 573-576.

Roe, J. N., et al., "Bloodless Glucose Measurements", Critical Review in Therapeutic Drug Carrier Systems, vol. 15, No. 3, 1998, pp. 199-241.

Sakakida, M., et al., "Development of Ferrocene-Mediated Needle-Type Glucose Sensor as a Measure of True Subcutaneous Tissue Glucose Concentrations," Artificial Organs Today, vol. 2, No. 2, 1992, pp. 145-158.

Sakakida, M., et al., "Ferrocene-Mediated Needle-Type Glucose Sensor Covered with Newly Designed Biocompatible Membrane", Sensors and Actuators B, vol. 13-14, 1993, pp. 319-322.

Salehi, C., et al., "A Telemetry-Instrumentation System for Long-Term Implantable Glucose and Oxygen Sensors", Analytical Letters, vol. 29, No. 13, 1996, pp. 2289-2308.

Scheller, F., et al., "Enzyme Electrodes and Their Application", Philosophical Transactions of the Royal Society of London B, vol. 316, 1987, pp. 85-94.

(56) References Cited

OTHER PUBLICATIONS

Schmidt, F. J., et al., "Calibration of a Wearable Glucose Sensor", The International Journal of Artificial Organs, vol. 15, No. 1, 1992, pp. 55-61.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.
Shichiri, M., et al., "Glycaemic Control in Pancreatectomized Dogs with a Wearable Artificial Endocrine Pancreas", Diabetologia, vol. 24, 1983, pp. 179-184.
Shichiri, M., et al., "In Vivo Characteristics of Needle-Type Glucose Sensor Measurements of Subcutaneous Glucose Concentrations in Human Volunteers", Hormone and Metabolic Research Supplement Series, vol. 20, 1988, pp. 17-20.
Shichiri, M., et al., "Membrane design for extending the long-life of an implantable glucose sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.
Shults, M. C., et al., "A Telemety-Instrumentation System for Monitoring Multiple Subcutaneously Implanted Glucose Sensors", IEEE Transactions on Biomedical Engineering, vol. 41, No. 10, 1994, pp. 937-942.
Sternberg, R., et al., "Study and Development of Multilayer Needle-type Enzyme-based Glucose Microsensors", Biosensors, vol. 4, 1988, pp. 27-40.
Thompson, M., et al., "In Vivo Probes: Problems and Perspectives", Clinical Biochemistry, vol. 19, 1986, pp. 255-261.
Turner, A.P.F., et al., "Diabetes Mellitus: Biosensors for Research and Management", Biosensors, vol. 1, 1985, pp. 85-115.
Updike, S. J., et al., "Principles of Long-term Fully Implanted Sensors with Emphasis on Radiotelemetric Monitoring of Blood Glucose from inside a Subcutaneous Foreign Body Capsule (FBC)", Biosensors in the Body: Continuous In vivo Monitoring, Chapter 4, 1997, pp. 117-137.
Velho, G., et al., "Strategies for calibrating a subcutaneous glucose sensor", Biomedica Biochimica Acta, vol. 48, 1989, pp. 957-964.
Velho, G., et al., "In Vitro and In Vivo Stability of Electrode Potentials in Needle-Type Glucose Sensors", Diabetes, vol. 38, No. 2, 1989, pp. 164-171.
Von Woedtke, T., et al., "In Situ Calibration of Implanted Electrochemical Glucose Sensors", Biomedica Biochimica Acta, vol. 48, 1989, pp. 943-952.
Wilson, G. S., et al., "Progress toward the Development of an Implantable Sensor for Glucose", Clinical Chemistry, vol. 38, No. 9, 1992, pp. 1613-1617.
Ye, L., et al., "High Current Density 'Wired' Quinoprotein Glucose Dehydrogenase Electrode", Analytical Chemistry, vol. 65, No. 3, 1993, pp. 238-241.
PCT/US2012/068839 ISR and Written Opinion dated Feb. 22, 2013.
NL 2009963 Search Report and Written Opinion dated Aug. 12, 2013.
EP 17182379.2 Extended Search Report dated Feb. 21, 2018.
AU, 2011269796 Examination Report, dated Apr. 3, 2014.
EP, 10739015.5 Extended Search Report, dated May 10, 2013.
EP, 11760268.0 Extended Search Report, dated Apr. 14, 2014.
WO, PCT/US2016/032485 ISR and Written Opinion, dated Sep. 12, 2016.
Heller, A., "Electrical Wiring of Redox Enzymes", Accounts of Chemical Research, 1990, vol. 23, No. 5, pp. 128-134.
Shichiri, M., et al., "Wearable Artificial Endocrine Pancreas With Needle-Type Glucose Sensor", The Lancet, 1982, pp. 1129-1131.
Updike, S. J., et al., "A Subcutaneous Glucose Sensor With Improved Longevity, Dynamic Range, and Stability of Calibration", Diabetes Care, 2000, vol. 23, pp. 208-214.
EP 21152231.3 Extended Search Report dated May 11, 2021.

\* cited by examiner

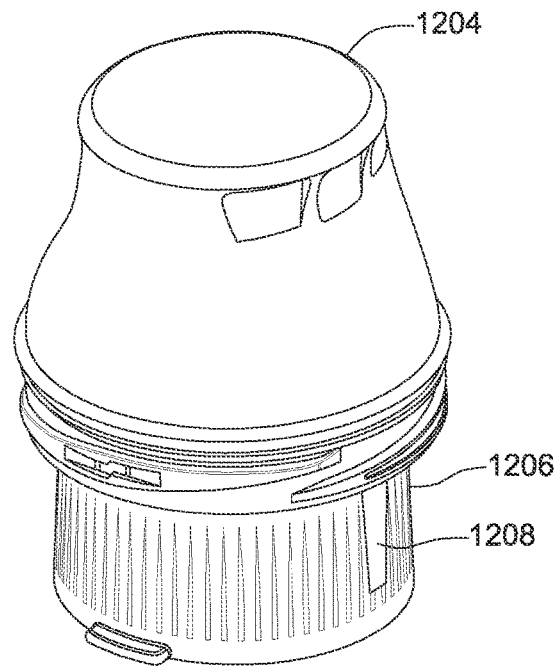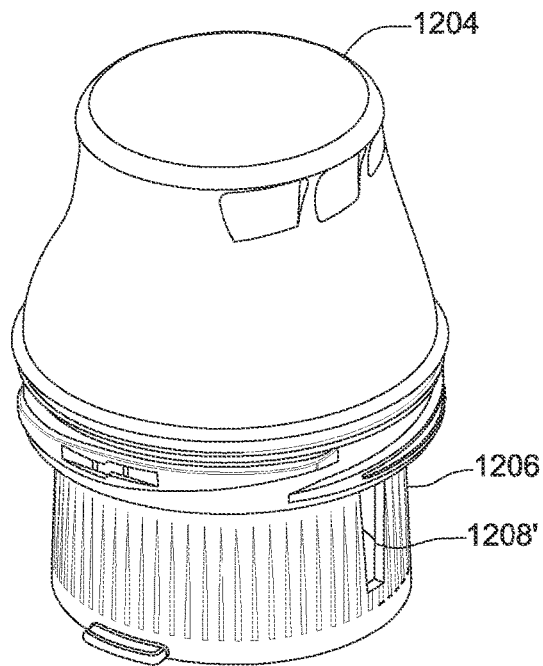
FIG. 13A    FIG. 13B
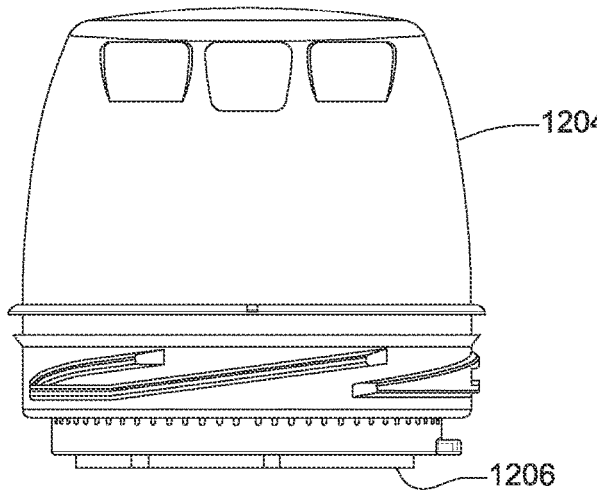
FIG. 13C

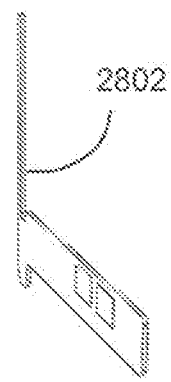
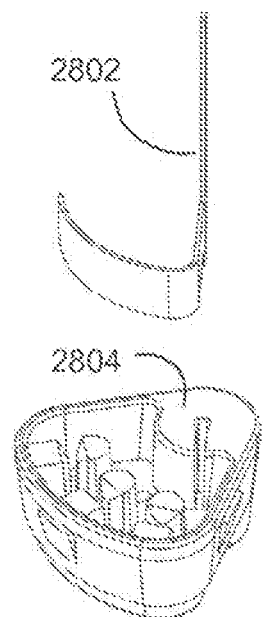
FIG. 28A    FIG. 28B    FIG. 28C
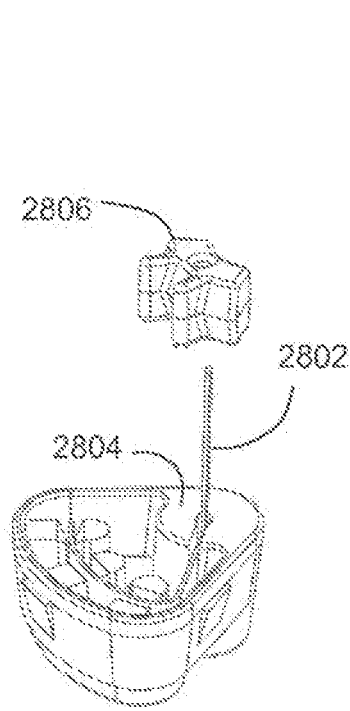
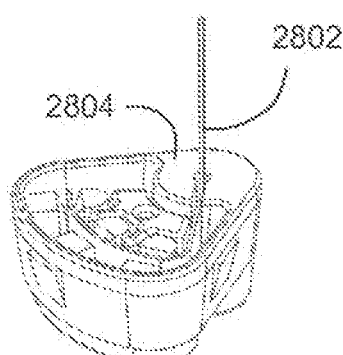
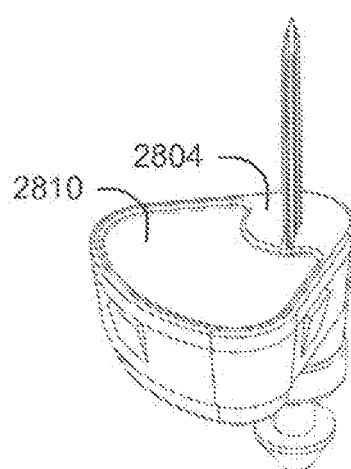
FIG. 28D    FIG. 28E    FIG. 28F

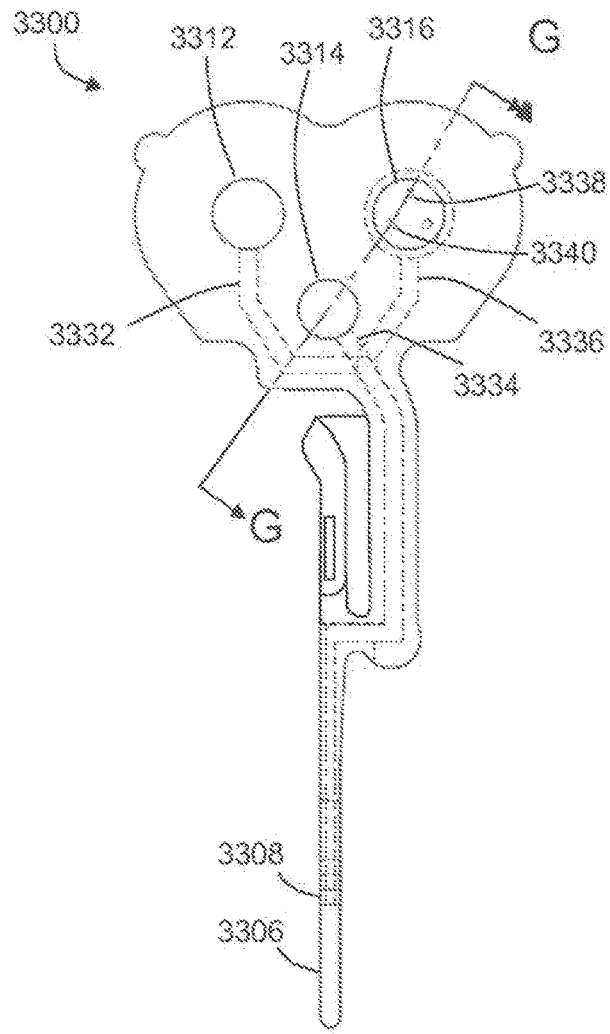
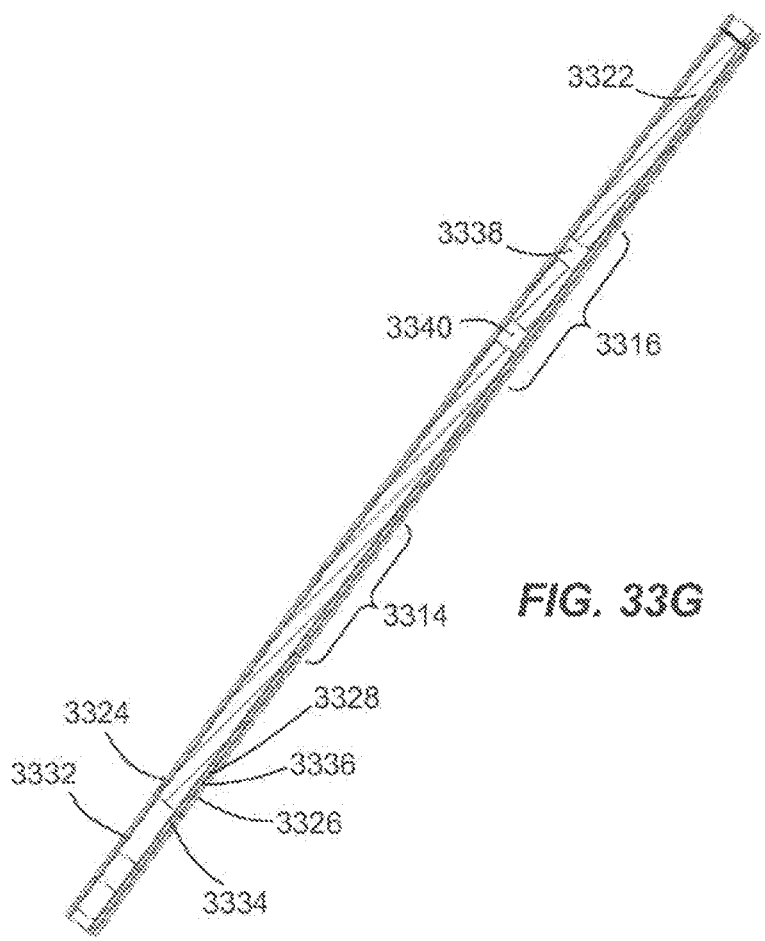
FIG. 33F
FIG. 33G

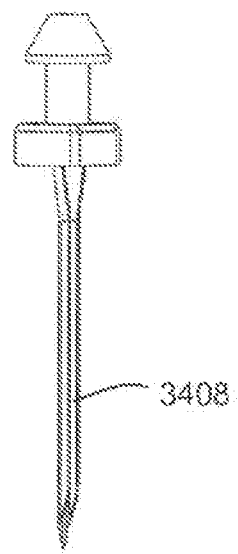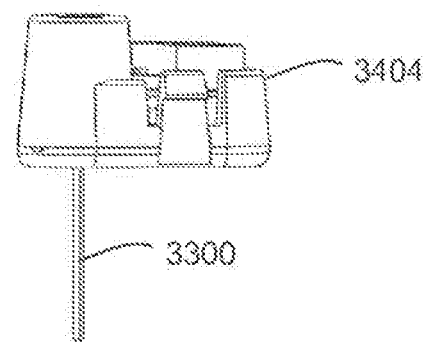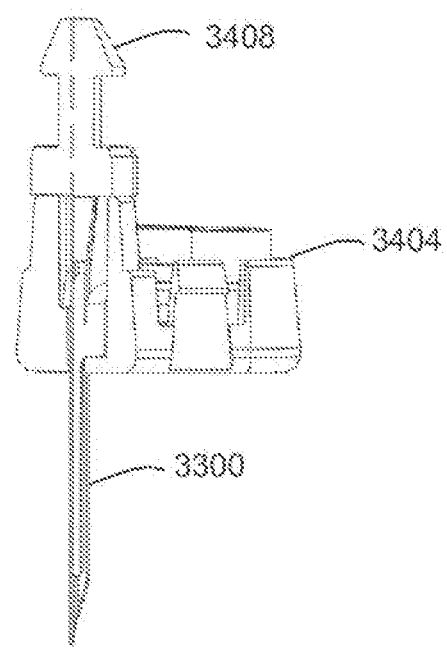
FIG. 35A          FIG. 35B

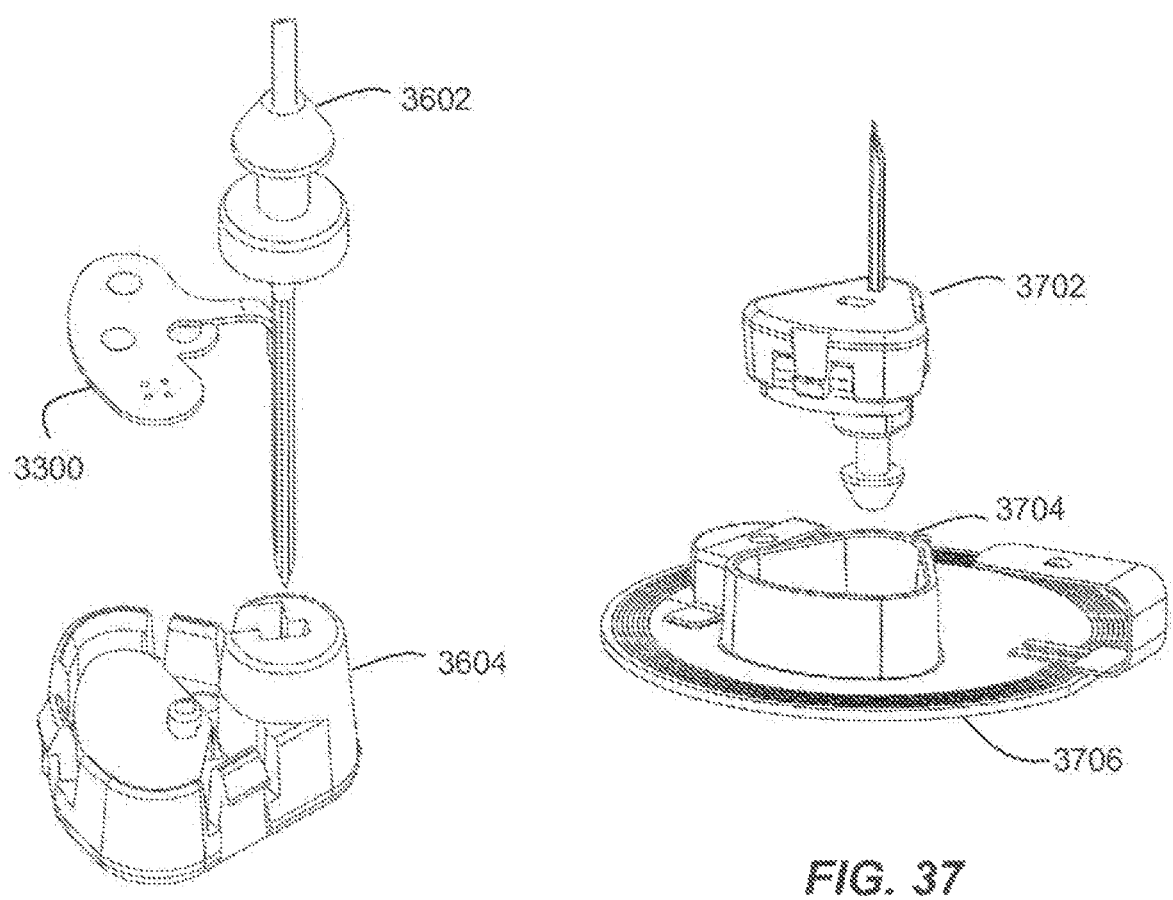
FIG. 36
FIG. 37
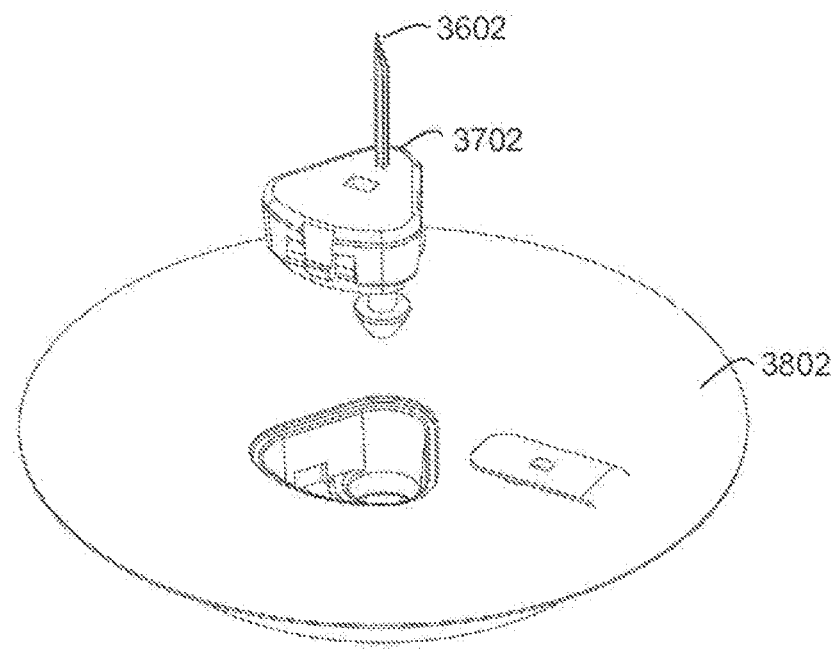
FIG. 38

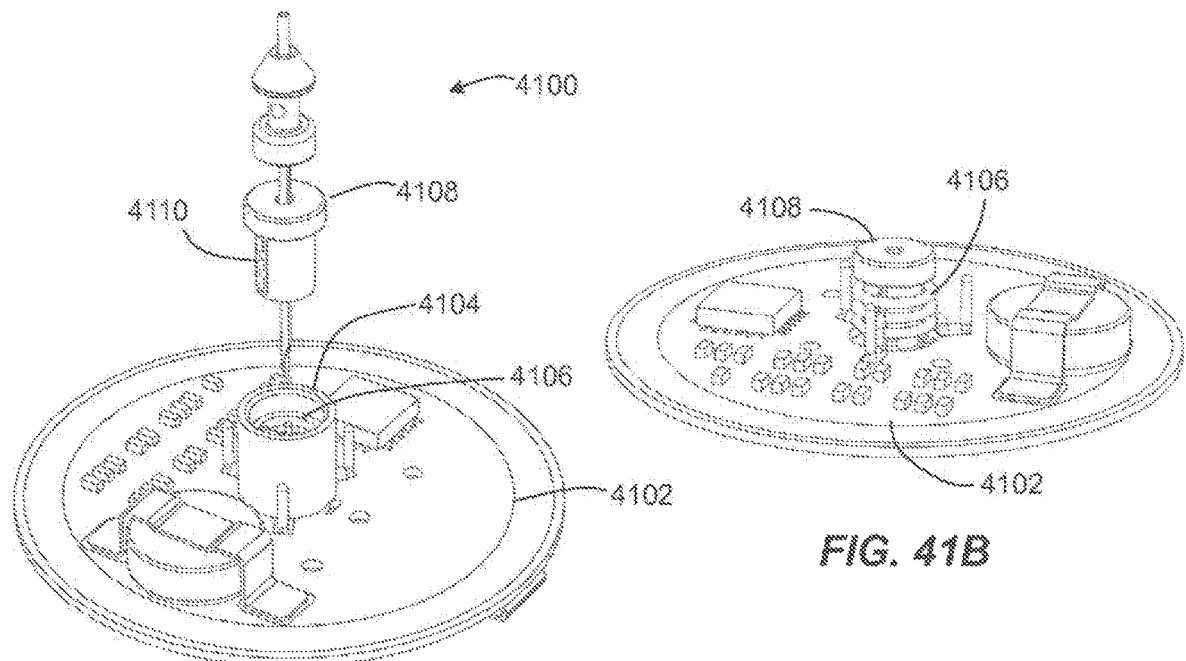
FIG. 41A
FIG. 41B
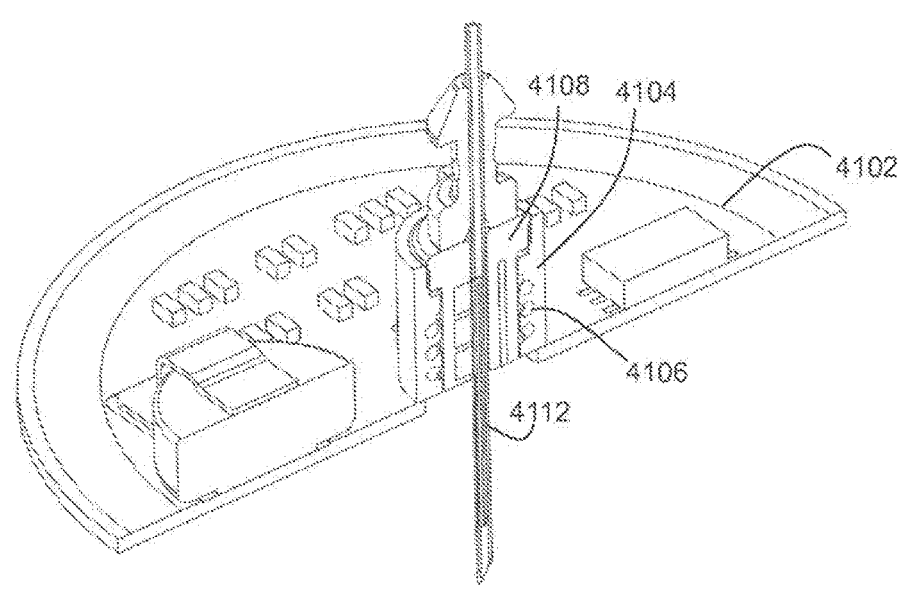
FIG. 41C

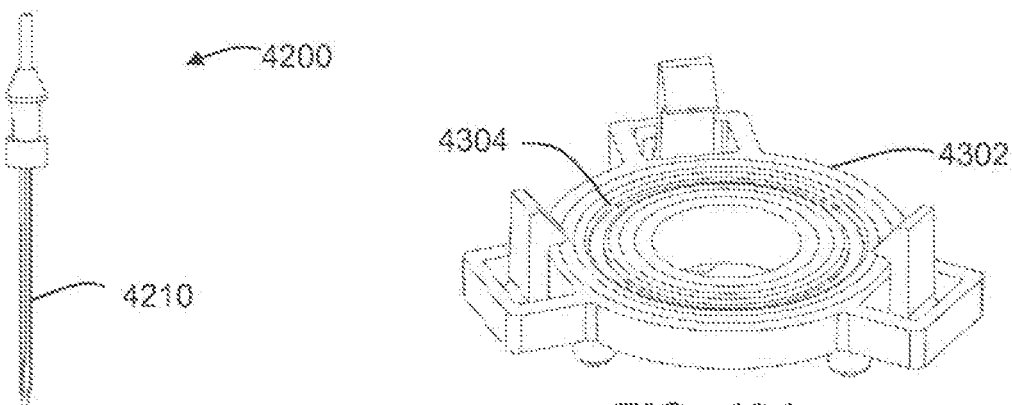
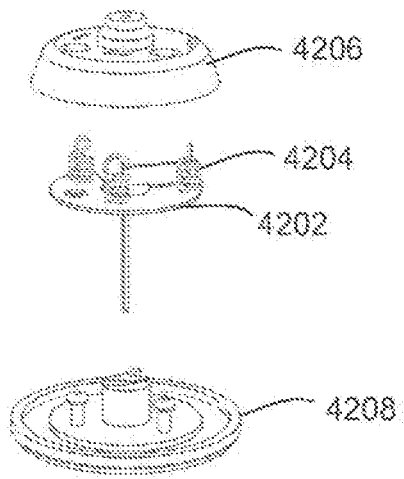
FIG. 42
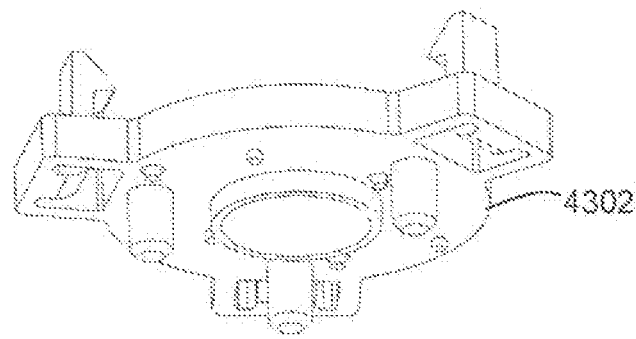
FIG. 43A
FIG. 43B
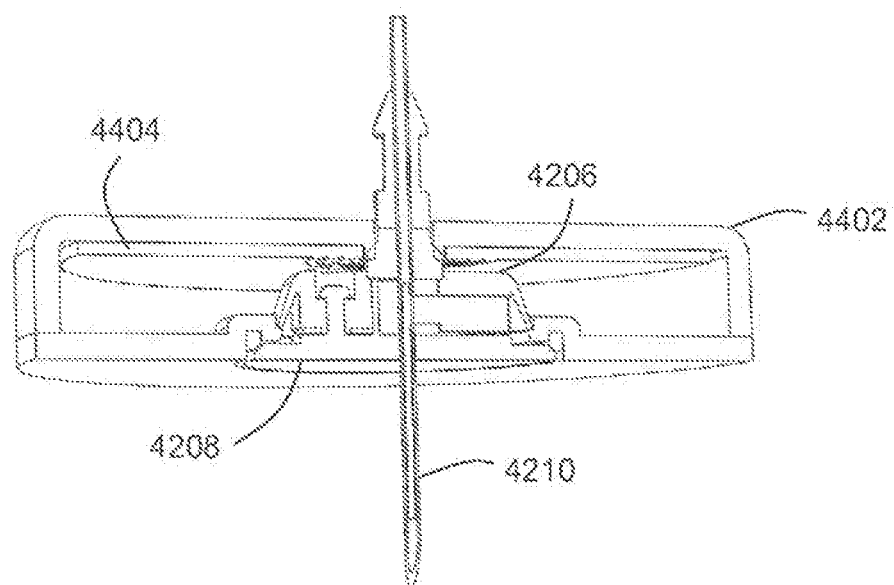
FIG. 44

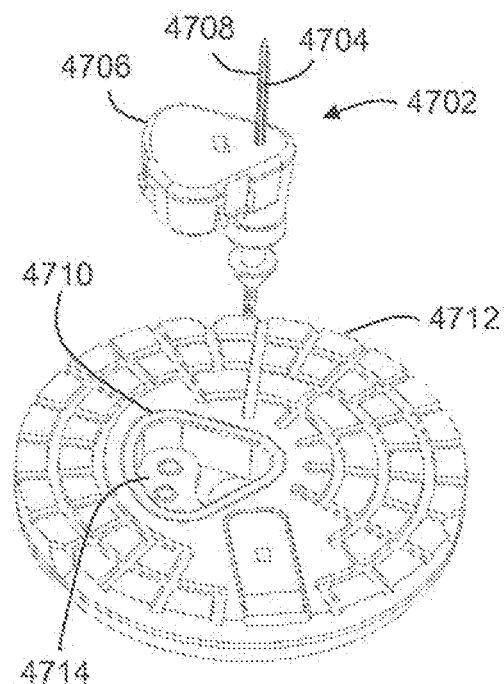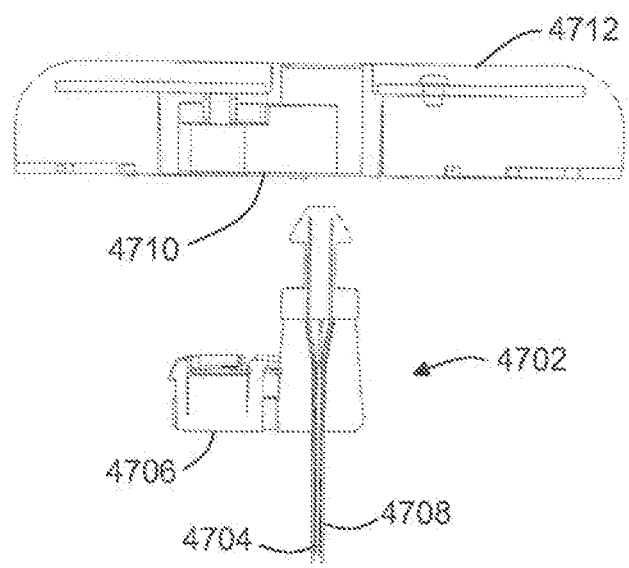
FIG. 47A    FIG. 47B
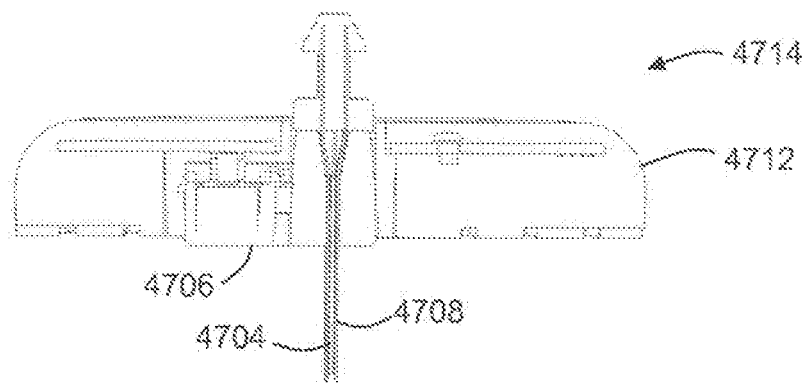
FIG. 47C

FIG. 51A                    FIG. 51B

ANALYTE SENSOR DEVICES, CONNECTIONS, AND METHODS

CROSS-REFERENCE TO RELATED APPLICATIONS

The present application is a continuation of U.S. patent application Ser. No. 15/908,616, filed Feb. 28, 2018, which is a continuation of U.S. patent application Ser. No. 15/610,334, filed May 31, 2017, now U.S. Pat. No. 9,931,066, which is a continuation of U.S. patent application Ser. No. 15/193,499, filed Jun. 27, 2016, now U.S. Pat. No. 9,693,713, which is a continuation of U.S. patent application Ser. No. 13/710,460, filed Dec. 11, 2012, now U.S. Pat. No. 9,402,570, which claims priority to U.S. Provisional Application No. 61/569,287, filed Dec. 11, 2011, all of which are incorporated herein by reference in their entireties for all purposes.

BACKGROUND

Diabetes Mellitus is an incurable chronic disease in which the body does not produce or properly utilize insulin. Insulin is a hormone produced by the pancreas that regulates blood sugar (glucose). In particular, when blood sugar levels rise, e.g., after a meal, insulin lowers the blood sugar levels by facilitating blood glucose to move from the blood into the body cells. Thus, when the pancreas does not produce sufficient insulin (a condition known as Type 1 Diabetes) or does not properly utilize insulin (a condition known as Type II Diabetes), the blood glucose remains in the blood resulting in hyperglycemia or abnormally high blood sugar levels.

The vast and uncontrolled fluctuations in blood glucose levels in people suffering from diabetes cause long-term, serious complications. Some of these complications include blindness, kidney failure, and nerve damage. Additionally, it is known that diabetes is a factor in accelerating cardiovascular diseases such as atherosclerosis (hardening of the arteries), leading to stroke, coronary heart disease, and other diseases. Accordingly, one important and universal strategy in managing diabetes is to control blood glucose levels.

One element of managing blood glucose levels is the monitoring of blood glucose levels. Conventional in vitro techniques, such as drawing blood samples, applying the blood to a test strip, and determining the blood glucose level using colorimetric, electrochemical, or photometric test meters, may be employed. Another technique for monitoring glucose levels uses an in vivo analyte monitoring system, which measures and stores sensor data representative of glucose levels automatically over time.

Unlike conventional in vitro blood glucose monitoring approaches, in vivo analyte monitoring systems use an insertable or implantable in vivo sensor that is positioned to be in contact with interstitial fluid of a user for a period of time to detect and monitor glucose levels. Prior to use of an in vivo sensor, at least a portion of the sensor is positioned under the skin. An applicator assembly can be employed to insert the sensor into the body of the user. For insertion of the sensor, a sharp engaged with the sensor, pierces the skin of the user and is then removed from the body of the user leaving the sensor in place. The in vivo-positioned sensor can be connected to other system components such as sensor electronics contained in a unit that can be held onto the skin.

To realize fully the advantages associated with such systems, what is needed are applicator systems configured to handle insertion, as well as packaging and user interface issues, that are easy-to-use, reliable and minimize both user inconvenience and pain. The present invention provides such solutions and additional or alternative advantages as described below and/or as may be appreciated by those of skill in the art upon review of the subject disclosure.

SUMMARY

The present invention includes packaging, loading systems, applicators, and elements of the on-body devices themselves. According to embodiments of the present invention, an on-body device includes an electronics assembly and a sensor assembly. The sensor assembly includes a sensor and a connector for coupling the sensor to the electronics assembly. In addition, a sharp can be provided that supports the sensor and allows a distal end of the sensor to be placed under a user's skin. In some embodiments, the invention includes the connection of electrochemical analyte sensors to and/or within associated other monitoring components such as system devices that are configured to be held in place on body. The approaches variously involve the use of unique sensor and unique ancillary element arrangements to facilitate assembly of separate on-body devices and sensor assembly units that are kept apart until the user brings them together. Methods associated with such use also form part of the inventive subject matter.

Certain embodiments are described that include an analyte sensor (e.g., a glucose sensor) and an applicator assembly to position a portion of the sensor beneath a skin surface, as well as methods of positioning at least a portion of the sensor and methods of analyte testing or monitoring. Further methods include the manner of preparing the applicator assembly. Namely, such acts associated with user assembly and mating of the component parts of a monitoring system.

As mentioned above, such a monitoring system includes an electronics assembly adapted to adhere to a skin of a subject, a sensor assembly coupled to the electronics assembly to form an on-body device, and an insertion sharp having a longitudinal body including a longitudinal opening to receive at least a portion of the sensor body. The details of the sensor may vary. Exemplary chemistries and constructions are described in any of U.S. Pat. Nos. 5,593,852, 6,284,478, and 6,329,161, each incorporated by reference herein in its entirety. Exemplary form-factors or configurations (e.g., for associated use with an insertion "sharp") are described in any of U.S. Pat. Nos. 6,175,752, 6,565,509, 6,134,461 and 6,990,366 and in U.S. Publication No. 2010/0230285, each incorporated by reference herein in its entirety.

Likewise, the details of the on-body device may vary. For instance, the on-body device may include sensor electronics and other adaptation to communicate with a monitoring device. Various options for communications facilities (e.g., wireless transmitters, transponders, etc.) are described in detail in U.S. Patent Publication Nos. 2010/0198034 and 2011/0213225, the entirety of the applications hereby incorporated by reference, including cited and incorporated references.

In some embodiments, systems and methods are provided for assembling and applying the on-body device including assembling the sensor assembly to the electronics assembly and inserting a portion of the sensor under the skin of a user. Thus, the sensor assembly includes a sensor that has a distal portion for operative contact with a fluid of the user. The on-body device also includes an electronics assembly including a housing defining a distal surface adapted for attachment to the skin of the user and a circuit coupleable to the sensor for detecting electrical signals from the sensor. In some embodiments, the system also includes an applicator assembly that has a sleeve defining a distal surface for placement on the skin of the subject, a handle for a user interface, and various internal support, coupling, guide, grasping, stop and detent features as well as driver elements. In some embodiments, the system may also include a container that stores one or more of the sensor, the sharp, and/or the mount/electronics assembly in a sealed environment within. The container is configured to releasably interface with the applicator assembly for the purpose of loading one or more of the sensor, the sharp, and/or the electronics assembly into the applicator assembly, and readying the applicator assembly for use.

The present disclosure includes the subject systems, devices, kits in which they are included, and methods of use and manufacture. A number of aspects of such manufacture are discussed herein. Further details can be appreciated in reference to the figures and/or associated description.

BRIEF DESCRIPTION OF THE DRAWINGS

A detailed description of various aspects, features, and embodiments of the subject matter described herein is provided with reference to the accompanying drawings, which are briefly described below. The drawings are illustrative and may or may not be drawn to scale, with the possibility of some components and features being exaggerated for clarity. Similar components may be numbered identically or not. The drawings illustrate various aspects and features of the present subject matter and may illustrate one or more embodiment(s) or example(s) of the present subject matter in whole or in part.

FIGS. 13A-13C variously illustrate use of the applicator in FIGS. 12A-12D in connection with a locking-sleeve feature;

FIGS. 28A-F are perspective views of another advantageous sensor and sensor element arrangement;

FIGS. 33A-33G are plane, side, magnified, and sectional views of an additional sensor configuration;

FIG. 36 is a perspective assembly view illustrating a sensor connection approach related to that in FIGS. 34A-34D for a sensor with contacts on a single side;

FIG. 37 is a perspective partial assembly view illustrating a mount-and-socket interface for the sensor assembly employing the components in FIG. 36;

FIG. 38 is a complete assembly view of that illustrated in FIG. 37;

FIGS. 41A and 41B are partial perspective assembly views of another stacked non-directional sensor connection arrangement;

FIG. 41C is a section view of the complete assembly of the components variously illustrated in FIGS. 41A and 41B;

FIG. 42 is an assembly view of an advantageous radial arrangement sensor connector assembly;

FIGS. 43A and 43B are reversed perspective views of the mount-side sensor connection component for use with an assembly as shown in FIG. 42;

FIG. 44 is a section view of the complete assembly of the components variously illustrated in FIGS. 42, 43A and 43B;

FIG. 47A-47C are assembly and cross-sectional views of an on-body device including an integrated connector for the sensor assembly;

DETAILED DESCRIPTION

Figure 1:
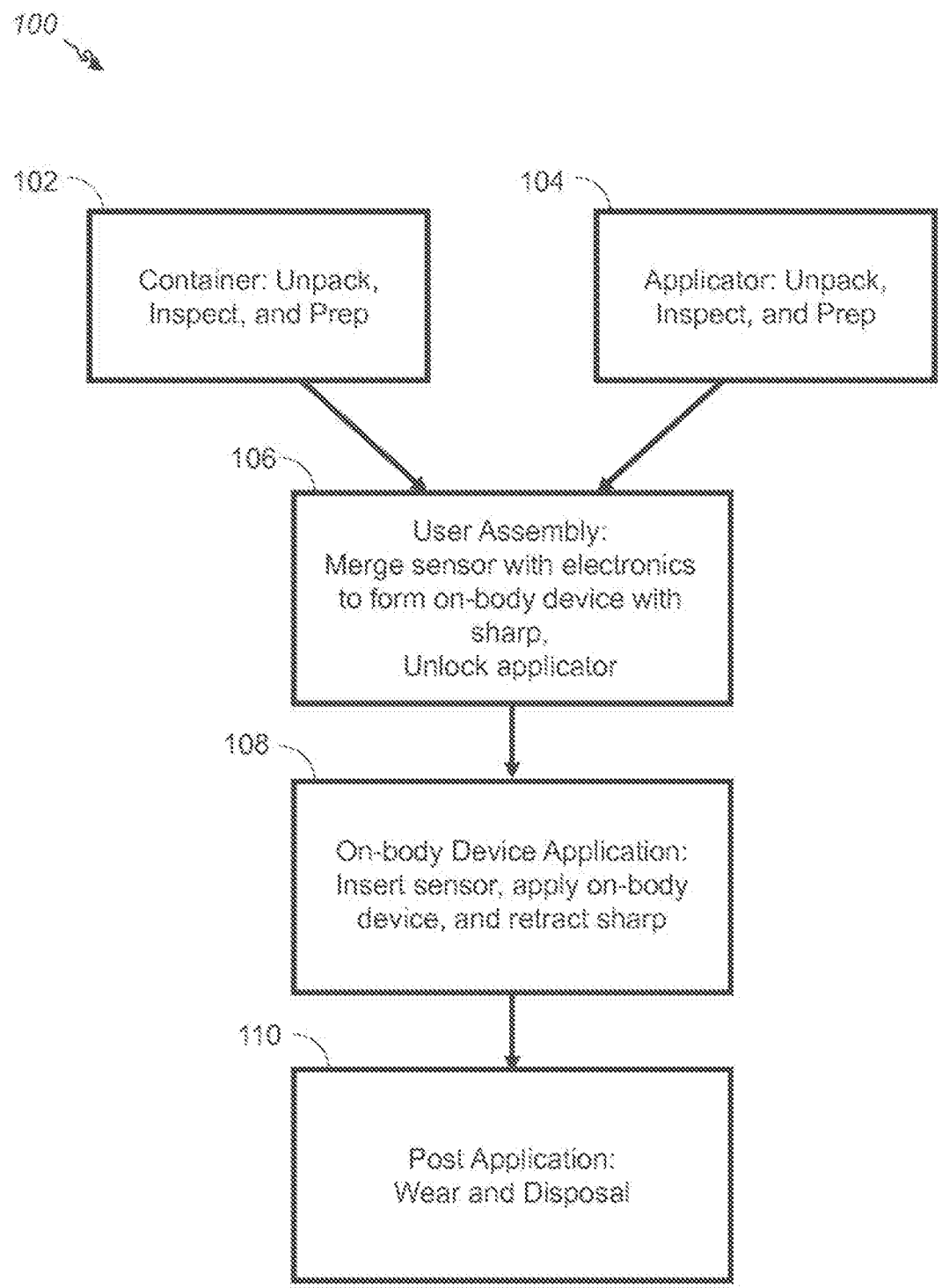
FIG. 1 is a flowchart, indicating user activity in handling the subject devices.

Before the present disclosure is further described, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein includes discrete components and features which may be readily separated from or combined with the features of any of the other several embodiments without departing from the scope or spirit of the present disclosure.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, exemplary methods and materials are now described. All publications mentioned herein are incorporated herein by reference to disclose and describe the methods and/or materials in connection with which the publications are cited.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Various exemplary embodiments of the disclosure are described below. Reference is made to these examples in a non-limiting sense. They are provided to illustrate more broadly applicable aspects of the present disclosure. Various changes may be made to the disclosure described and equivalents may be substituted without departing from the true spirit and scope of the disclosure. In addition, many modifications may be made to adapt a particular situation, material, composition of matter, process, process act(s) or step(s) to the objective(s), spirit or scope of the present disclosure. All such modifications are intended to be within the scope of the claims made herein.

Applicator and Container Overview

Turning to FIG. 1, a flowchart depicting an example method 100 of using various systems of the present invention is provided. In some embodiments, a user starts with unpacking the container (102) and unpacking the applicator (104). Unpacking the container (102) can include removing a cover that provides a sterile seal to the container contents and unpacking the applicator (104) can include removing an end cap that provides a sterile seal to the internal portion of the applicator. Next, in an assembly operation (106), the applicator is inserted into the container to merge or connect the sensor assembly and the electronics assembly together to form an on-body device and an insertion needle or sharp. In some embodiments, the user unlocks the applicator or removes a locking element to ready the applicator for use. The process of the assembly operation (106) and the constituent components are described in detail below.

Next, once the user has chosen an application site, an on-body device application operation (108) is performed. In the application operation (108), the user places the applicator on the skin of the insertion site and then applies a force to install the on-body device. The applicator is driven to insert the distal end of the sensor through the user's skin, adhere the on-body device to the skin surface, and retract the sharp into the applicator for disposal. In some embodiments, the user performs the application operation (108) by applying force to the applicator where the force applied is a single, continuous pushing motion along the longitudinal axis of the applicator that once started, causes the applicator to perform the application operation (108) such that the applicator does not stop operation until completion. The applicator is configured to relay action/audible cues to the user so that all three of the above listed actions happen automatically in response to applying the force to the applicator causing it to trigger. Advantageously, an adhesive of the on-body device does not contact the user until the application operation (108) is performed. So, the even after the applicator has been placed on the skin, the applicator can be moved to a different location up until the application operation (108) is performed without damage to the apparatus or other system components. In a post application stage (110), use of the sensor for monitoring the user's analyte level occurs during wear followed by appropriate disposal.

Figure 2A:
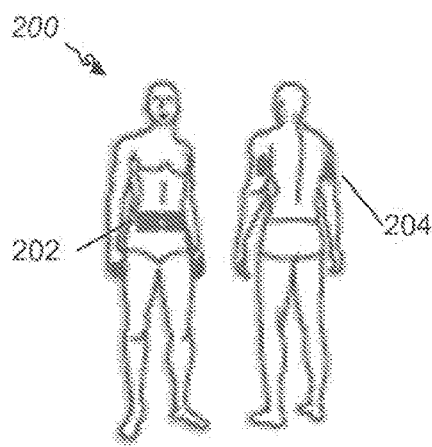
FIGS. 2A-2G illustrate such activity with additional detail.

Details of method 100 are illustrated in the sequence of drawings shown in FIGS. 2A to 2G. In FIG. 2A, one of the highlighted application sites 202, 204 on a user 200 is selected. In some embodiments, other application sites may be used. In some embodiments, a site preparation operation may optionally be performed. The application site 202, 204 may be shaved, exfoliated, cleaned, or otherwise treated to better adhere the on-body device. More specifically, the skin at the site of the user's body where the on-body device will be adhered may be prepared to receive the on-body device. For example, the skin may be shaved with a razor, cleaned with isopropyl alcohol (IPA), and exfoliated with an abrasive. A mechanically exfoliating element can be used to remove an outer layer of dead skin and expose newer skin below. These elements include: microfiber exfoliating cloths; pumice or other abrasive mineral; metal-stamped components of a rasp/file type configuration; synthetic scouring material, e.g., Scotch-Brite®; an alternate adhesive tape or patch to be applied and stripped off to remove dead skin; and organic abrasive elements such as salt, crushed almond shells, apricot kernels, etc. Likewise, a chemically exfoliating element may be used to prepare the site, including: mild acids such as alpha hydroxyl acid, beta-hydroxyl acid and salicylic acid; and fruit enzymes. Such chemically abrasive element(s) may be incorporated in a preparation pad, towelette, swab or be supplied otherwise. In some embodiments, the end cap of the applicator may include one or more exfoliating elements. In some embodiments, the end cap may be textured or otherwise formed to provide a surface that can be used to exfoliate the skin of the site where the on-body device will be adhered. Exfoliating away an outer layer of dead skin before application may allow the on-body device to better adhere to the skin for a longer period of time.

Figure 2B:
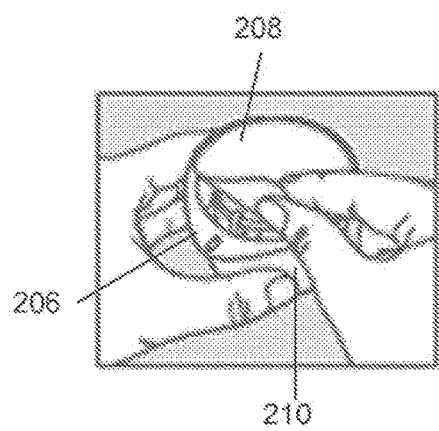
Figure 2C:
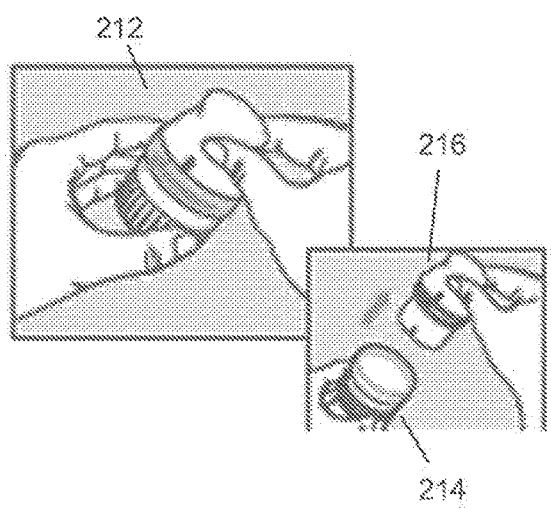

FIG. 2B illustrates loader or container 206 preparation, including removing cover 208 from a casing 210. The container 206 includes the casing 210 which holds the sensor assembly and a sharp (or in some embodiments, the electronics assembly). FIG. 2C illustrates applicator 212 preparation including separating a removable applicator end cap 214 from applicator assembly 216. In some embodiments, container 206 and applicator 212 can initially be packaged connected together to simplify packaging and shipping. For example, the removable applicator end cap 214 may include a boss or other feature that couples or snaps to a corresponding feature on the exterior of the container 206. This connection is only operative to hold the two pieces together for shipping purposes and not for operation of the system. Thus, in some embodiments, before removing the cover 208 from the casing 210 and separating the removable end cap 214 from the applicator assembly 216, in an initial unpacking step, the container 206 and applicator 212 are separated from each other.

Figure 2D:
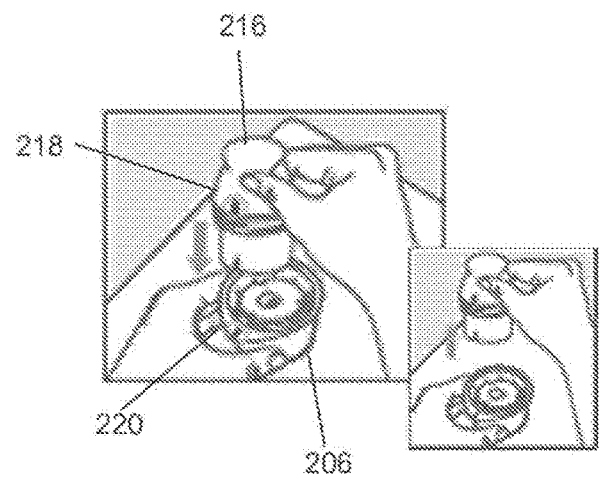
Figure 2E:
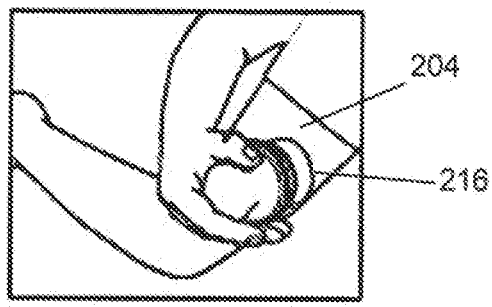
Figure 2F:
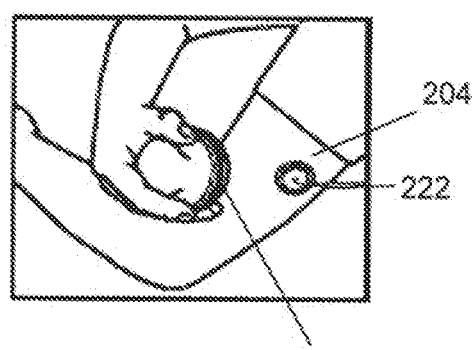
Figure 2G:
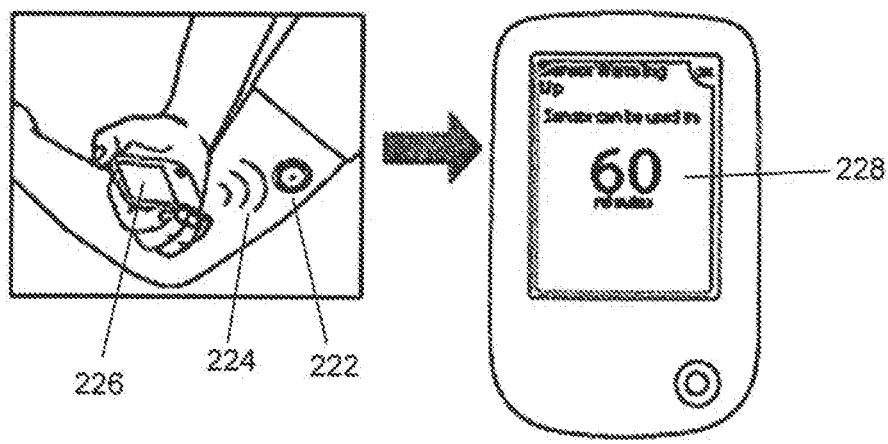

As shown in FIG. 2D, once alignment indicators 218, 220 are aligned, the user assembly operation 106 (FIG. 1) is achieved by pushing the applicator assembly 216 firmly into the container 206 to retrieve a sensor and a sharp from the container and to unlock a guide sleeve of the applicator assembly 216. In FIG. 2E, the assembled and unlocked applicator assembly 216 is placed on the application site 204 (or 202) and pushed down firmly to effect on-body device application 108 (FIG. 1). As shown in FIG. 2F, upon used applicator assembly 216 removal from the application site 204, on-body device 222 is adhered to the user. In some embodiments, as illustrated in FIG. 2G, analyte levels detected by the sensor of the on-body device 222 can be retrieved over a wireless communication link 224 via a communications facility (e.g., a transmitter, a transponder, etc.) within the on-body device 222 by a receiver unit 226 (referred to alternatively as a "reader unit" or "receiver device", or in some contexts, depending on the usage, as a "display unit," "handheld unit," or "meter"). Relevant information (e.g., analyte level trend data, graphs, etc.) is presented on the receiver unit's display 228.

Figure 3:
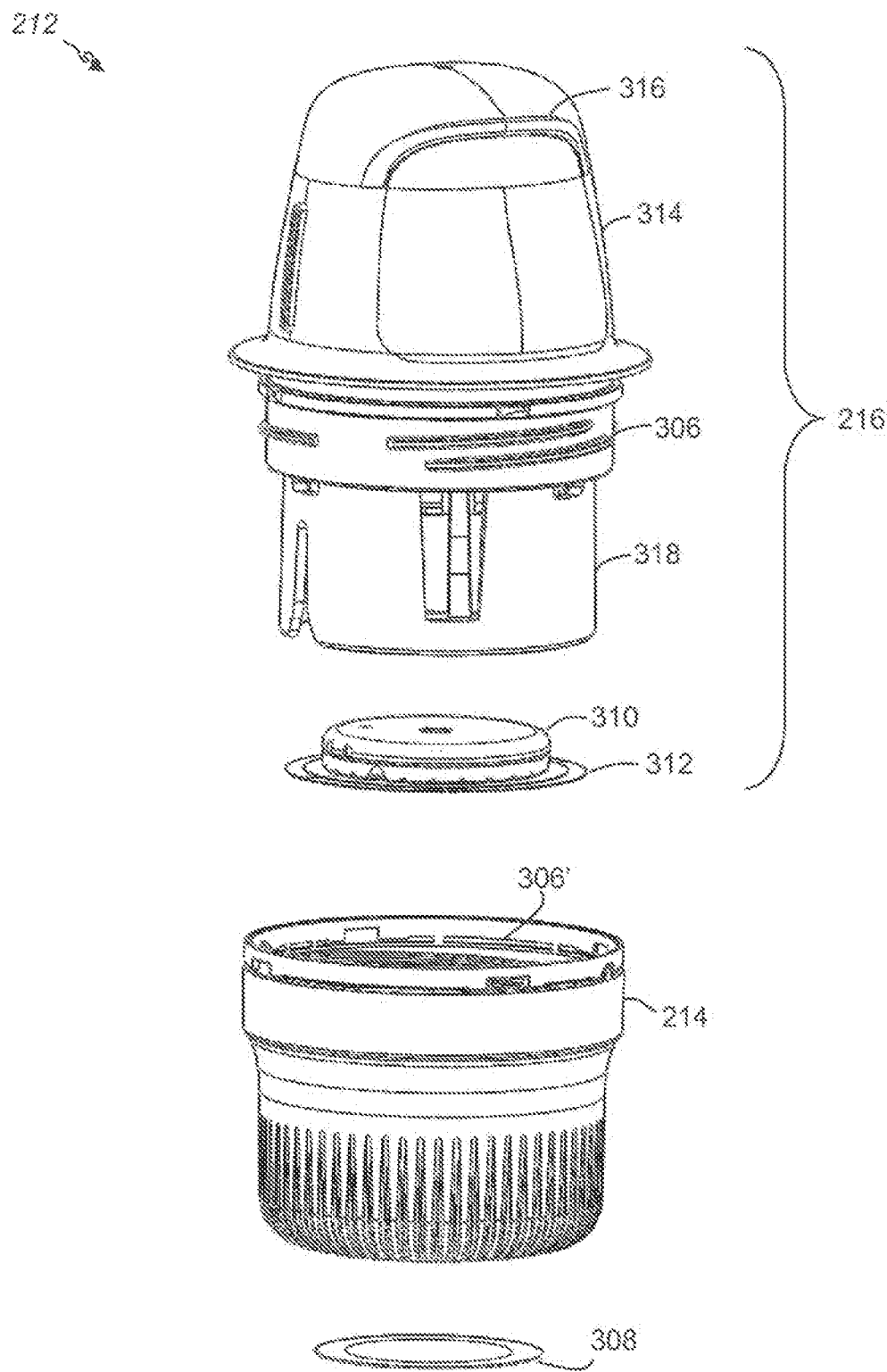
FIG. 3 is an assembly view of an applicator or inserter.
Figure 4:
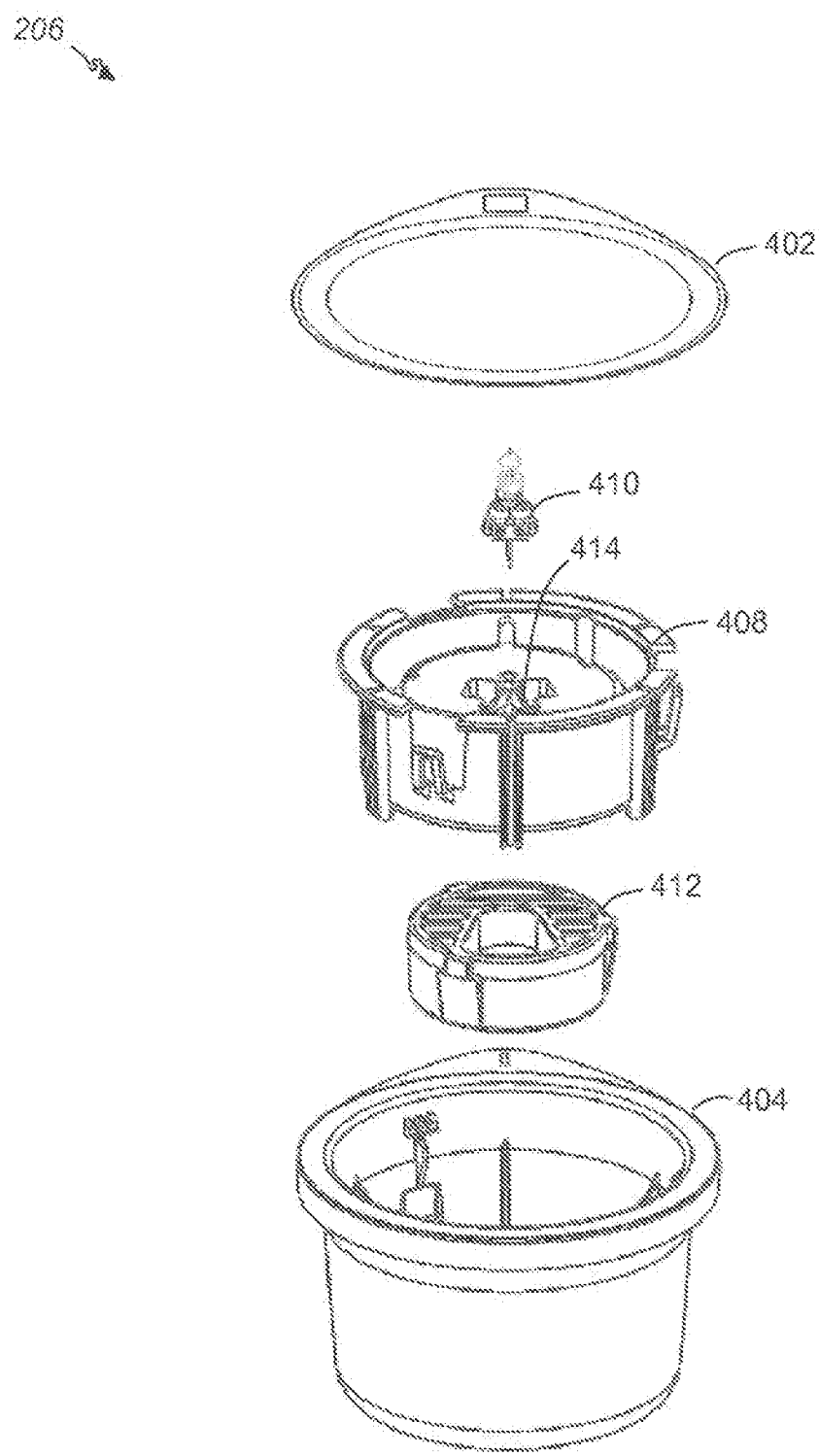
FIG. 4 is an assembly view of a sensor container or loader.

The applicator 212, container 206, and associated components shown in FIGS. 2A to 2G are illustrated in more detail in FIGS. 3 and 4. In addition, numerous other variations are described in detail below. These alternative embodiments may operate differently insofar as their internal workings, but may present no difference concerning user activity.

Turning to FIG. 3, applicator 212 includes a removable cap 214 and applicator assembly 216. The removable cap 214 can be secured to the applicator assembly 216 via complimentary threadings 306, 306'. End Cap 214 fits with the applicator 216 to create a sterile packaging for interior of the applicator 216. Therefore, no additional packaging is required to maintain sterility of the interior of the applicator 216. In some embodiments, the end (not visible) of the removable end cap 214 can include one or more openings, which can be sealed by a sterile barrier material such as DuPont™ Tyvek®, or other suitable material, to form seal 308. Such provision allows for ethylene oxide (ETO) sterilization of the applicator 212 through the seal 308 when closed. In some embodiments, the openings in the removable cap 214 may not be present and the removable cap 214 may be made from a sterile process-permeable material so that the interior of the applicator can be sterilized when the cap is mated to it, but that maintains sterility of the interior of the cap after exposure to the sterility process. In some embodiments, ETO sterilization is compatible with the electronics within the electronics assembly 310 and with the associated adhesive patch 312, both of which can be releasably retained within the applicator assembly 216 until applied to the user. As shown, the applicator assembly 216 includes a housing 314 including integrally formed grip features 316 and a translating sheath or guide sleeve 318.

In reference to FIG. 4, the container 206 includes a cover 402 (e.g., made of a removable material such as foil) and casing 404. Housed within the casing 404 is a desiccant body 412 and a table or platform 408. In some embodiments, the desiccant body 412 can have an annular shape so that the desiccant body 412 can be disposed within the casing 404 and a sensor assembly support (not visible in FIG. 4 but see 512 in FIGS. 5A and 5B) can extend up through the desiccant body 412. This arrangement allows the container 206 to include a desiccant without requiring any additional height to accommodate the desiccant. A sensor assembly 410 is snap-fit or otherwise held by the sensor assembly support 512. The sensor assembly 410 can also be snap-fit or otherwise held by the platform 408 (e.g., using fingers 414). With the cover 402 sealed, the container 206 can be subjected to gamma or radiation (e.g., e-beam) sterilization, an approach compatible with the chemistry of the sensor included in the sensor assembly 410. Like the applicator 212, the container 206 is its own sterile packaging so that no additional packaging, other than the casing 404 and the cover 402, is required to maintain sterility of the interior of the casing.

The container 206 and the applicator 212 may be sterilized by different sterilization approaches. For example, a sensor contained in a container 206 may require one type of sterilization process and the contents of an applicator 212—for example, electronics contained within the interior of the applicator 212—may require another type of sterilization process. The utility of a two-piece separable but combinable system (i.e., the container 206 and the applicator 212) enables the respective sterilization of the two pieces and sterility maintenance before the two are connected together for use. In other words, separately sealing the container 206 and the applicator 212 facilitates the use of otherwise incompatible sterilization methods for these two components. For example, one type of sterilization which could damage the chemistry of the sensor can be used to sterilize the applicator 212 including the electronics assembly 310 including the adhesive patch 312. Likewise, another sterilization process which could damage the electronics in the electronics assembly 310 (and/or the adhesive patch 312 used to adhere the electronics assembly 310 to the user's skin) can be used to sterilize the container 206 including the sensor therein. Still other advantages may exist, given different shelf-life attributes for the active (i.e., electronic, chemical, etc.) elements. In some embodiments, all components can be sterilized using the same sterilization technique, such as, but not limited to ETO and e-beam sterilization, etc.

In some embodiments, the platform 408 in the container 206 functions as an anti-tamper barrier for the sensor assembly 410 and prevents direct handling of the sensor assembly 410 by the user. More specifically, the platform 408 is disposed to protect and assist in the retention of the sensor, a sharp, and an associated connector. In some embodiments, the platform 408 is locked in place within the casing 404 until released by a longitudinally directed force from the applicator assembly 216 during the user assembly operation 106 (FIG. 1). In other words, as the guide sleeve 318 of the applicator assembly 216 is inserted down against the platform 408, the sleeve 318 releases a locking mechanism (e.g., a catch) and allows the platform to translate deeper into the casing 404. Additionally, features of the casing 404 can be employed to unlock a guide sleeve lock feature of the applicator assembly 216. In some embodiments, the platform 408 in the container 206 can only be unlocked if the guide sleeve 318 of the applicator assembly 216 is inserted into the container 206 with alignment marks on the applicator assembly 216 and the container 206 properly aligned. (See FIG. 10C and associated text below).

Figure 5A:
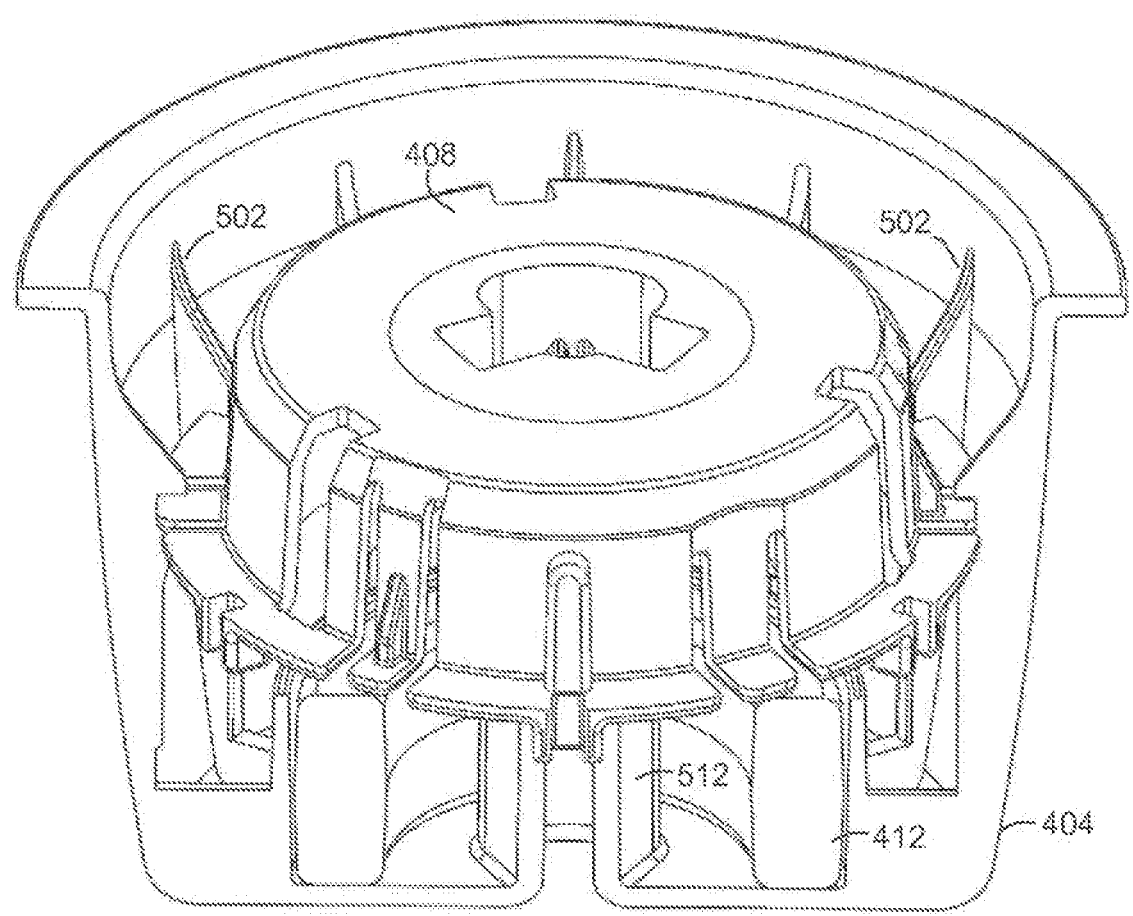
FIGS. 5A and 5B are section views of the container in FIG. 4.
Figure 5B:
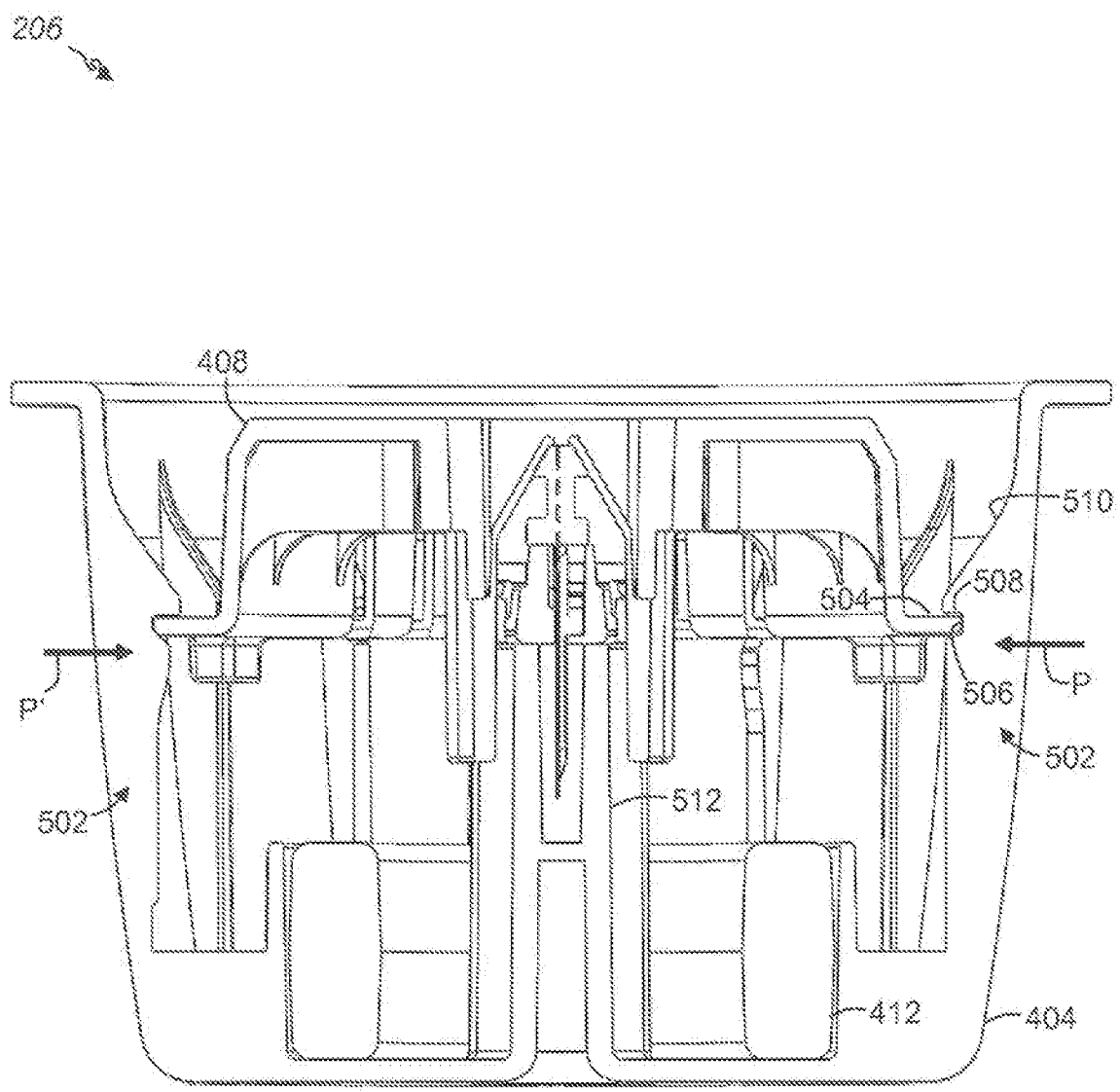

FIG. 5A is an isometric, cross-sectional view of the casing 404 of FIG. 4. FIG. 5B is an assembled, isometric, cross-sectional view of the container 206 of FIG. 4 including the component parts. As can be seen in FIGS. 5A and 5B, platform 408 is surrounded by multiple locking features 502 (at least one is advantageously provided in some embodiments). Each of locking features 502 includes a cantilevered arm 504 with a tongue 506 received in a slot or groove 508. So disposed, the platform 408 is locked in place. When the arm(s) 504 are urged inward, in the direction represented by arrows P and P', from a concentrically disposed sleeve 318 (not shown) of the applicator assembly 216 riding over ramp(s) 510, the locking feature(s) 502 are released and the platform 408 can translate in direction B along a longitudinal axis of the combined applicator assembly 216 interfaced with the container 206. The translation of the platform 408 into the casing 404 provides access to sensor assembly 410 by the applicator assembly 216. Until the platform 408 is unlocked and driven down into the casing 404, the sensor assembly 410 is otherwise isolated from being touched or otherwise handled/accessed by a user. In some embodiments, additional detent ramp features can be provided to hold the platform 408 until depressed with force applied by a user. In addition, various key-and-way or slot-and-groove guidance features can be provided to control such motion and ensure that it is smooth and linear (i.e., to avoid platform canting, binding, etc.)

In some embodiments, the sleeve/ramp interface with associated locks relies only on detent features to maintain the platform's position. So configured, inadvertent handling of the sensor assembly can be avoided. The detent(s) can be tuned to require deliberate action to clear the platform 408.

Figure 6:
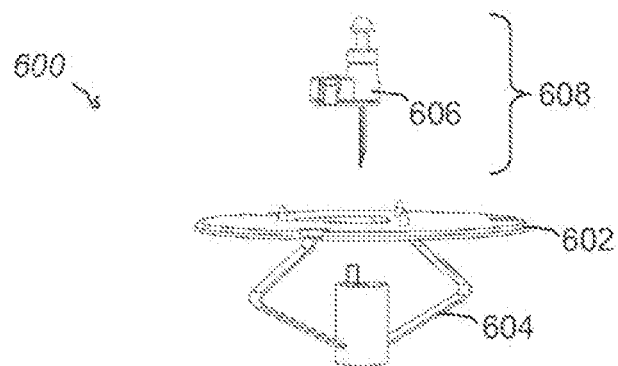
FIG. 6 is an assembly view of an alternative container.
Figure 6:
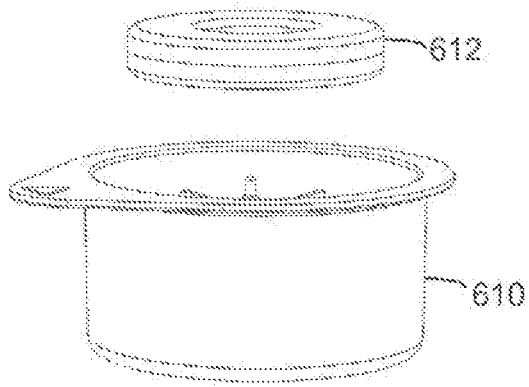
Figure 7:
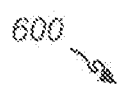
FIG. 7 is a section view of the assembly of FIG. 6.
Figure 7:
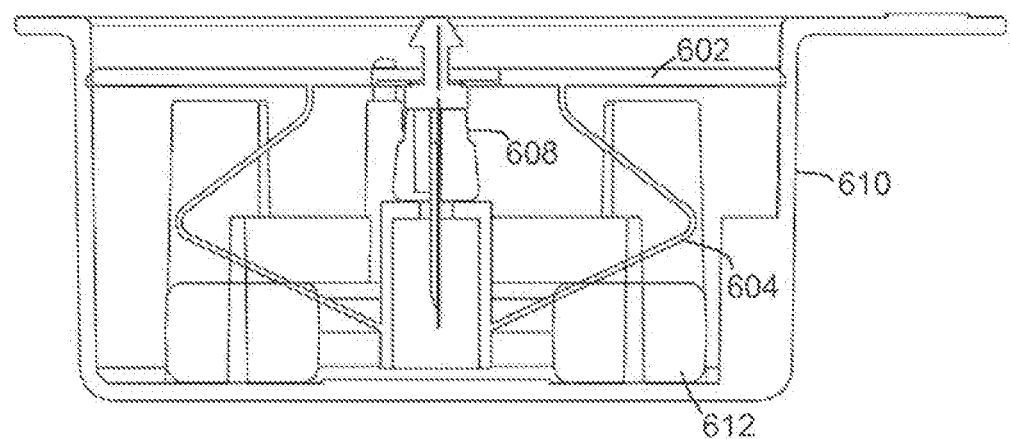

In some embodiments, alternative mechanisms and arrangements may be employed to provide a platform 408 that collapses upon application of force via the applicator assembly 216 by the user. For example, FIGS. 6 and 7 depict an alternative container 600 embodiment including an alternative platform 602 arrangement. Here, a collapsible armature or linkage 604 supports the platform 602. This linkage 604 is integrally guided and spring-loaded by virtue of the living hinge design of the linkage 604. Alternatively, a coil spring could be employed along with guides for the platform 602. A sleeve 318 (FIG. 3) (FIG. 3) of an applicator 216 or the base of sensor mount unit 606 itself, can be used to translate the platform 602 to provide clearance for sensor assembly 608 access and pick-up by the applicator 216 and incorporation as a complete assembled on-body device 222. The container 600 includes a casing 610 and can also include a desiccant ring 612 to protect the sensor assembly 608 from moisture.

Figure 8:
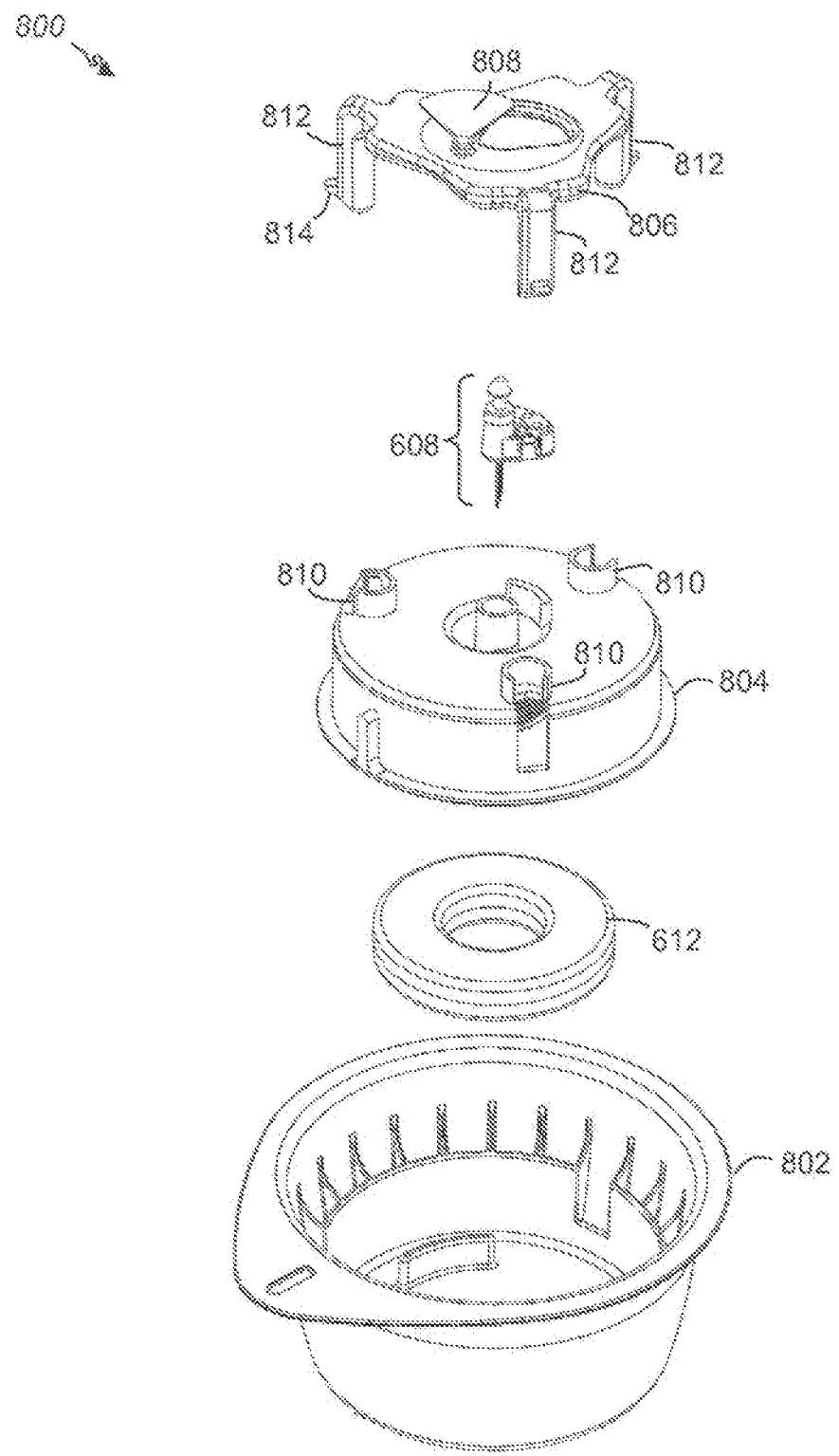
FIG. 8 is an assembly view of yet another sensor container set or loader.
Figure 9A:
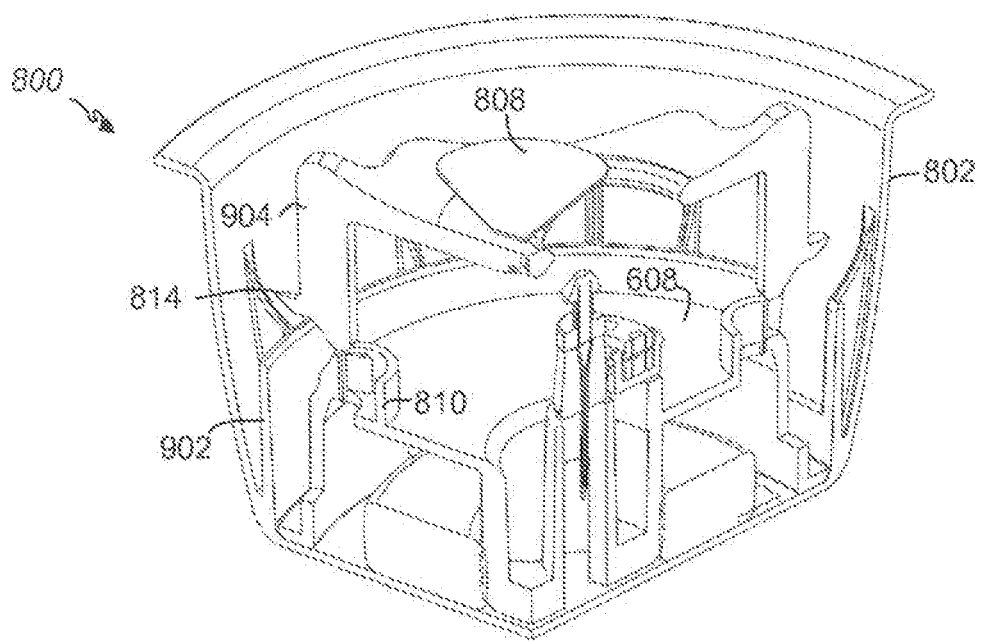
FIGS. 9A and 9B are top and section views, respectively, of the container set assembly of FIG. 8 in stages of operation.
Figure 9B:
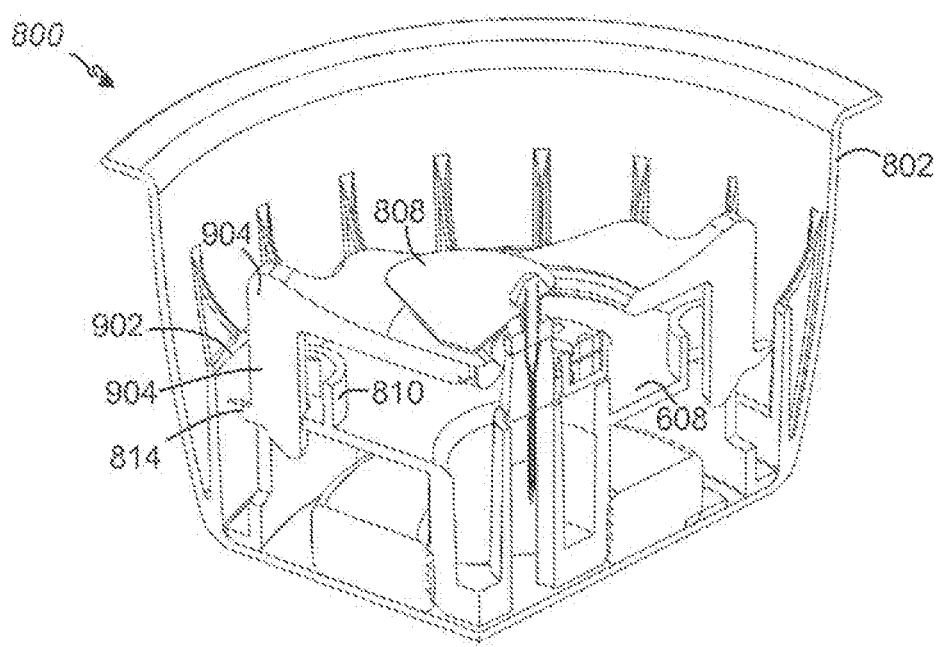

Another embodiment for sensor storage and protection is illustrated in FIG. 8 with container 800. As with the prior embodiments, this embodiment can also include an annular desiccant ring 612. Casing 802 is provided in connection with a support base 804. The support base 804 receives sensor assembly 608 and a frame 806. The frame 806 includes a pivoting door 808. As shown, the support base 804 incorporates three channels 810 for receipt of frame legs 812 to serve as guidance. In its up/closed position shown in FIG. 9A, door 808 protects the sensor assembly 608 from contact by the user. Spiral ramp features interacting between the support base 804 and the frame 806 cause the door 808 to swing open as the frame 806 is moved down as shown in FIG. 9B. Likewise, features of the frame 806 can hold the sensor assembly 608 against the support base 804 until the frame 806 is pushed down by user activity.

Similar to the container embodiment 206 shown in FIGS. 5A and 5B, the frame 806 in container 800 can be locked in place and released by applicator sleeve introduction. A support ring 902 may lock against boss or tang 814 until the boss 814 is urged inward by the action of an applicator sleeve along angled interface surface 904 of each leg 812. In some embodiments, the legs 812 can be biased outward with a preload but in other embodiments, the locking/unlocking function can operate without such biasing. FIG. 9A illustrates the locked configuration, whereas FIG. 9B illustrates unlocked/translated relation of components.

Figure 10A:
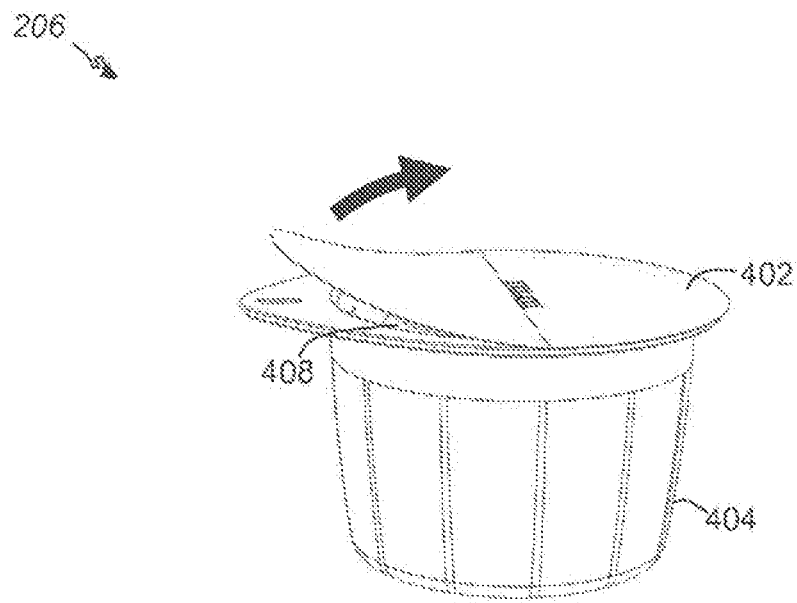
FIGS. 10A-10N variously illustrate the mechanics of preparing the applicator for use.
Figure 10B:
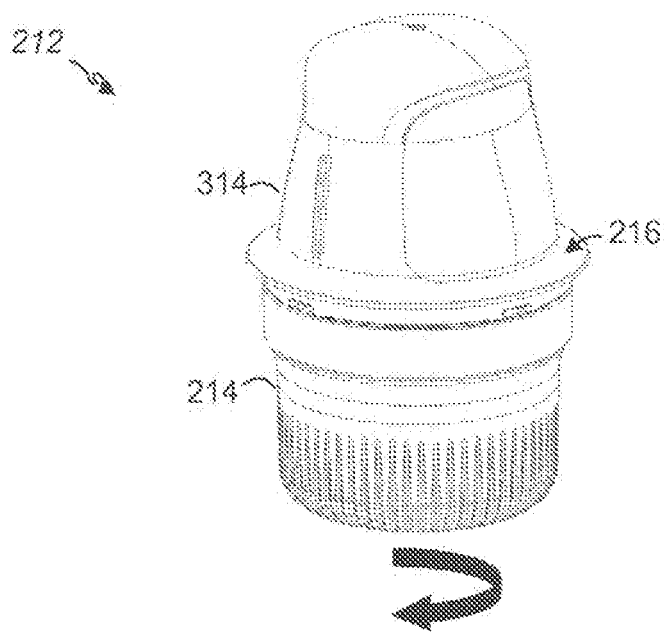
Figure 10C:
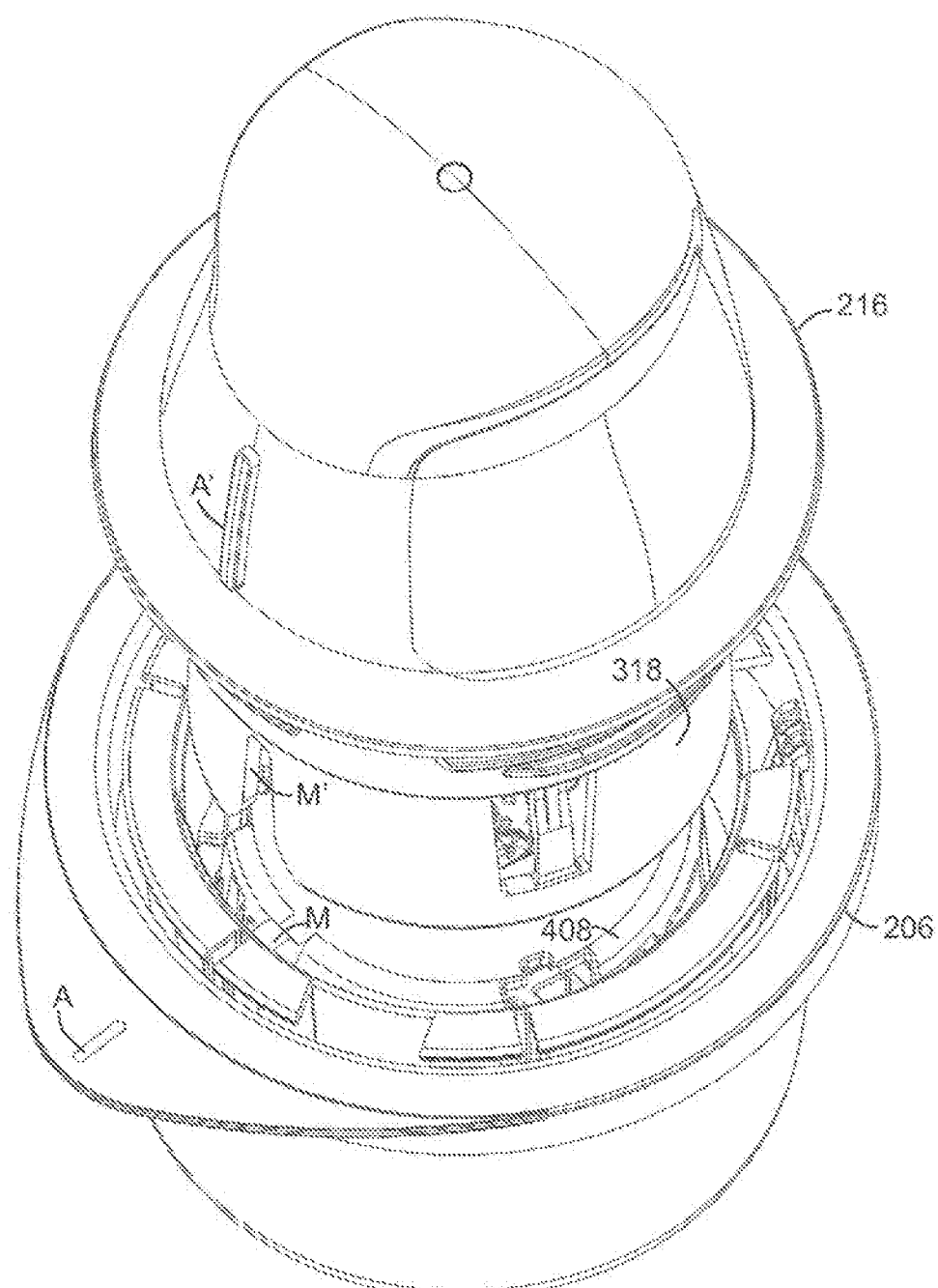
Figure 10D:
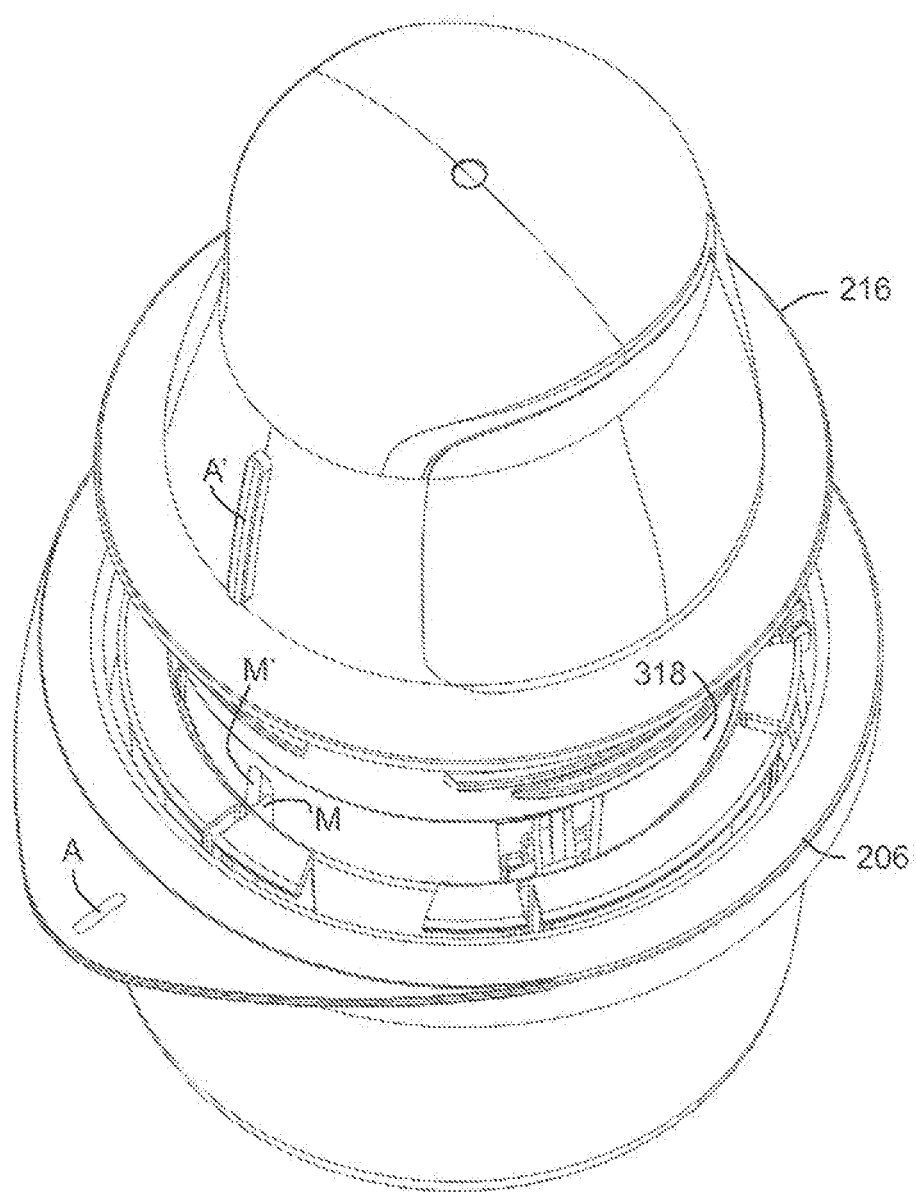
Figure 10E:
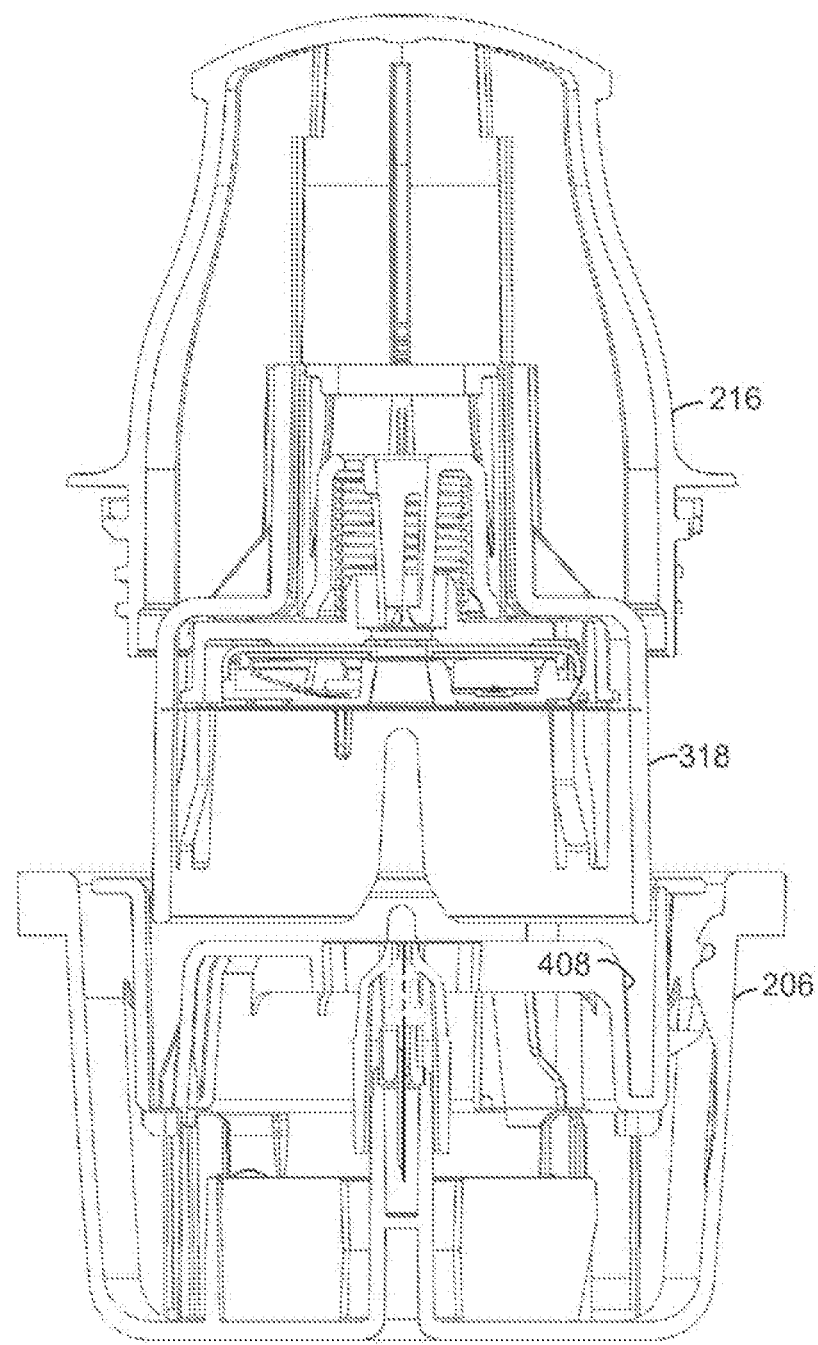
Figure 10F:
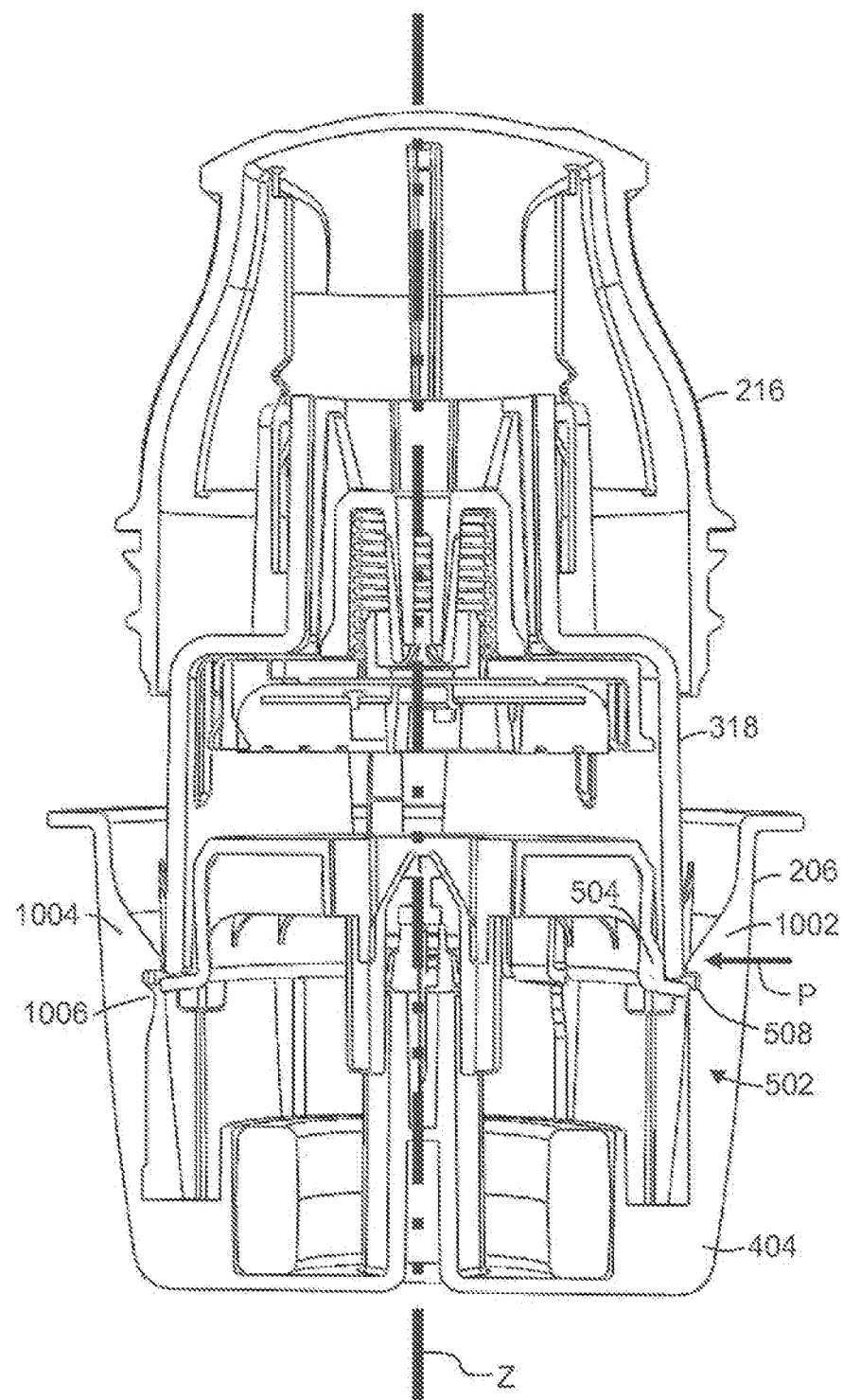
Figure 10G:
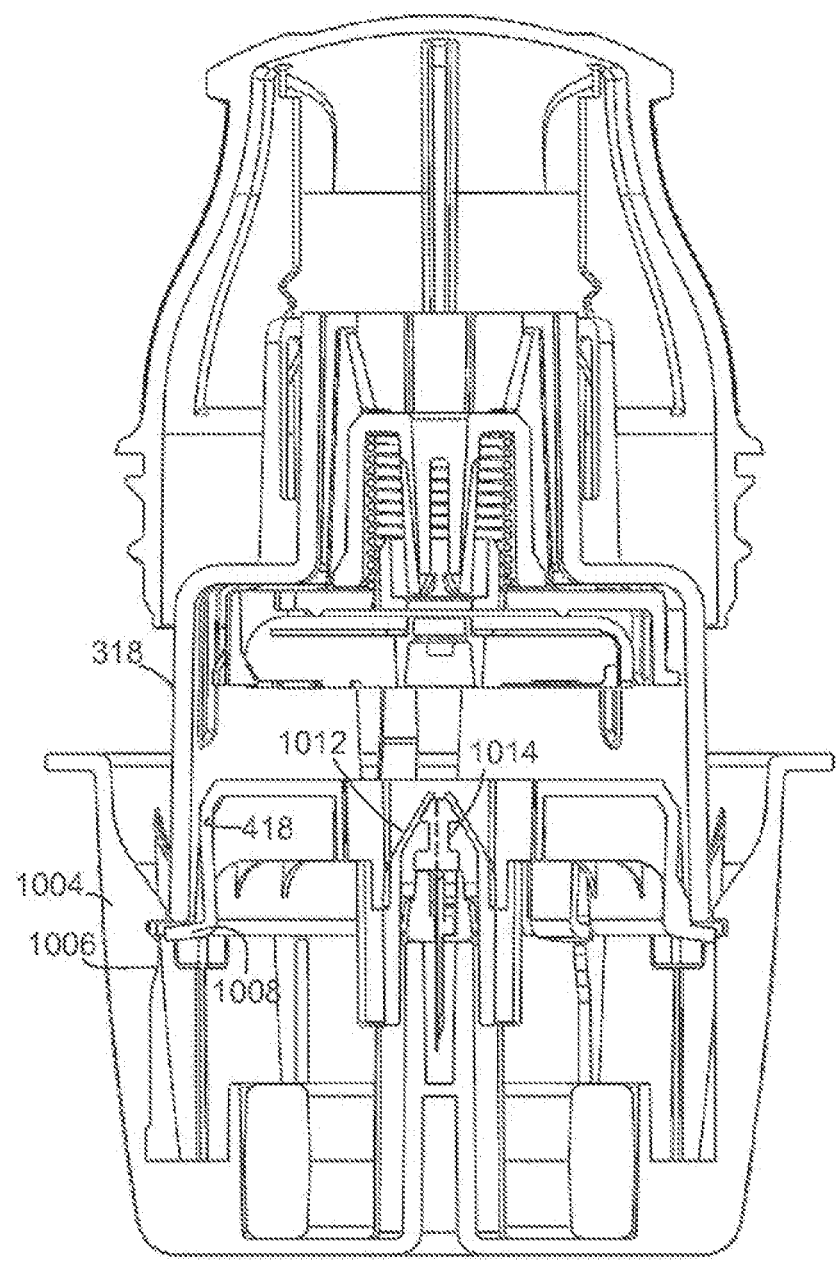
Figure 10H:
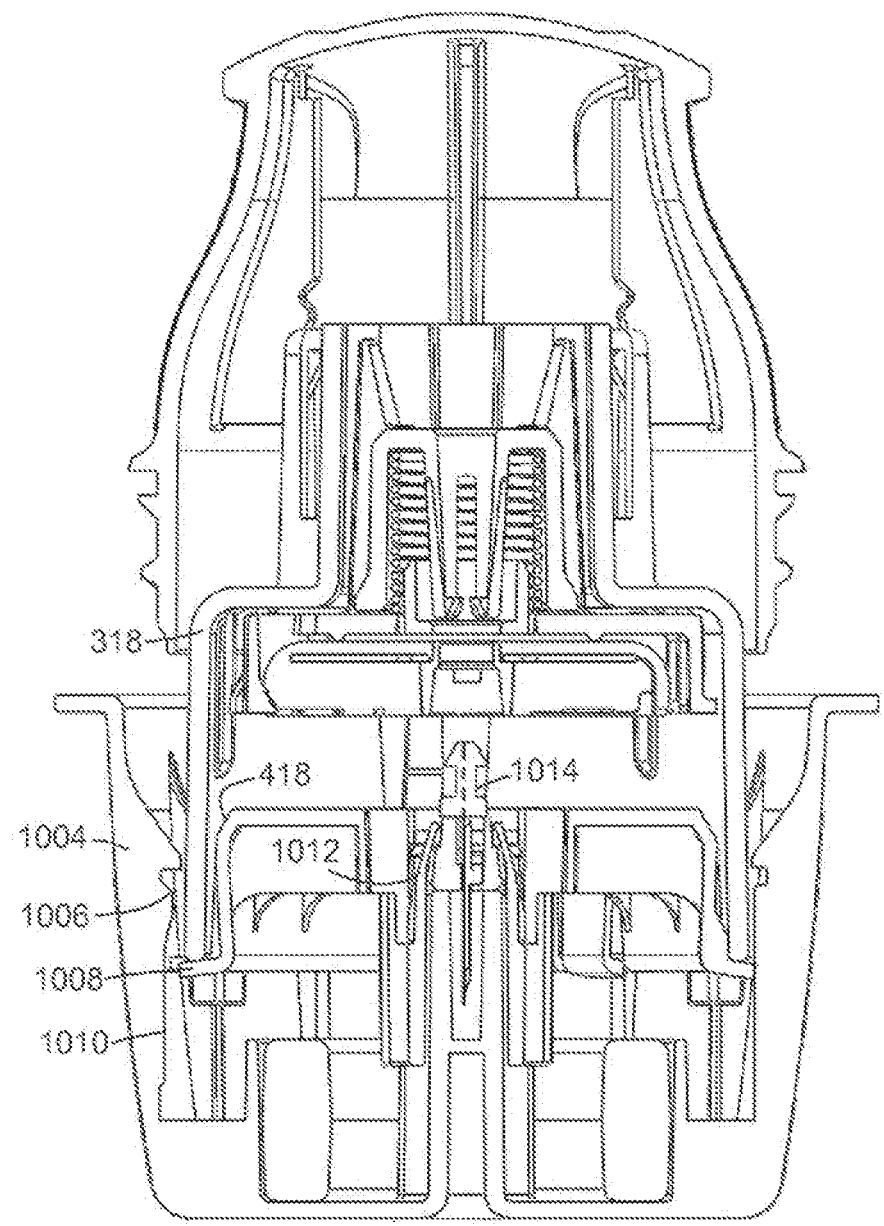
Figure 10I:
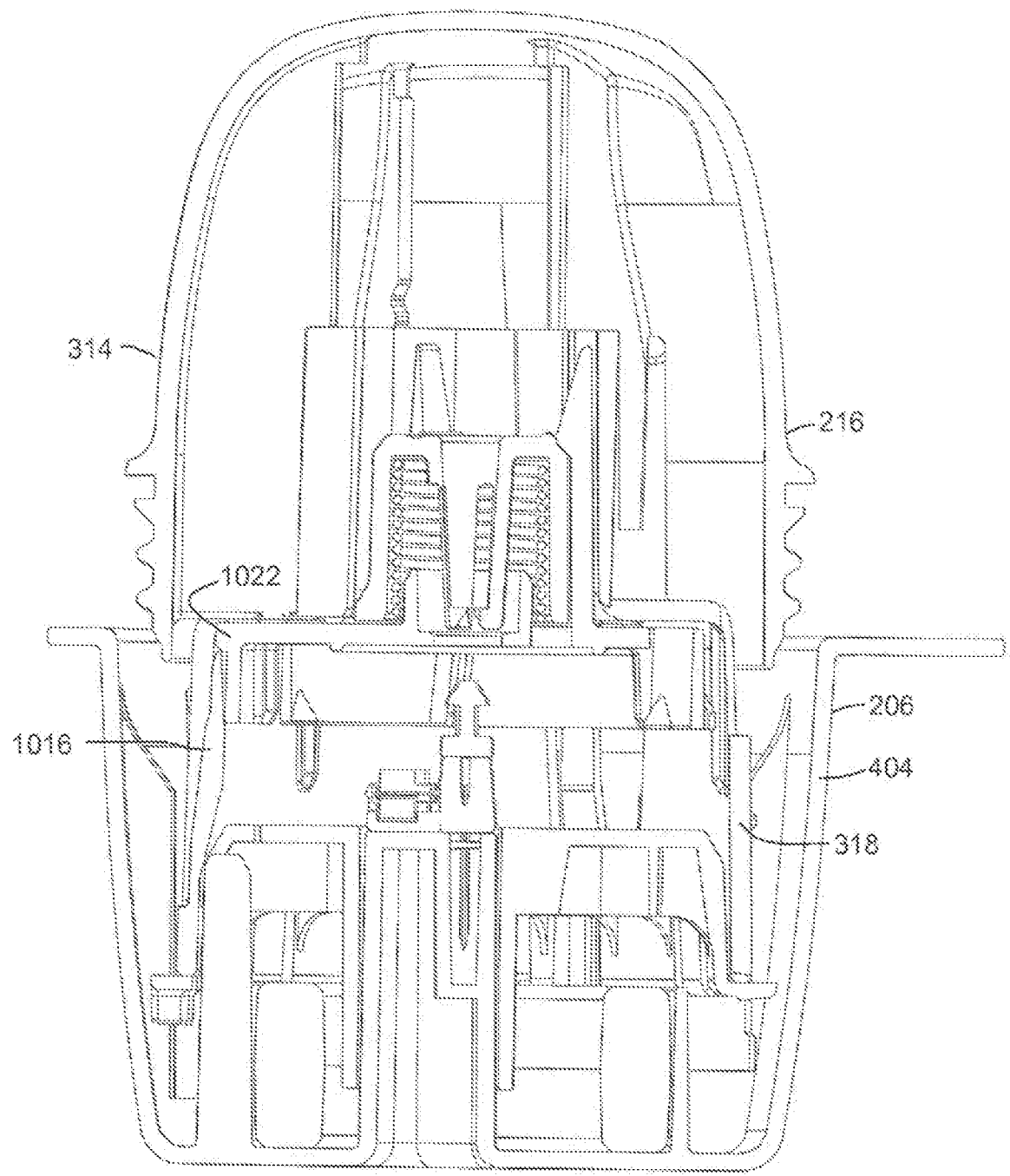
Figure 10J:
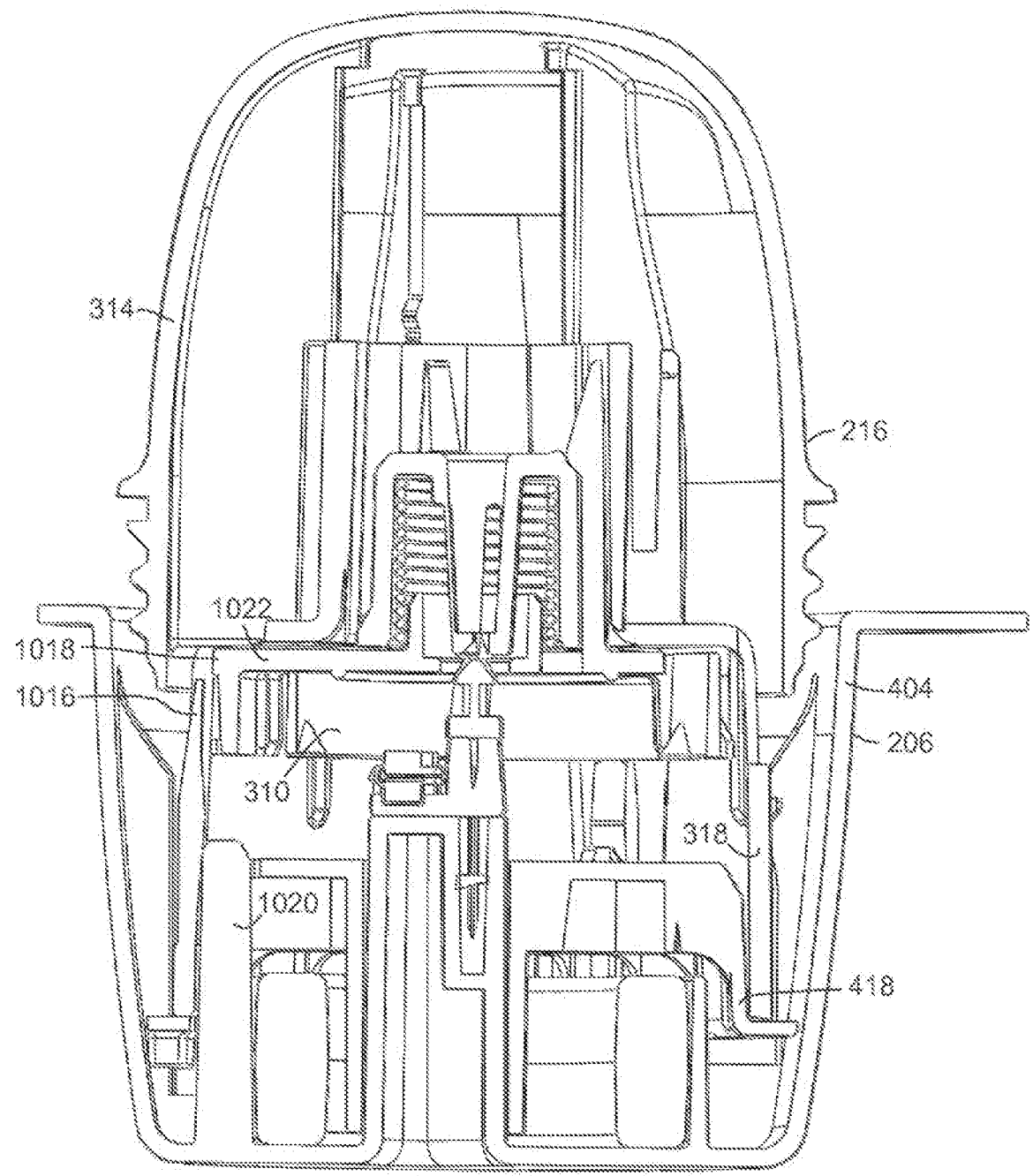
Figure 10K:
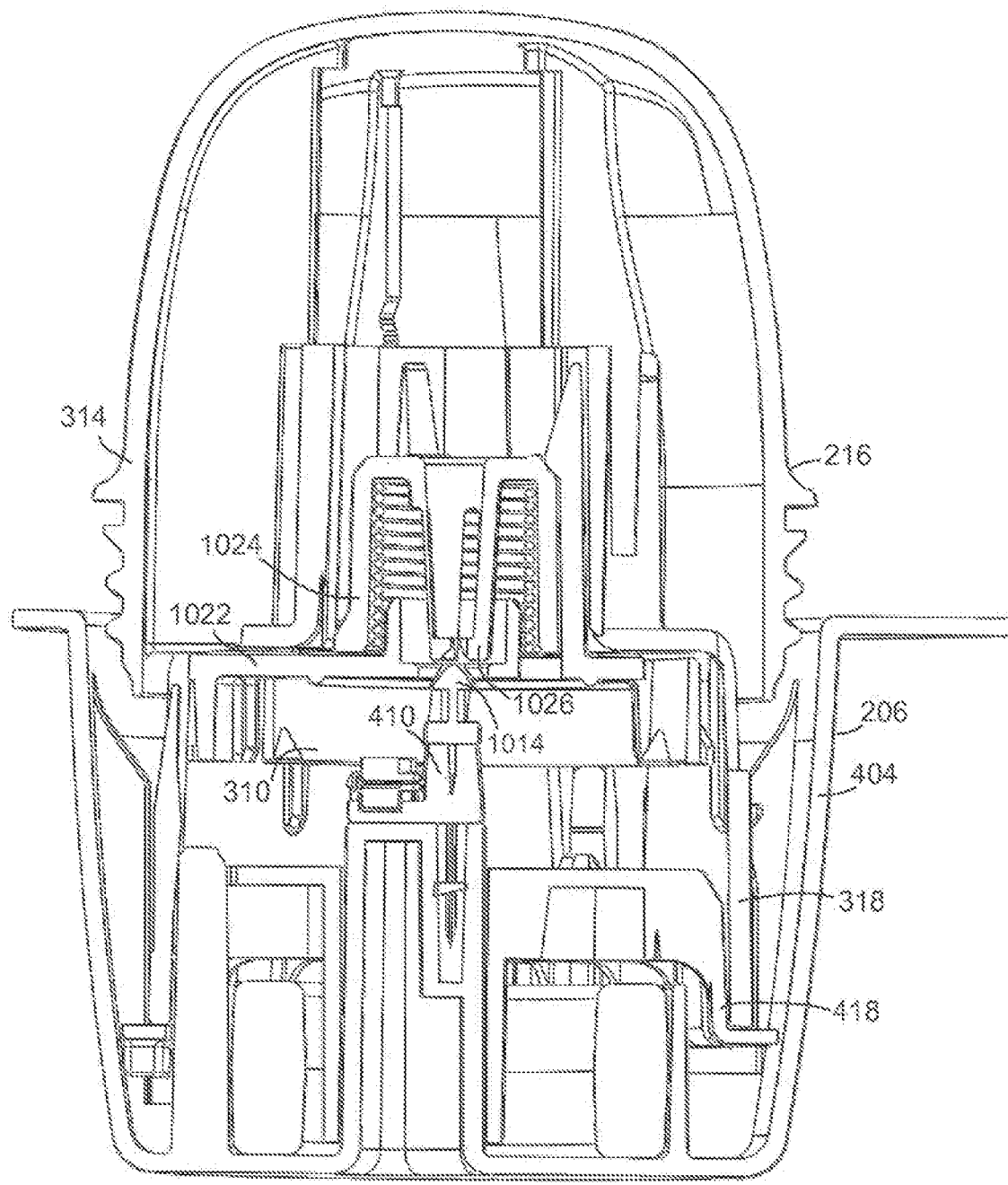
Figure 10L:
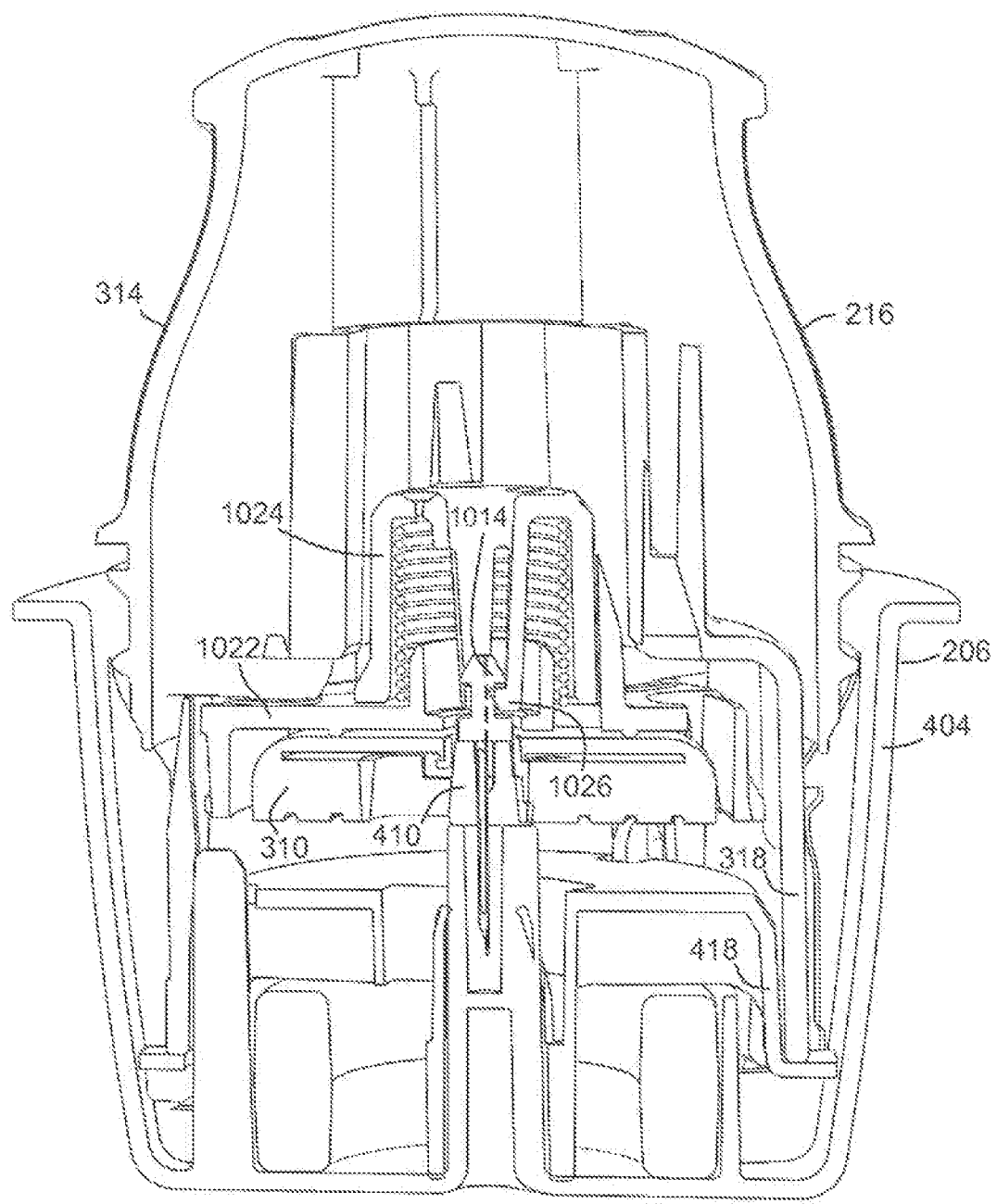
Figure 10M:
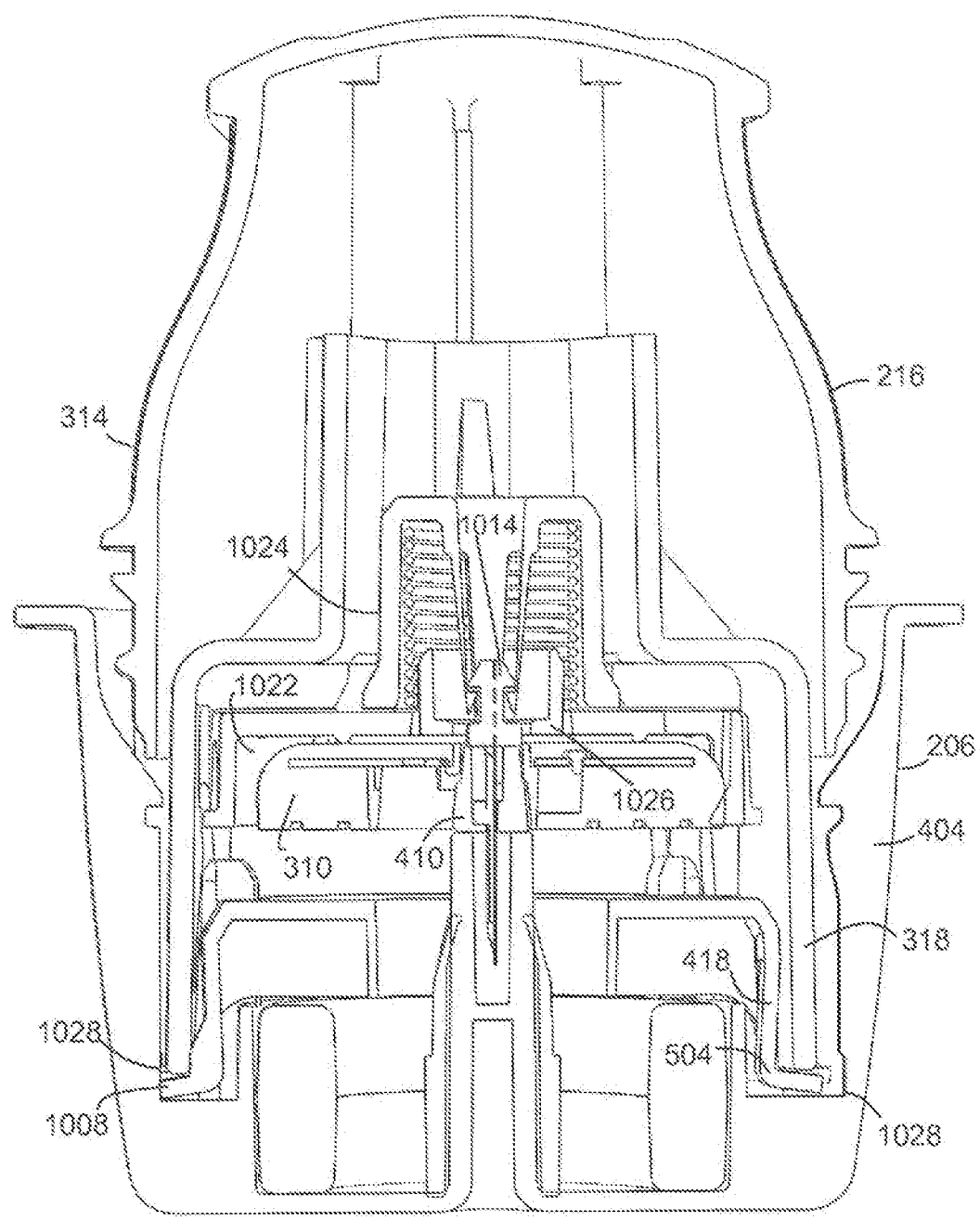
Figure 10N:
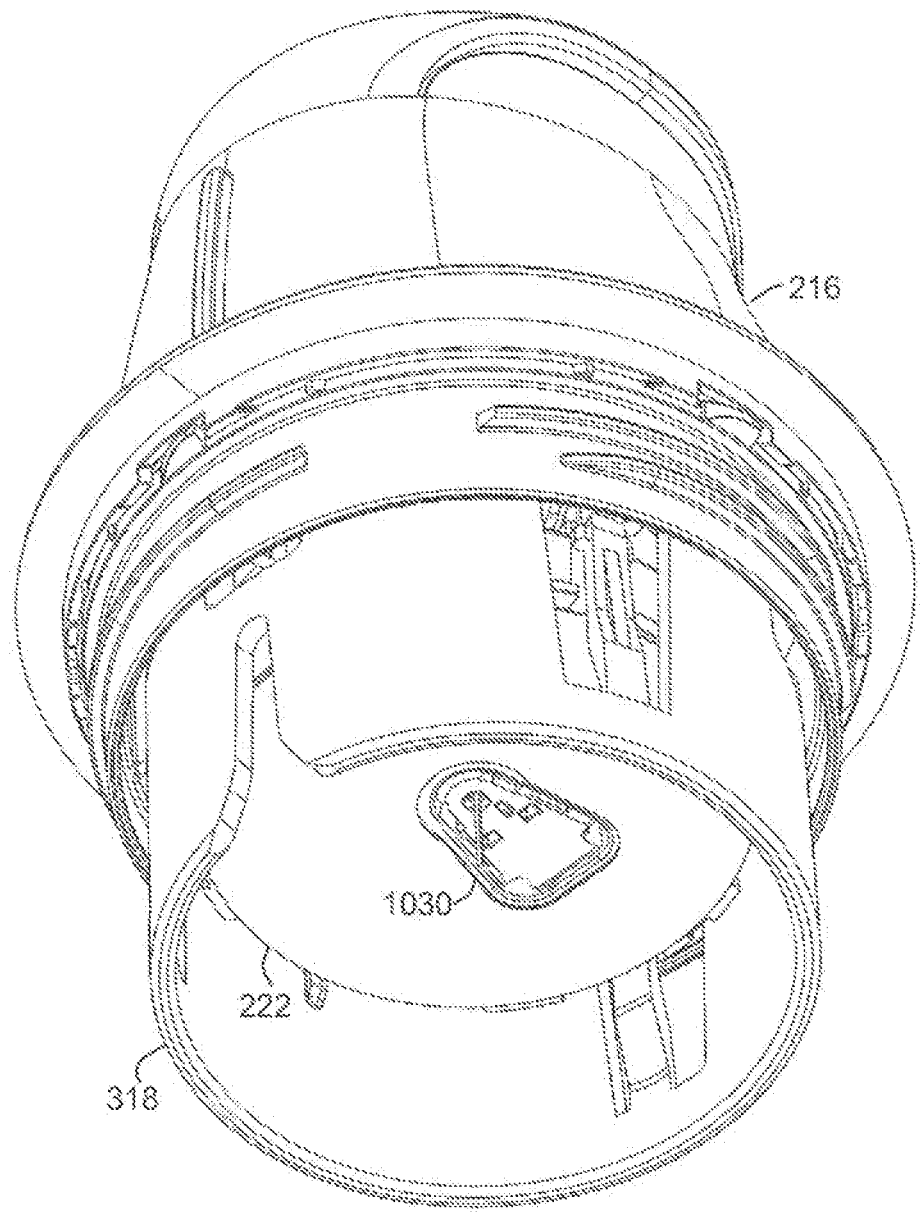

FIGS. 10A to 10N illustrate example details of embodiments of the internal device mechanics of preparing the applicator 212 for use, using the container 206. All together, these drawings represent an example sequence of assembling an on-body device 222 by connecting a sensor assembly 410 stored in the container 206 with an electronics assembly 310 stored in the applicator 212. In addition, the sequence prepares the applicator 212 to apply the assembled on-body device 222 to the user. Modification of such activity for use with the alternative container embodiments (as described above or others) can be appreciated in reference to the same by those with skill in the art.

FIGS. 10A and 10B show container 206 and applicator 212 with their constituent parts, along with arrows indicating the manner of cover 402 and cap 214 removal, respectively. Upon peeling off foil cover 402 from the casing 404, the platform 408 within is locked, thus protecting the sensor assembly 410 (not visible but see FIG. 4) which includes a sensor, a sensor support (also referred to as a plug), a connector, and a sharp. (These components are discussed in detail below.) Likewise, upon removal of cap 214 from the applicator assembly 216, the applicator 212 is locked. As a result of being locked, a guide sleeve 318 (not visible but see FIG. 3) cannot be collapsed into the applicator's housing 314.

In FIG. 10C, applicator assembly 216 is set within container 206. The two components 206, 216 are rotated and advanced until mechanical alignment features M and M' engage, allowing the applicator assembly 216 to register and sit level within the container 206. Visual alignment indicators A and A' assist or guide the user to quickly find the proper alignment position. Note that in some embodiments, the platform 408 cannot be unlocked to translate into the container 206 unless the alignment features M and M' are properly aligned. FIG. 10D depicts the components 206, 216 with the mechanical alignment features M, M' engaged. Sleeve 318 passes over platform 408, with the platform 408 nested concentrically inside the inner diameter of sleeve 318.

Cross-sectional views FIGS. 10E and 10F illustrate the relationship of parts overviewed in FIGS. 10C and 10D. When the sleeve 318 of applicator assembly 216 is seated onto the platform 408 of the container 206 and pushed downward, platform locking features 502 disposed around the platform 408 on locking ribs 1002 are unlocked to allow the platform 408 to translate along a longitudinal axis (labeled "Z") of the interfaced components 206, 216. More specifically, a portion of platform 408 bends and platform locking arms 504 are displaced inward as indicated by arrow P to clear locking grooves 508 in the locking ribs 1002 of casing 404, thus unlocking the platform 408. At this point, the platform 408 is held in place by guide ribs 1004 each providing a detent feature 1006 between the platform 408 and the guide ribs 1004 that can be overcome by further downward pressure applied by the user upon further depression of the applicator assembly 216 in the direction of the longitudinal axis Z.

Turning now to FIGS. 10G and 10H, the dropping of the unlocked platform 418 is illustrated. FIG. 10G depicts further depression of the applicator assembly 216 in the direction of the longitudinal axis Z. The force from the sleeve 318 causes inward, radial deflection of a portion of the platform 408. The effect is that detent arms 1008 are flexed down, inward and away from the detent feature 1006 of guide ribs 1004 as shown. This action releases the platform 418 and the applicator assembly 216 into freefall into the container 206. In some embodiments, the force to flex detent arms 1008, or in other words, the force to overcome the resistance from the detent features 1006, is selected to create a predetermined amount of momentum sufficient to ultimately properly mate the electronics assembly 310 with the sensor assembly 410 and unlock the sleeve 318. In some embodiments, the force to overcome the resistance from the detent features 1006 is from approximately 1 N to approximately 23 N. Other practicable values are possible.

In FIG. 10H, once detent arms 1008 of the platform 418 are past the detent features 1006, a relieve or undercut 1010 in each of the guide ribs 1004 provides increased clearance for the platform 418 to reduce sliding friction as the sleeve 318 and platform 418 slide or telescope further into the container's casing 404 along the longitudinal axis Z (FIG. 10F). Also, one or more flexible grasping arms 1012 previously in contact with the sensor assembly 410, particularly through sharp boss 1014, are moved from a stabilizing configuration in FIG. 10G to a freed state or configuration in FIG. 10H. In other words, as the platform 418 translates further into the container 206, the sharp boss 1014 of the sensor assembly 410 protrudes through a central opening in the platform 418 and pushes the flexible grasping arms 1012 out of the way.

Turning now to FIGS. 10I and 10J, a cross-sectional view depicting a slightly different cut plane than the prior views is provided to illustrate additional features. In FIG. 10I, sleeve lock arms are shown engaged with a sleeve lock ledge 1018. This engagement locks the applicator assembly 216 and prevents the sleeve 318 from being able to be retracted or pushed into the housing 314 of the applicator assembly 216. In FIG. 10J, as the applicator assembly 216 is further advanced into the container 206 along the longitudinal axis Z (FIG. 10F), sleeve unlock features contact and bend the sleeve lock arms 1016 clear of the sleeve lock ledge 1018 thereby unlocking the applicator assembly 216. Note that in the particular example embodiment depicted in FIGS. 10I and 10J, the sleeve lock ledge 1018 is formed in a carrier 1022 of the electronics assembly 310.

When the platform 418 bottoms-out in the container 206 as shown in FIG. 10J, the sleeve 318 of the applicator assembly 216 is fully unlocked/released and ready to move. Note that while the sleeve lock arms 1016 are shown flexing outward to unlock, in some embodiments, the sleeve lock arms 1016 can be oriented to flex radially inward to free the elements. The same may hold true for the various locking/unlocking features of the present invention. However, the present arrangement offers advantages in terms of a coordinated whole providing an advantageous form factor and minimized container casing size (a factor that affects the user experience) in which the carrier 1022 of the electronics assembly 310 is coaxially arranged. Regarding the carrier 1022, it is advantageously designed with unique carrier arm features as detailed in, for example, U.S. patent application Ser. No. 13/071,461, the disclosure of which is incorporated herein by reference.

In FIGS. 10K and 10L, now that the sleeve 318 of the applicator assembly 216 is fully unlocked, the momentum along the longitudinal axis Z (FIG. 10F) from the force used to overcome the resistance of the detent features 1006 (FIG. 10H) causes three additional concurrent actions. First, even though the sleeve 318 cannot descend any further into the container 206 (since it is in contact with the platform 418 which is bottomed-out), the housing 314 of the applicator assembly 216, the carrier 1022, and the electronics assembly 310 are free to continue to descend into the container 206, now that the sleeve 318 is unlocked as shown in FIG. 10L.

Second, as the electronics assembly 310 descends further along the longitudinal axis Z (FIG. 10F), the sensor assembly 410 is forced into an opening in the electronics assembly 310 which couples the sensor to the electronics and completes assembly of the on-body device 222 (FIG. 2F). In some embodiments, mating snap features on the sensor assembly 410 and the electronics assembly 310 can be used to compel the components to remain locked and compressed together to insure a sealed, reliable connection. As an alternative to mating snap features, in some embodiments, the sensor assembly 410 and the electronics assembly 310 may be coupled by a light press fit or other connection method. However, the positive interaction and lock of snap features is an advantage. So too is the minimal force used to deflect fine locking features that spring back for engagement.

Third, along with the housing 314, the carrier 1022, and the electronics assembly 310, a sharp retraction assembly 1024 also continues to descend into the container 206 along the longitudinal axis Z (FIG. 10F) and is forced to receive the sharp boss 1014 of the sensor assembly 410. The conical head of the sharp boss 1014 is pushed past a radial arrangement of flexible arms 1026 of the sharp retraction assembly 1024. The flexible arms 1026 bend outwardly, as they are forced to ride against the passing conical surface of the head of the sharp boss 1014. The sharp is thus thereby engaged by the sharp retraction assembly 1024 as the flexible arms 1026 snap back into place once the head of the sharp boss 1014 has passed by, securely grasping the head at the narrowed neck portion of the sharp boss 1014. Note that a base of the sharp boss 1014 may be included to limit insertion into the sharp retraction assembly 1024 through interference with a stop limit or shoulder of the flexible arms 1026. FIG. 10K illustrates the arrangement immediately before the above three actions have completed and FIG. 10L illustrates the resulting arrangement immediately after the actions have completed.

In some embodiments, the connection features between the sharp boss 1014 of the sensor assembly 410 and the sharp retraction assembly 1024 can be otherwise configured. For example, the sharp retraction assembly 1024 can include a conical channel formed from a radial arrangement of inwardly biased flexible finger members configured to receive the head of sharp boss 1014 such that once the head has passed through the channel, the flexible fingers conform to the narrowed neck of the sharp boss 1014. With the fingers so conformed, the sharp boss 1014 is captured by the sharp retraction assembly 1024. Retention force is limited only by material strength because the self-energizing lock is not prone to slip between the pieces.

Turning to FIG. 10M, a slightly rotated view, relative to FIG. 10L, is shown. When the sharp boss 1014 is engaged in the sharp retraction assembly 1024, the sensor assembly 410 is coupled to the electronics assembly 310 completing assembly of the on-body-device 222, and the sleeve 318 is unlocked, platform locking arms 504 and detent arms 1008 have engaged undercut grooves 1028 in the container 206, thereby locking the platform 418 in the casing 404. This engagement between the platform 418 and the casing 404 marks the final position of the container 206 from which the loaded applicator assembly 216 is withdrawn for use to apply the on-body device 222 to the user.

Now, once removed from the container 206, the applicator assembly 216 is ready to "fire" as illustrated in FIG. 10N. As such, the applicator assembly 216 is ready to use as in application 108 described in connection with FIG. 2E. Here, the applicator assembly 216 has already been unlocked by interaction with the container 206, and the sensor assembly 410 is coupled to the electronics assembly 310. The sharp 1030 extends from the on-body device 222 which is held in the sleeve 318 of the applicator assembly 216 as shown.

FIGS. 11A to 11F illustrate example details of embodiments of the internal device mechanics of "firing" the applicator assembly 216 to apply the on-body device 222 to a user and including retracting the sharp 1030 safely back into the used applicator assembly 216. All together, these drawings represent an example sequence of driving the sharp 1030 (supporting a sensor coupled to the on-body device 222) into the skin of a user, withdrawing the sharp while leaving the sensor behind in operative contact with interstitial fluid of the user, and adhering the on-body device to the skin of the user with an adhesive. Modification of such activity for use with the alternative applicator assembly embodiments and components can be appreciated in reference to the same by those with skill in the art.

Figure 11A:
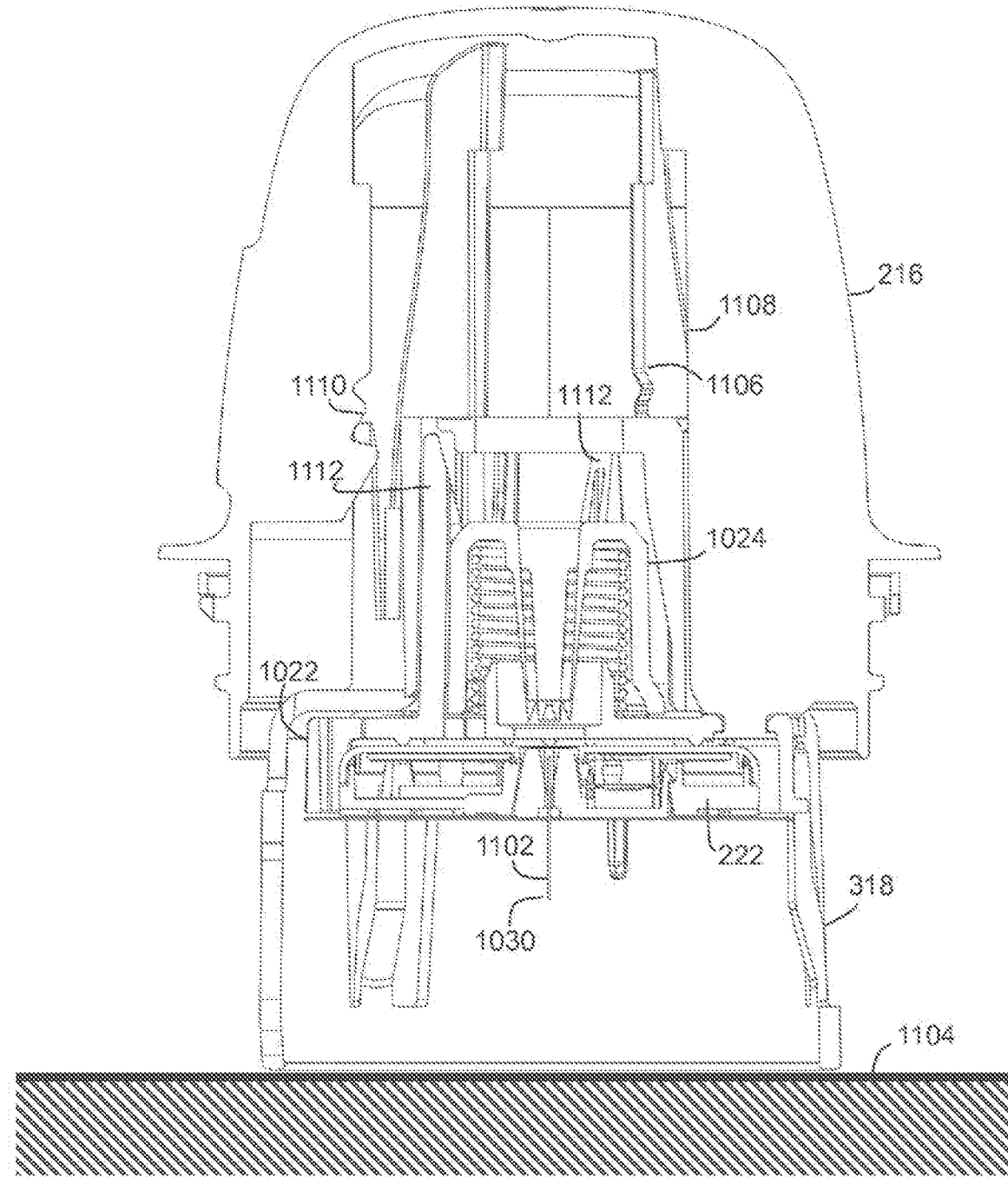
FIGS. 11A-11F illustrate the mechanics of applicator use.

Turning now to FIG. 11A, a sensor 1102 is supported within sharp 1030, just above the skin 1104 of the user. Rails 1106 (optionally three of them) of an upper guide section 1108 may be provided to control applicator assembly 216 motion relative to the sleeve 318. The sleeve 318 is held by detent features 1110 within the applicator assembly 216 such that appropriate downward force along the longitudinal axis of the applicator assembly 216 will cause the resistance provided by the detent features 1110 to be overcome so that the sharp 1030 and on-body device 222 can translate along the longitudinal axis into (and onto) the skin 1104 of the user. In addition, catch arms 1112 of carrier 1022 engage the sharp retraction assembly 1024 to maintain the sharp 1030 in a position relative to the on-body device 222.

Figure 11B:
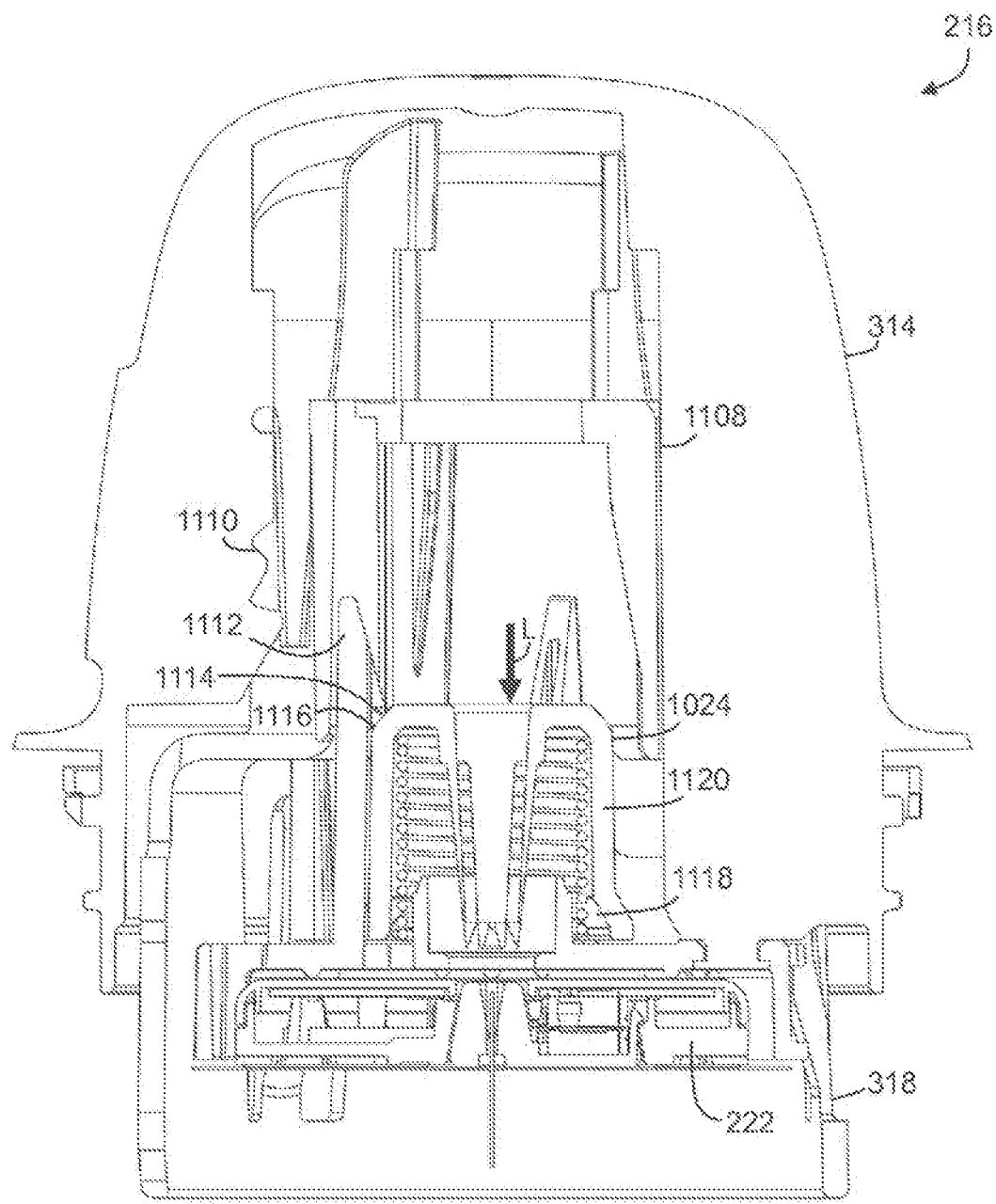

In FIG. 11B, user force is applied to overcome or override detent features 1110 and sleeve 318 collapses into housing 314 driving the on-body device 222 (with associated parts) to translate down as indicated by the arrow L along the longitudinal axis. An inner diameter of the upper guide section 1108 of the sleeve 318 constrains the position of carrier arms 1112 through the full stroke of the sensor/sharp insertion process. The retention of the stop surfaces 1114 of carrier arms 1112 against the complimentary faces 1116 of the sharp retraction assembly 1024 maintains the position of the members with return spring 1118 fully energized.

Figure 11C:
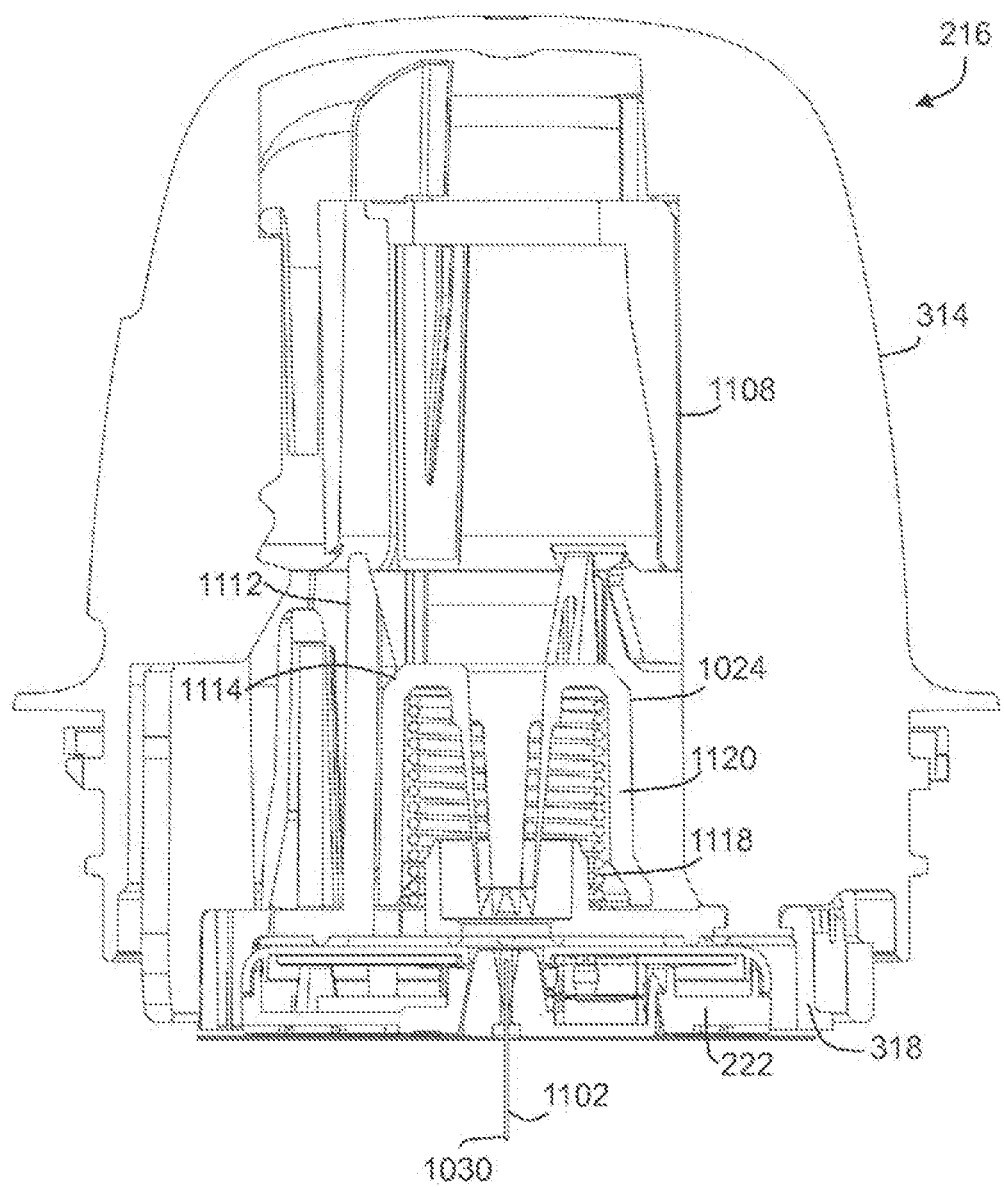
Figure 11D:
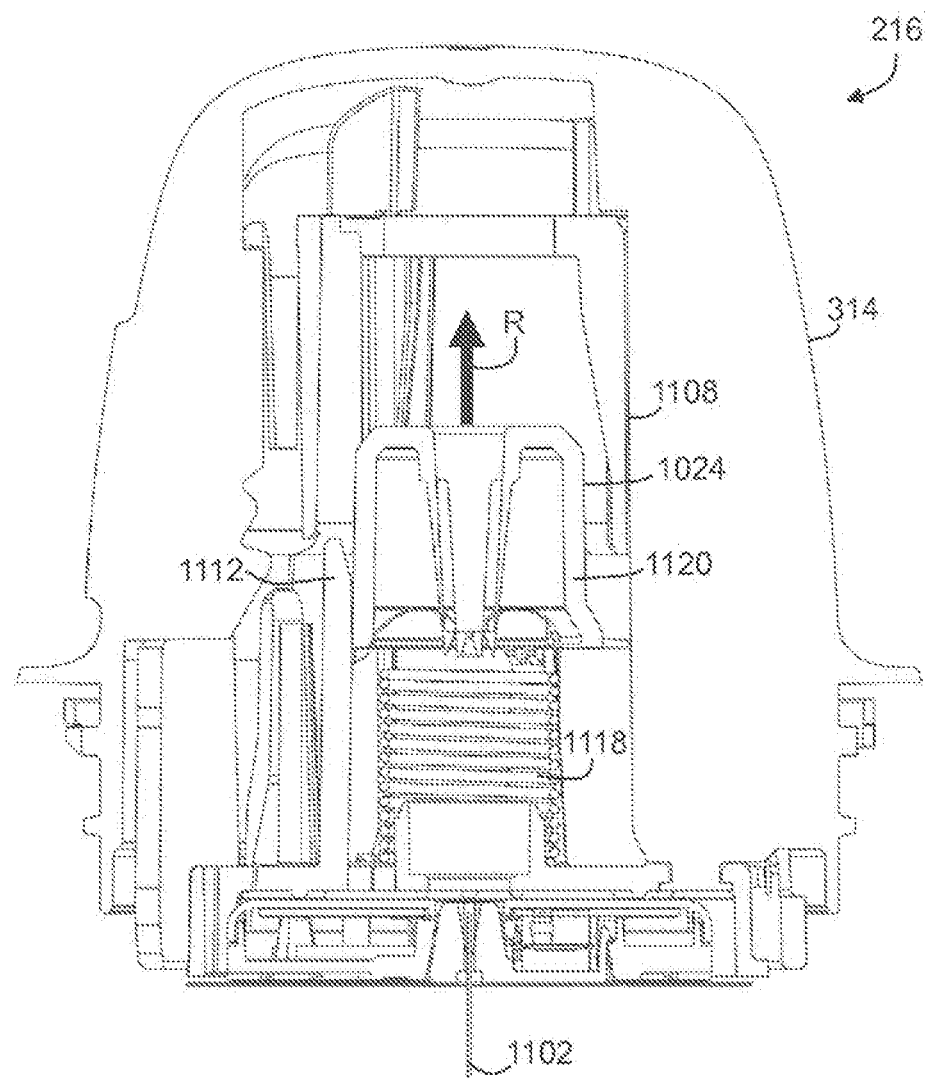

In FIG. 11C, sensor 1102 and sharp 1030 have reached full insertion depth. In so doing, the carrier arms 1112 clear the upper guide section 1108 inner diameter. Then, the compressed force of the coil return spring 1118 drives angled stop surfaces 1114 radially outward, releasing force to drive the sharp carrier 1120 of the sharp retraction assembly 1024 to pull the (slotted or otherwise configured) sharp 1030 out of the user and off of the sensor 1102 as indicated by the arrow R in FIG. 11D.

Figure 11E:
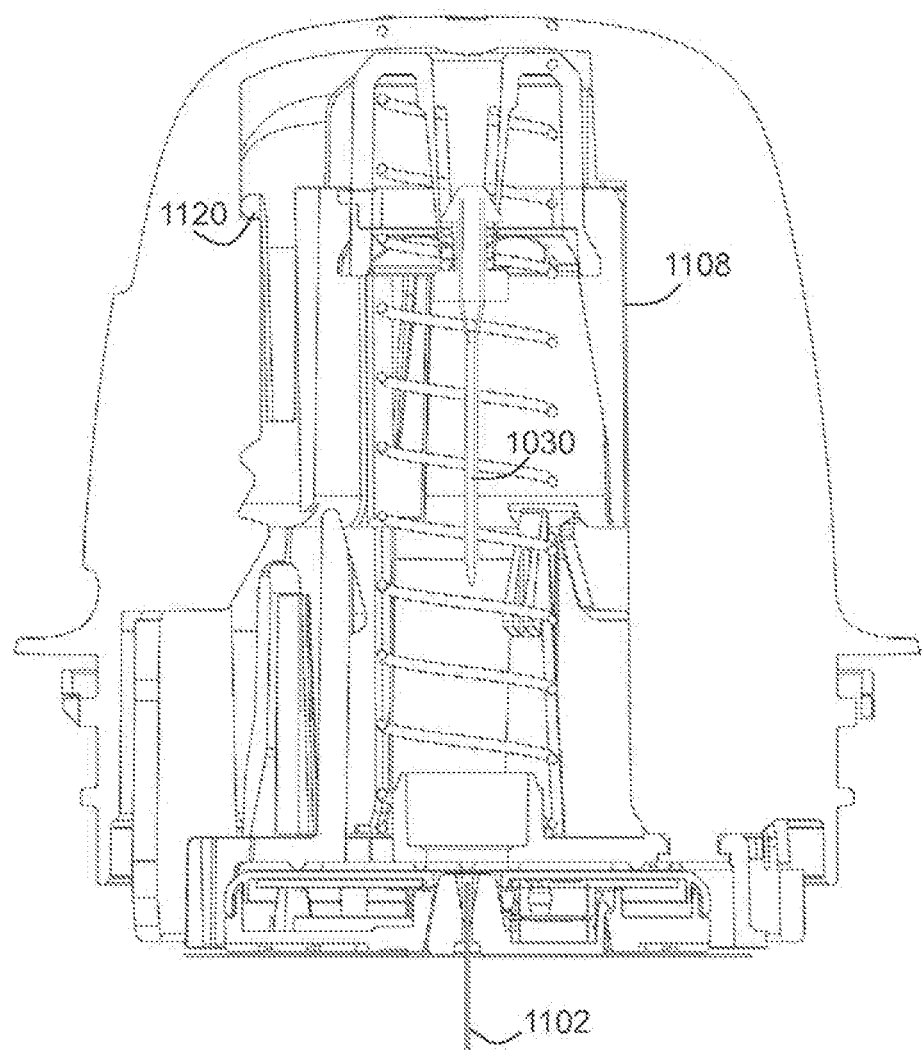
Figure 11F:
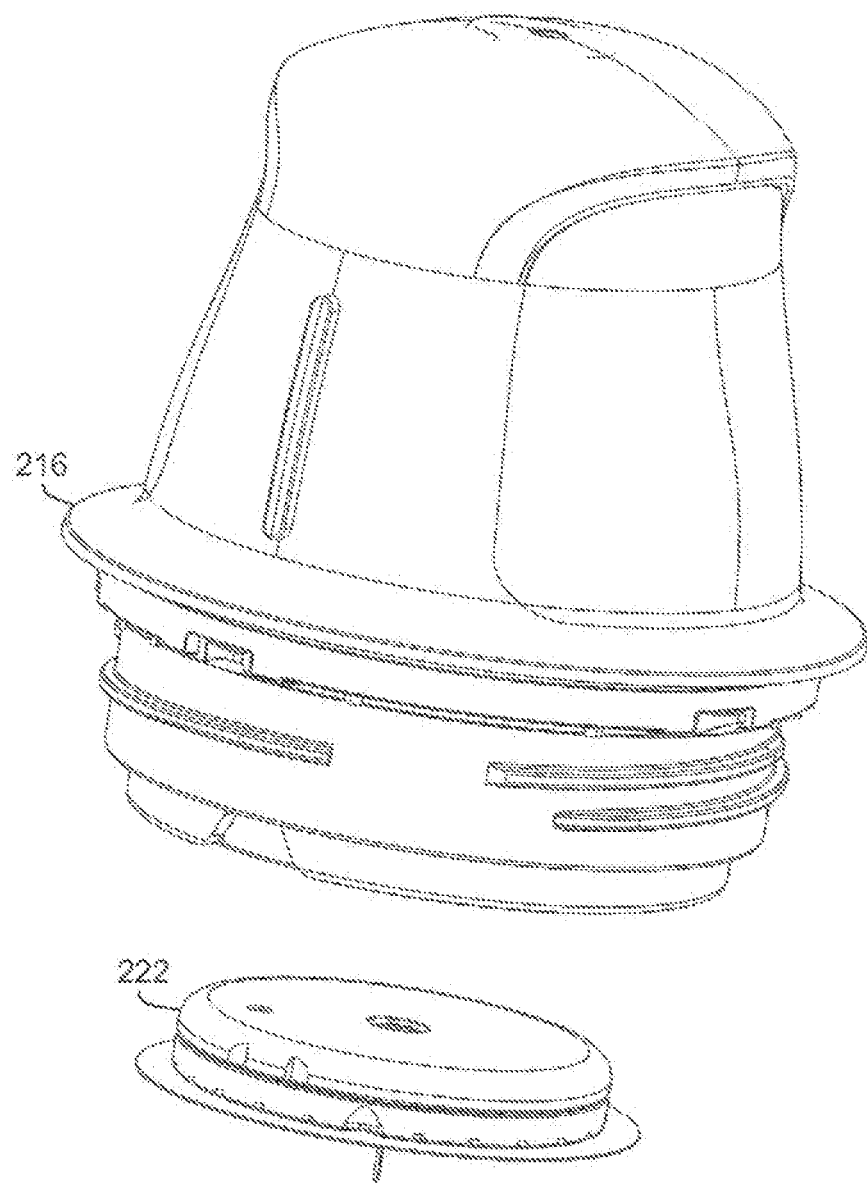

With the sharp 1030 fully retracted as shown in FIG. 11E, the upper guide section 1108 of the sleeve 318 is set with a final locking feature 1120. As shown in FIG. 11F, the spent applicator assembly 216 is removed from the insertion site, leaving behind the on-body device 222, and with the sharp 1030 secured safely inside the applicator assembly 216. The spent applicator assembly 216 is now ready for disposal.

Operation of the applicator 216 when applying the on-body device 222 is designed to provide the user with a sensation that both the insertion and retraction of the sharp 1030 is performed automatically by the internal mechanisms of the applicator 216. In other words, the present invention avoids the user experiencing the sensation that he is manually driving the sharp 1030 into his skin. Thus, once the user applies sufficient force to overcome the resistance from the detent features of the applicator 216, the resulting actions of the applicator 216 are perceived to be an automated response to the applicator being "triggered." The user does not perceive that he is supplying additional force to drive the sharp 1030 to pierce his skin despite that all the driving force is provided by the user and no additional biasing/driving means are used to insert the sharp 1030. As detailed above in FIG. 11C, the retraction of the sharp 1030 is automated by the coil return spring 1118 of the applicator 216.

As for further details of the operation, alternative embodiments may be appreciated in view of related approaches discussed below, others in review of the incorporated subject matter and still more appreciated by those with skill in the art based upon further review of the figures which depict actual hardware produced according to various aspects of the subject disclosure.

Figure 12A:
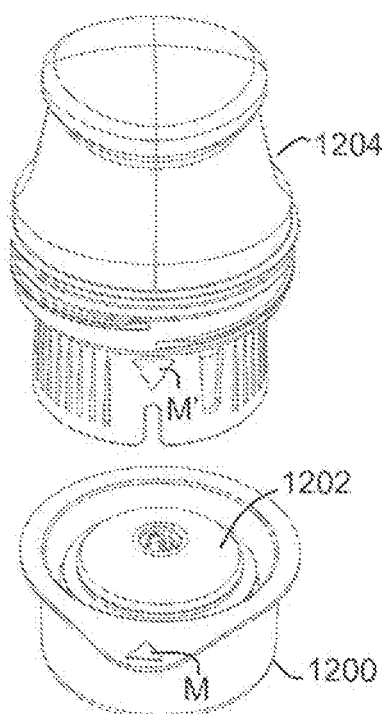
FIGS. 12A-12D are perspectives illustrating another applicator/container set approach in which the container holds the electronics assembly.
Figure 12B:
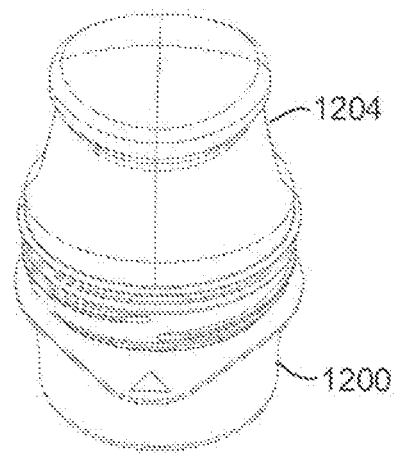
Figure 12C:
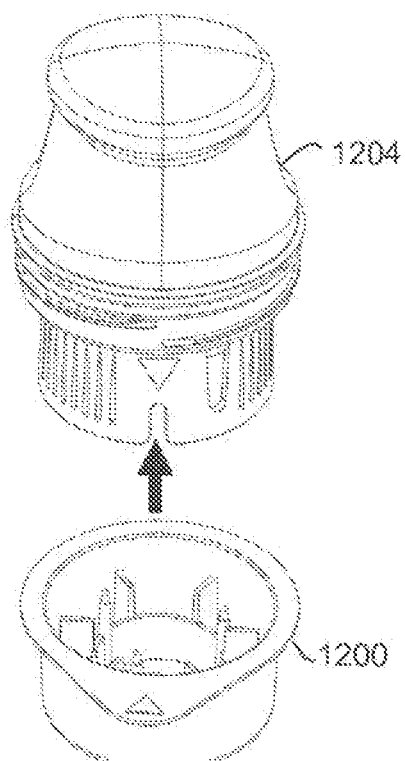
Figure 12D:
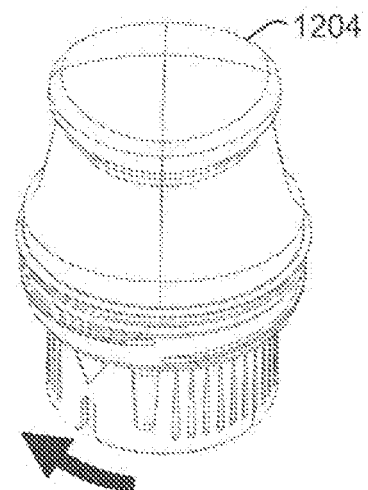

Turning to FIGS. 12A to 12D an alternative applicator/container set approach is now described. As shown in FIG. 12A, the container 1200 holds the electronics assembly 1202. This is in contrast to the above embodiments wherein the relationship between the sensor assembly and the electronics assembly was reversed. Upon aligning markers M and M', the applicator 1204 is inserted in the container 1200. In FIG. 12B, the units are merged. In FIG. 12C, the parts are separated. Finally, in FIG. 12D the applicator 1204 is unlocked (e.g., in some embodiments by twisting the sleeve 1206 within the applicator 1204, in some embodiments by the act of loading the electronics assembly 1202 into the applicator 1204, or in some embodiment by the act of removing a locking strip from the sleeve 1206) and ready for use with the assembled on-body device (not visible) including the sensor assembly loaded therein. These various alternative embodiments are illustrated in FIG. 13A to 15F.

FIGS. 13A to 13C variously illustrate use of the applicator 1204 of FIGS. 12A to 12D in connection with a locking-sleeve feature 1206. FIG. 13A shows the sleeve 1206 locked as indicated by the closed window 1208. After twisting the sleeve 1206 relative to the rest of the applicator 1204 to unlock the sleeve 1206, a visual indication (e.g., open window 1208') is seen when the applicator 1204 is ready for use as presented in FIG. 13B. Upon use, as shown in FIG. 13C, the unit is compressed with the sleeve 1206 collapsed into the applicator 1204.

Figure 14A:
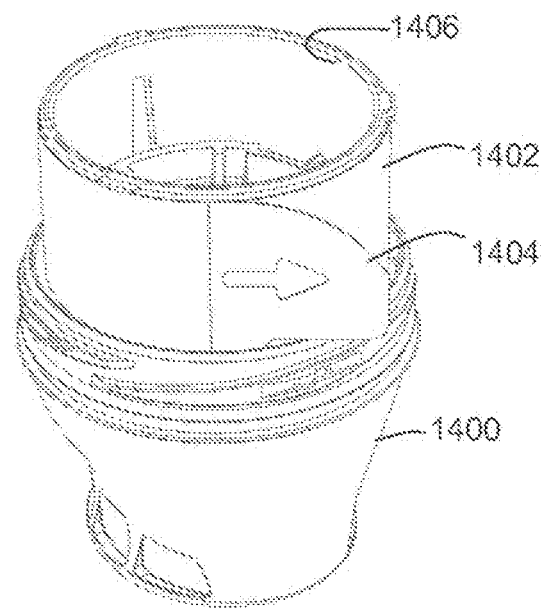
FIGS. 14A and 14B illustrate an applicator with a removable locking strip.
Figure 14B:
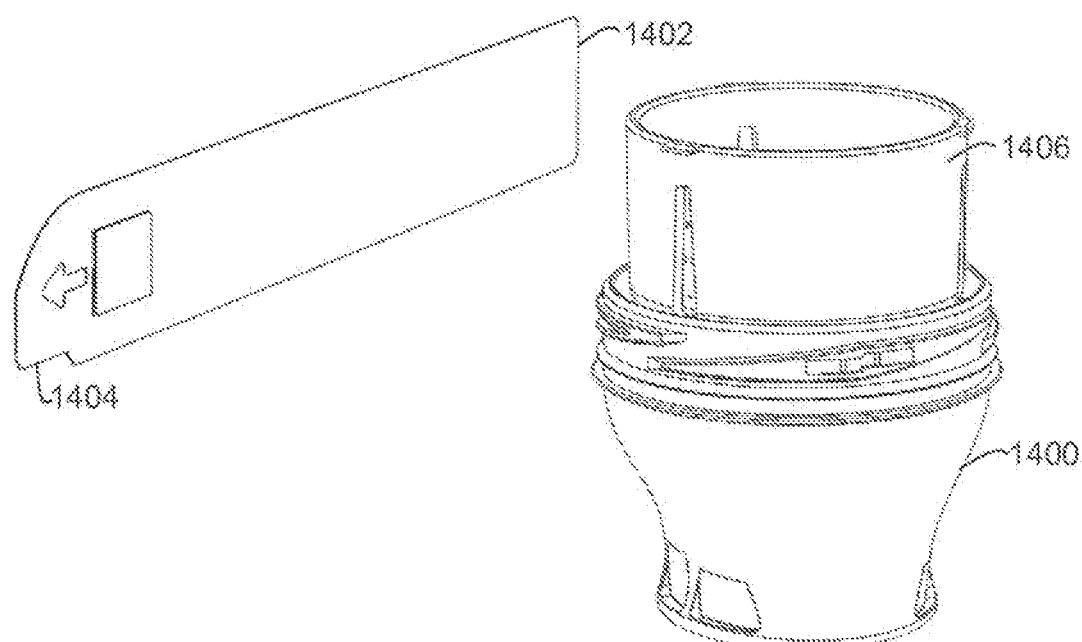

FIGS. 14A and 14B illustrate an alternative applicator 1400 embodiment with a removable locking strip 1402. With the locking strip 1402 in place around the sleeve 1406, the sleeve 1406 cannot be pushed into the applicator 1400. The strip 1402 includes a pull-tab 1404 and adhesive or other fastening member to keep it in place until removed and the applicator 1400 is ready for use.

Figure 15A:
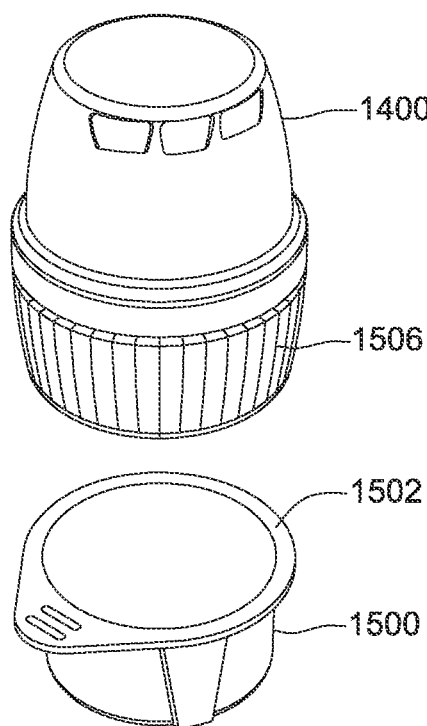
FIGS. 15A-15F variously illustrate use of the applicator in FIGS. 14A and 14B.
Figure 15B:
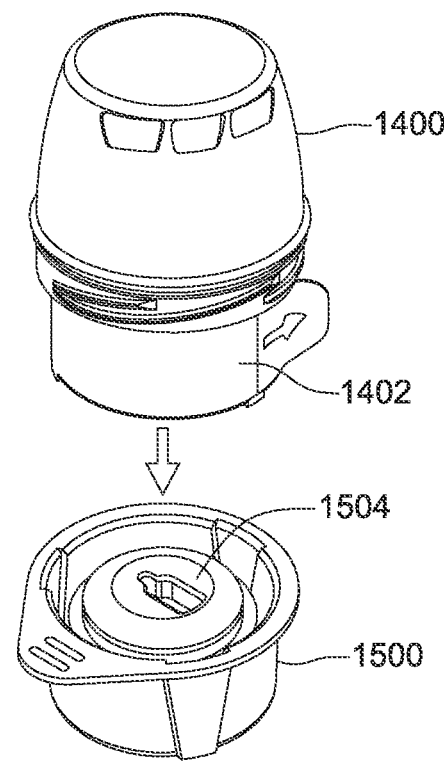
Figure 15C:
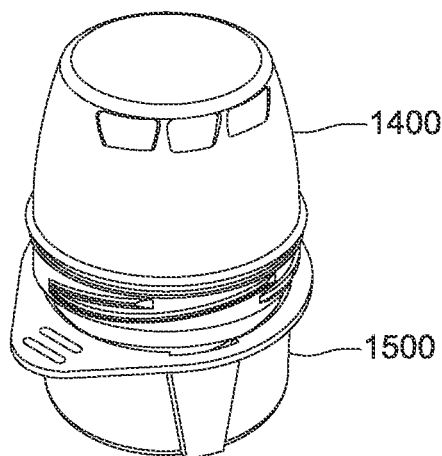
Figure 15D:
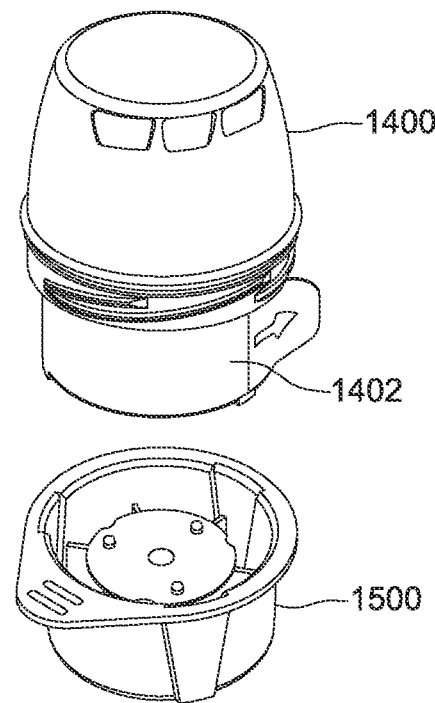
Figure 15E:
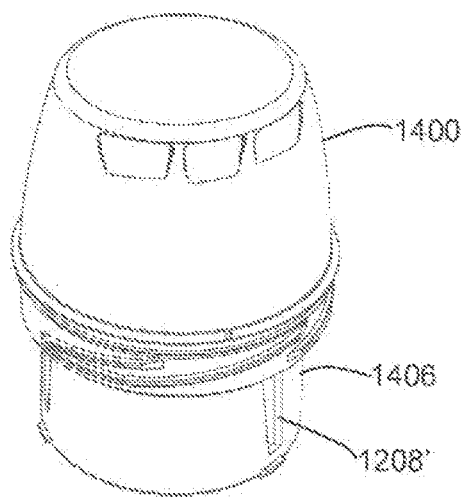
Figure 15F:
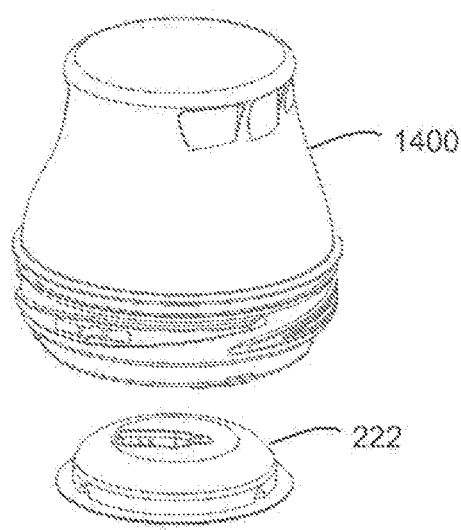

FIGS. 15A to 15F illustrate preparation of the applicator 1400 of FIGS. 14A and 14B for use with a container 1500. Once the cover 1502 has been removed from the container 1500 and the cap 1506 removed from the applicator 1400, the applicator 1400 is inserted into container 1500 to load the electronics assembly 1504 into the applicator 1400 and mate the sensor assembly (not shown) with the electronics assembly 1504 as shown in FIGS. 15B and 15C. Once loaded, the applicator 1400 is removed from the container 1500 as shown in FIG. 15D. FIG. 15E shows the applicator 1400 loaded with the assembled on-body device 222 and ready for sensor/sharp insertion. The locking strip 1402 is removed from the sleeve 1406 and the open ready indicator 1208' signals that the applicator 1400 is ready to be used. FIG. 15F illustrates the system after such action has been taken in transferring the on-body device 222 from the applicator 1400 onto the skin of a user.

Figure 16A:
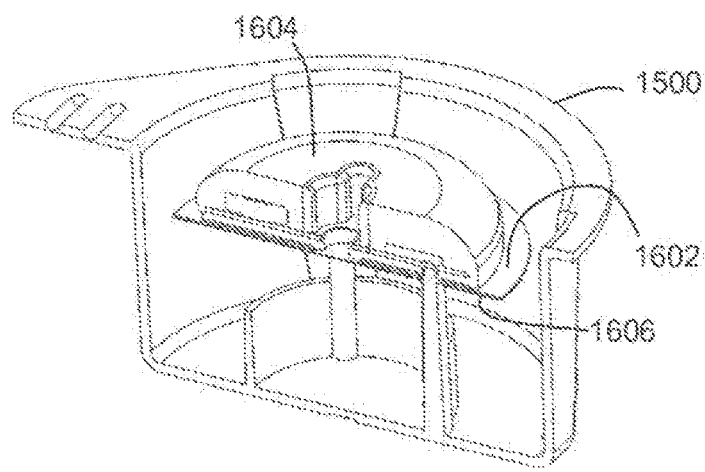
FIGS. 16A and 16B are sectional and detail to views, respectively, of features of the container in FIGS. 15A-15D.
Figure 16B:
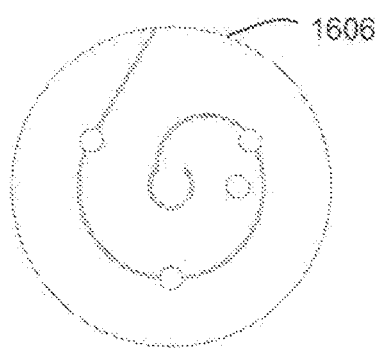
Figure 17A:
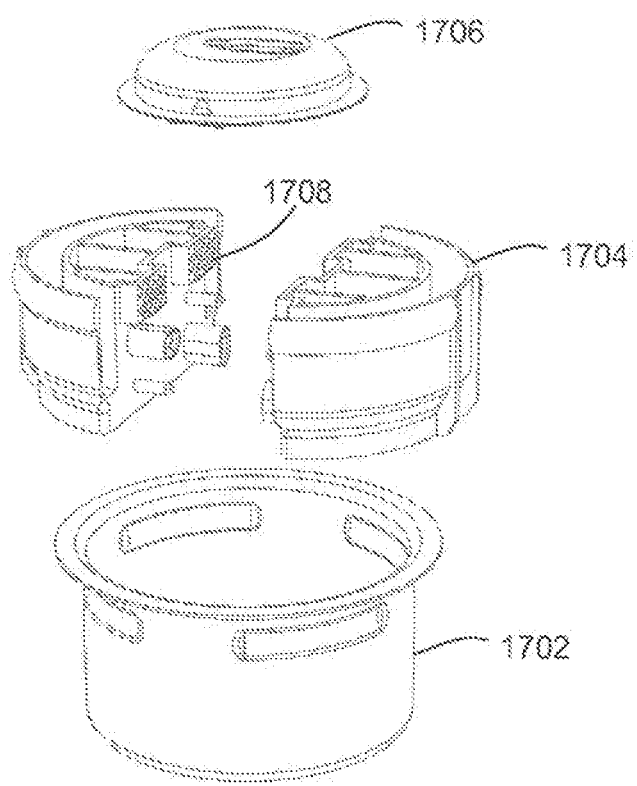
FIGS. 17A and 17B are perspective assembly views illustrating alternative container configurations to that illustrated in FIGS. 16A and 16B.
Figure 17B:
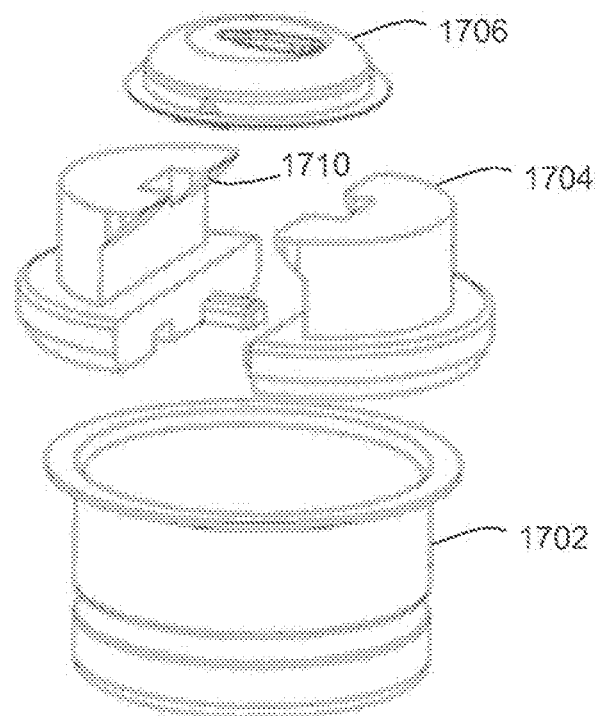

FIGS. 16A and 16B are sectional and detail views, respectively, of features of the container 1500 in FIGS. 15A-15F. Specifically, the on-body device 1604 is shown in the container 1500 with an adhesive patch 1602 and its backing 1606. The backing 1606 is spiral-cut and attached to a boss so that when the on-body device 1604 is transferred from the container 1500, the peel-away backing 1606 is left behind. In this fashion, the adhesive patch 1602 remains covered by the backing 1606 so it does not inadvertently adhere to the container 1500.

As an alternative to the spiral peel-around backing approach of FIGS. 16A and 16B, FIGS. 17A and 17B are perspective assembly views illustrating alternative container 1702 configurations for capturing separate peel-off "butterfly" wings or bilateral liner panels from the adhesive-backed patch of the on-body device 1706. In each case, a two-part base 1704 is provided for gripping the peel-away backing liner pieces. Naturally, the base 1704 is adapted to fit in the container casing. In some embodiments, the container 1702 can be configured differently. In the version depicted in FIG. 17A, traction/tread 1708 is provided to assist with grip of the backing. In the version depicted in FIG. 17B, ramps 1710 are provided to assist in removing the backing. In another version, the base can be a one-piece molding incorporating a living hinge in a "clamshell" arrangement. The backing liner piece(s) may be captured along a center line or at an offset location. However configured, the base 1704 may snap into place with complementary band and rib interface features associated with each of the base 1704 and container 1702, snaps, or other features. As with other assemblies described herein, these features may alternatively be press fit, ultrasonically welded or otherwise secured in place.

Figure 18:
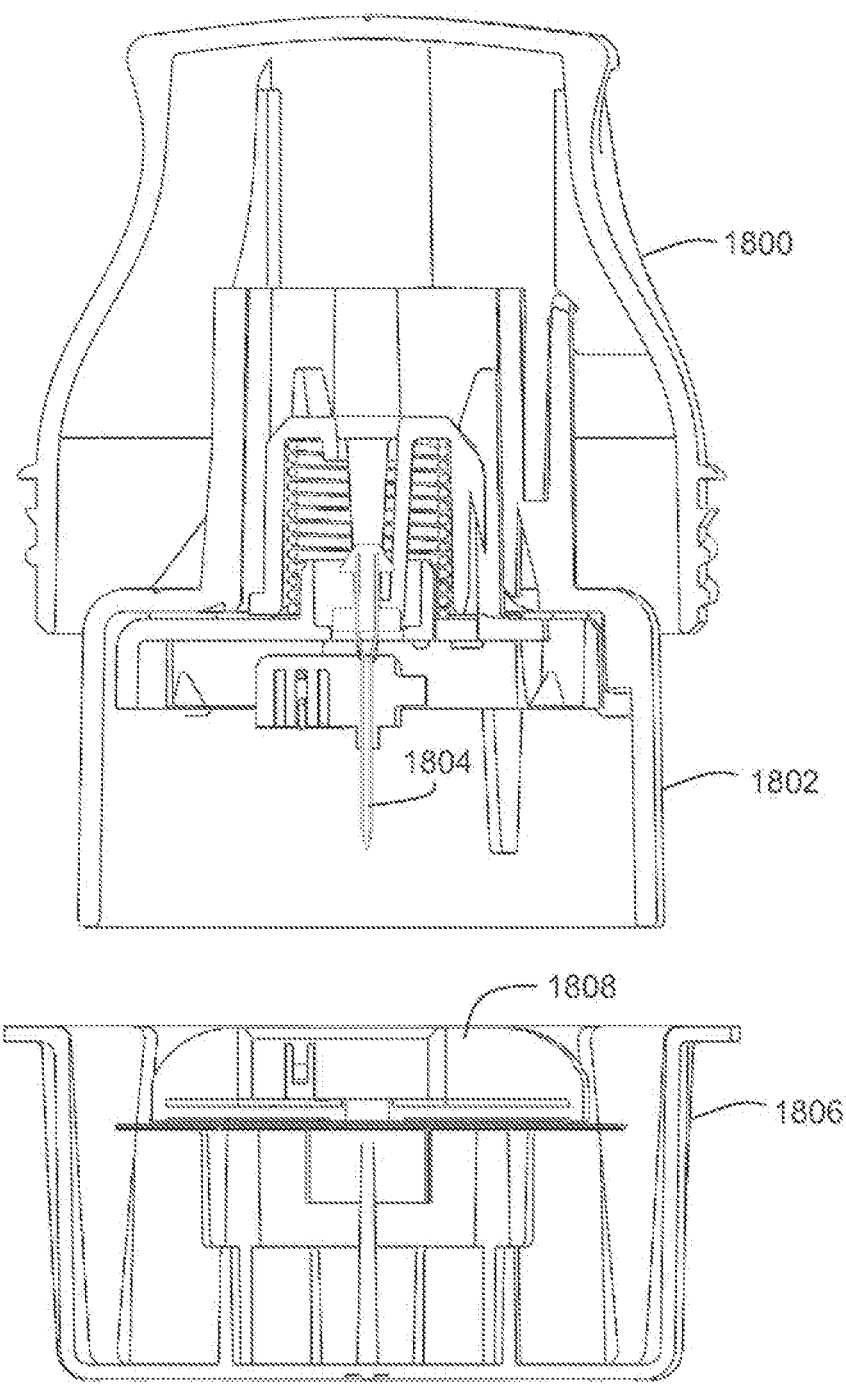
FIG. 18 is a side-section view illustrating the features of the applicator and container sets variously shown in FIGS. 15A-15F.

FIG. 18 is a cross-sectional view illustrating features of the applicator and container sets shown in FIGS. 15A-15F. The embodiment shown in FIG. 18 includes several of the features described in connection with the alternative loading approach above. However, it is simplified in approach. Most notably, the container 1806 includes no active/mobile components. Once the applicator 1800 is pressed down into the container 1806, the on-body device 1808 is assembled (e.g., the sensor assembly is mated with the electronics assembly), released from the container 1806 (e.g., using releasable latches), and held by the applicator 1800 (e.g., using latching arms). This embodiment offers an advantage of not having to expose the adhesive of the on-body device 1808 as in other embodiments. Furthermore, the position of the on-body device 1808 provides a stable surface for the sensor assembly insertion. Other embodiments where the applicator is pre-loaded with the on-body device do provide the advantage of not having to perform the above-described hand-off. Also, the use or inclusion of a protector for the sharp is avoided.

Figure 19A:
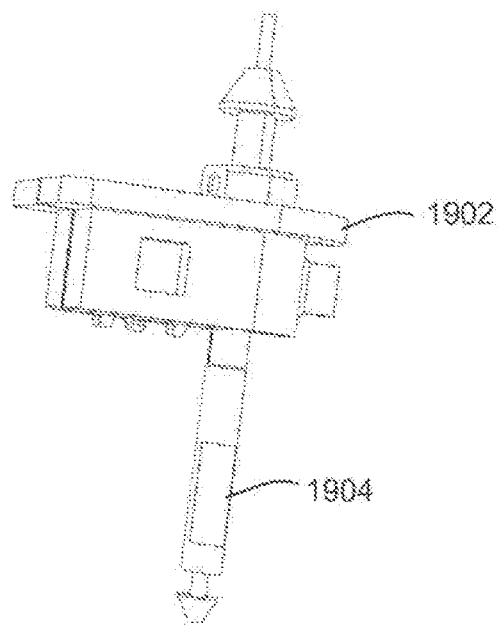
FIGS. 19A and 19B are perspective views of a sensor assembly incorporated in the system shown in FIG. 18.
Figure 19B:
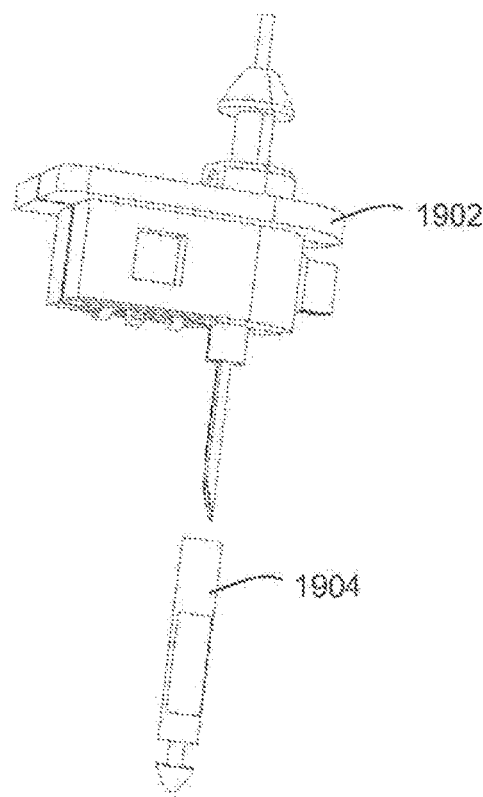

FIGS. 19A and 19B show a sensor assembly 1902 in association with a needle guard 1904. In use, a distal interface feature (e.g., a barb) of the needle guard 1904 is captured by a complimentary split ring or other feature in the container during the assembly of the on-body device. Then, when the applicator is separated from the container, the needle guard 1904 is retained in the container and the sharp is unsheathed. In some embodiments, the needle guard 1904 may be made from polypropylene with a thermoplastic elastomer (TPE) insert to releasably secure the sharp. Other materials may be selected.

Other materials may be selected for construction of other elements of the present invention. For example, the applicator housing may be made of polycarbonate or any other practicable material. The guide sleeve, container, etc. may be constructed from acetyl (for reason of lubricity of sliding parts). Any number of the parts may be injected molded, thermoformed or otherwise produced.

Figure 20A:
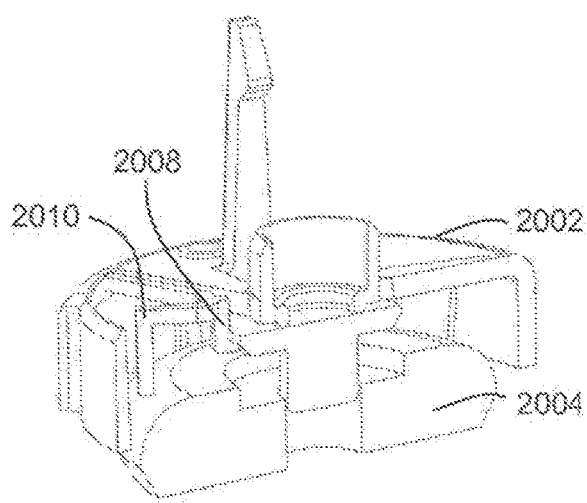
FIGS. 20A and 20B are perspective views of the operation of a sensor assembly retention unit incorporated in the system shown in FIG. 18.
Figure 20B:
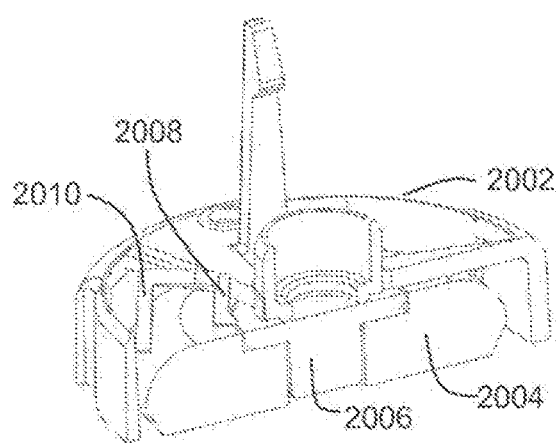

Regarding the sensor assembly hand-off to the electronics assembly, FIGS. 20A and 20B illustrate a manner of holding a sensor assembly boss 2006 to the element 2002 that will pick up the electronics assembly 2004 to form the on-body device. Spring armatures 2008 clip to a lip of the sensor assembly 2006 and hold the sensor assembly 2006 within the applicator during shipping and handling. When the applicator and the container are brought together, lever arms 2010 contact the on-body device 2004, causing the associated spring armatures (or "spring arms") to twist and rotate the connection away from the lip of the sensor assembly, thereby releasing the sensor assembly. A chamfer on the sensor assembly boss can help ensure alignment and proper actuation of the one or more (e.g., three) torqueing spring armatures 2008.

Figure 21A:
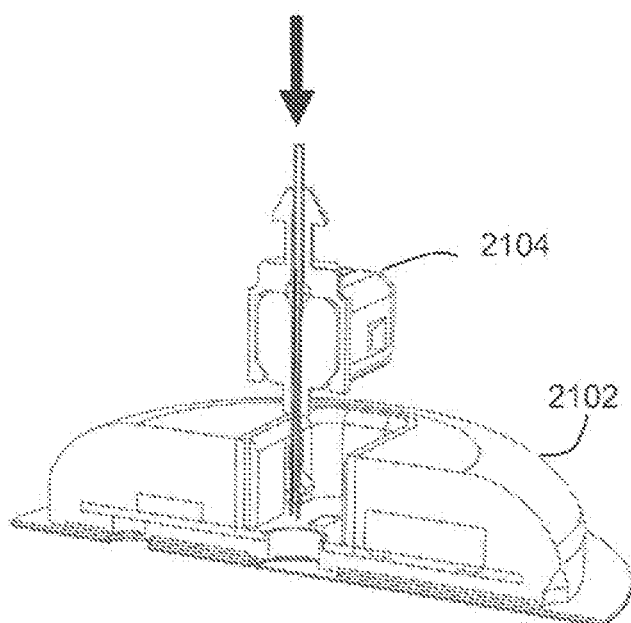
FIGS. 21A-21C are perspective section views illustrating sensor assembly receipt by the sensor mount and sharp withdrawal from the assembled complex.
Figure 21B:
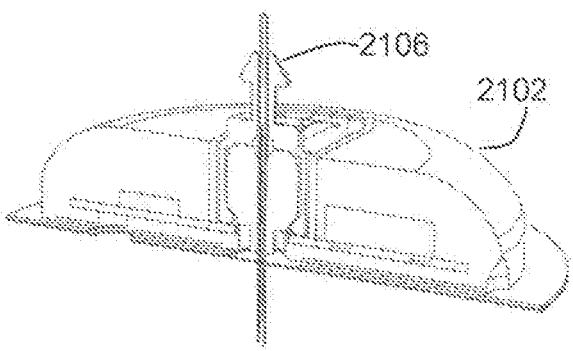
Figure 21C:
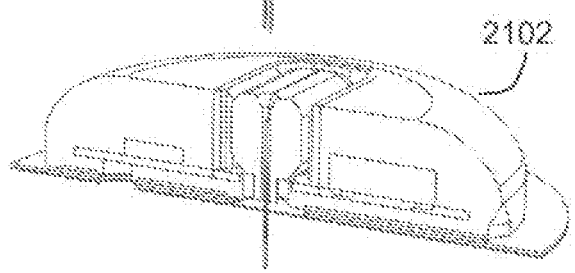

FIGS. 21A-21C illustrate an alternative hand-off approach. In this embodiment, a sensor assembly gripper 2106, with a light snap fit, grabs and orients the sensor assembly 2104 for connection to the electronics assembly 2102. After the sensor assembly 2104 is firmly snapped into the electronics assembly 2102, the sensor assembly gripper 2106 is retracted with an amount of force that overcomes its grip. Such an approach offers simplicity by reducing the number of parts required (given that the snap features may be incorporated in the sharp hub/boss).

Electrical Connections Details

The selection of various hardware options from the above alternative embodiments will depend, at least in part, on the sensor assembly configuration. Sensor assembly configuration, in turn, depends on the mechanism selected for establishing electrical contact between the sensor assembly and the electronics assembly, as well as the method used to seal the contacts. A number of advantageous alternative embodiments are illustrated in FIGS. 22 through 48.

Figure 22:
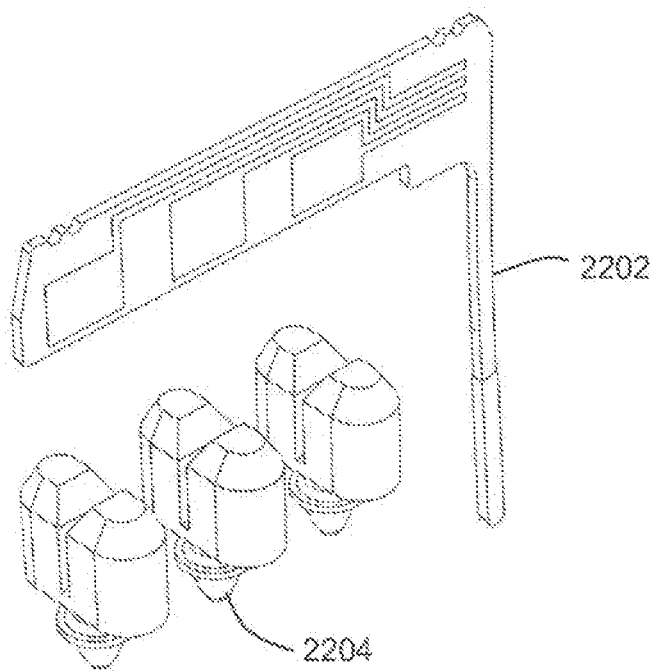
FIG. 22 is a perspective assembly view of advantageous sensor and sensor connector elements.
Figure 23A:
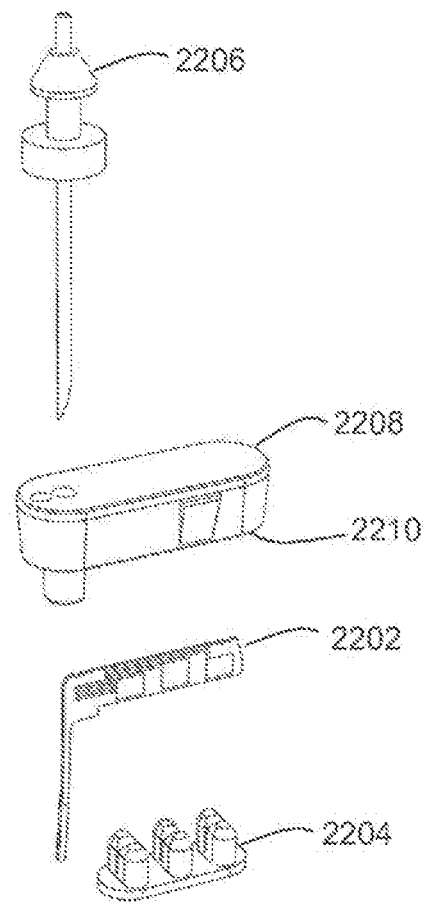
FIGS. 23A and 23B are perspective assembly and final-assembly views, respectively of the sensor components in FIG. 22.
Figure 23B:
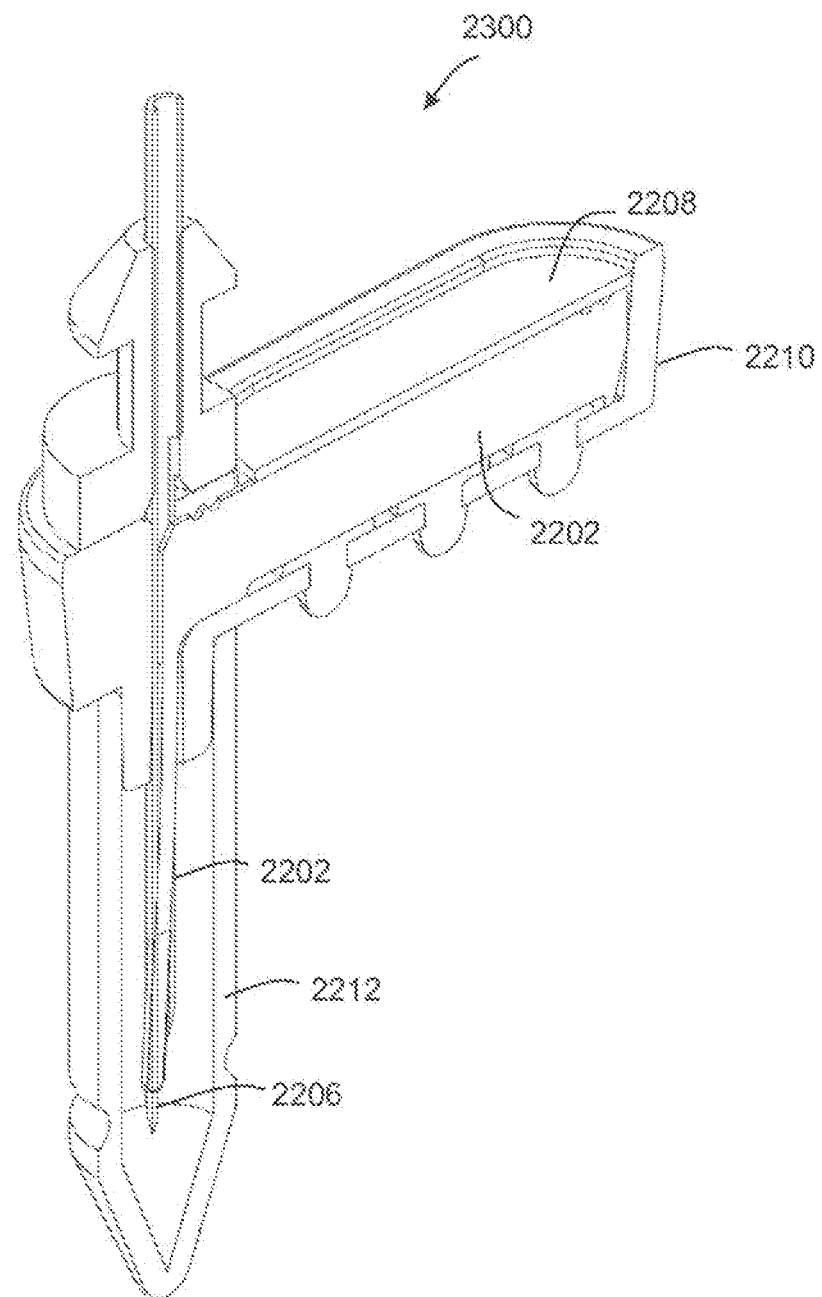

A first example is presented in FIG. 22. Here a sensor 2202 is provided with an elongate "tail" section. The distal portion of the tail is to be inserted through the skin surface guided by a sharp. The proximal portion of the sensor 2202 includes a "flag" type connector region. Three carbon-doped (for conductivity) silicone electrical connectors 2204 are provided to interface with the electrical contacts of the sensor 2202. A split "V" portion of each connector 2204 receives the electrical contacts of the sensor 2202. A flexible nubbin on the opposite side of each connector 2204 is provided for electrical contact with the circuit board incorporated in the electronics assembly. When inserted in a housing 2210, the sensor 2202 and the connector 2204 are advantageously sealed, encased or potted with an adhesive. Epoxy, a UV cure or another type of dielectric (non-conductive) compound may be used. Generally, the compound selected is of such viscosity that it is able to flow around features and fully seal the sensor 2202 within its housing 2210 to avoid leakage. Such an approach avoids contamination and/or current leakage due to fluid intrusion. FIGS. 23A and 23B are perspective assembly and final-assembly cross-sectional views, respectively of the sensor components of FIG. 22. The tail of the sensor 2202 is supported within the sharp 2206 and the sharp 2206 extends through the connector housing 2210. The electrical contacts of the sensor 2202 are seated in the connector 2204 and the assembly is sealed within the housing 2210 including the housing top 2208.

Figure 24A:
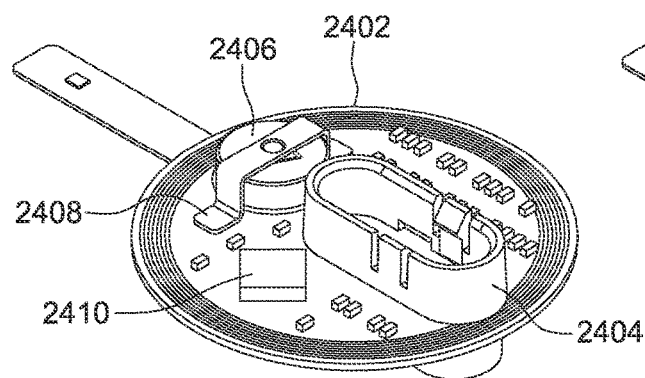
FIGS. 24A and 24B are top and bottom perspective views, respectively of circuit board components to be used with the assembly shown in FIGS. 23A and 23B.
Figure 24B:
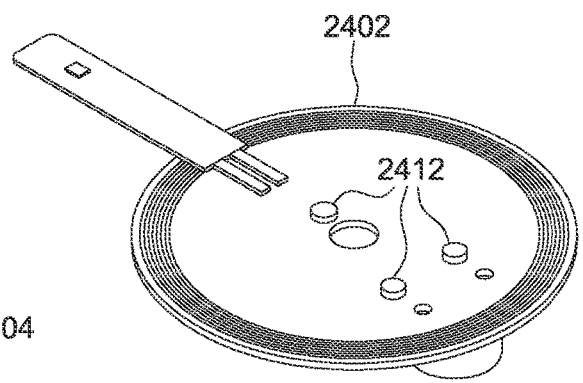

FIGS. 24A and 24B are top and bottom perspective views, respectively of circuit board components to be used with the sensor assembly 2300 of FIGS. 23A and 23B. In each, a custom printed circuit board (PCB) 2402 is shown. The PCB 2402 includes a battery 2406 with mount 2408, an application specific integrated circuit (ASIC) 2410, or other appropriate processing unit, and various other circuitry, including a thermocouple. On its face, the PCB 2402 includes a housing 2404 with snap features for receiving the sensor assembly 2300 of FIGS. 23A and 23B. On the reverse side of the PCB 2402, heat stakes 2412 show the mode of attaching the housing 2404.

Figure 25A:
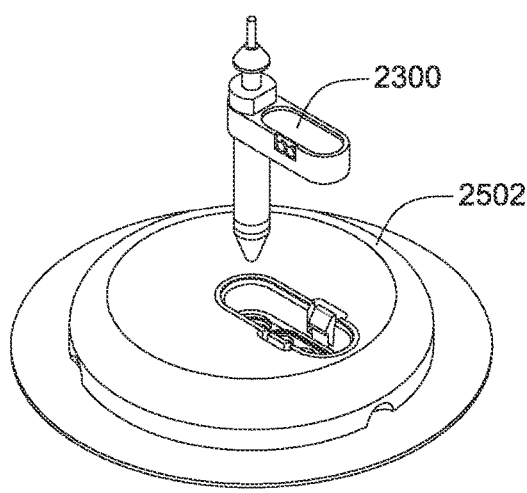
FIGS. 25A and 25B are perspective views illustrating assembly of the subject components in stages.
Figure 25B:
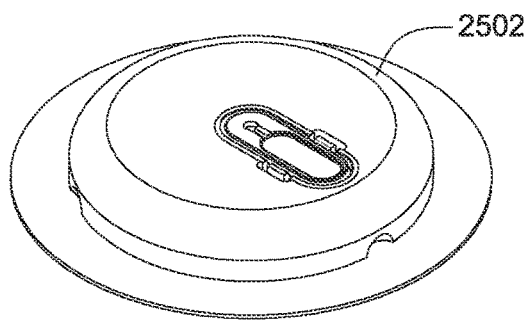
Figure 26:
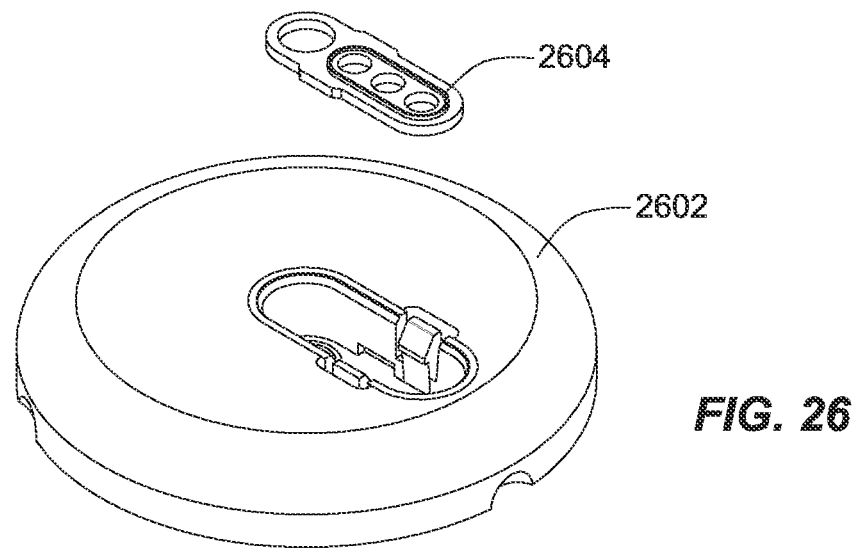
FIG. 26 is an assembly view of the on-body/sensor mount unit in FIGS. 25A and 25B illustrating an advantageous seal element.
Figure 27A:
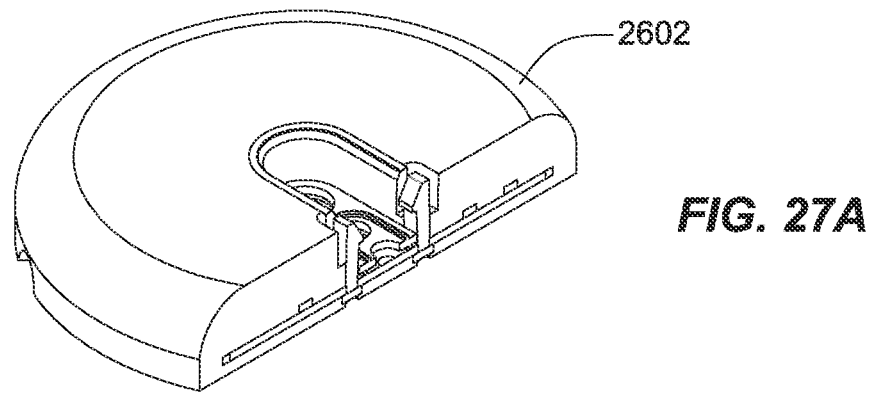
FIGS. 27A and 27B are section views further illustrating the seal element and its relation to the mount in FIG. 26.
Figure 27B:
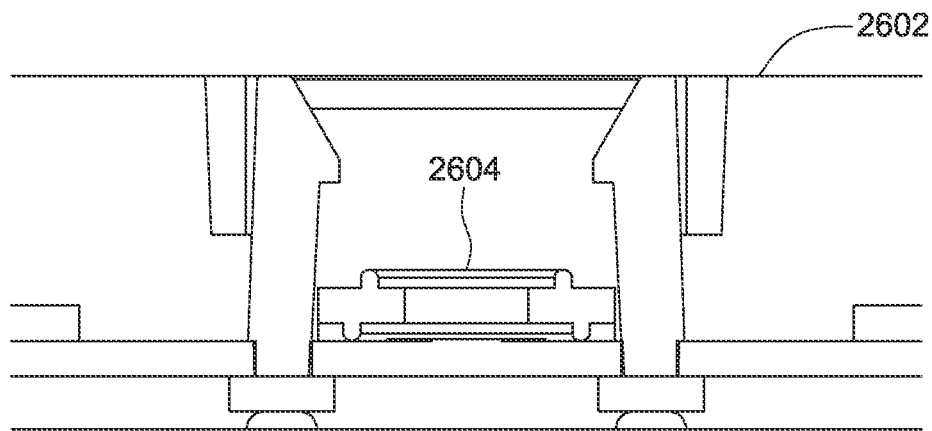
Figure 29A:
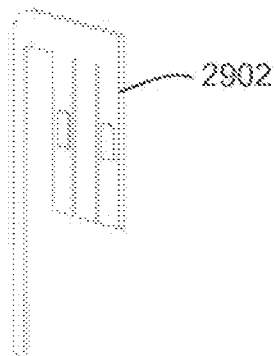
FIGS. 29A-D are perspective views of another advantageous sensor and sensor connector arrangement.
Figure 29B:
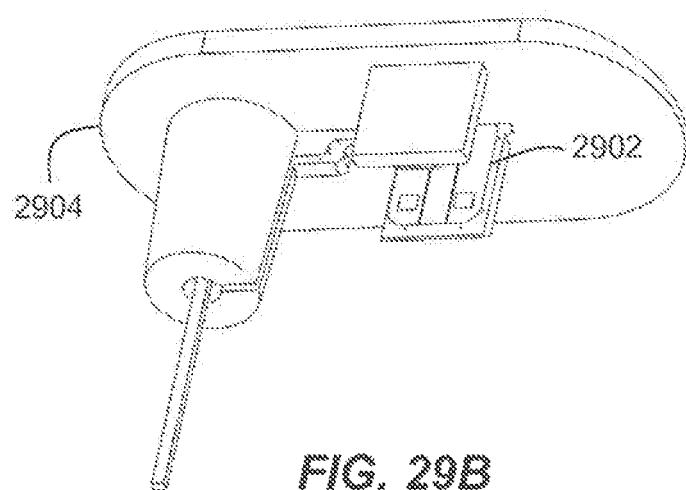
Figure 29C:
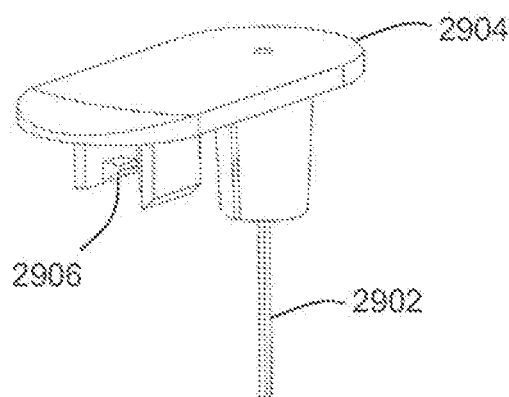
Figure 29D:
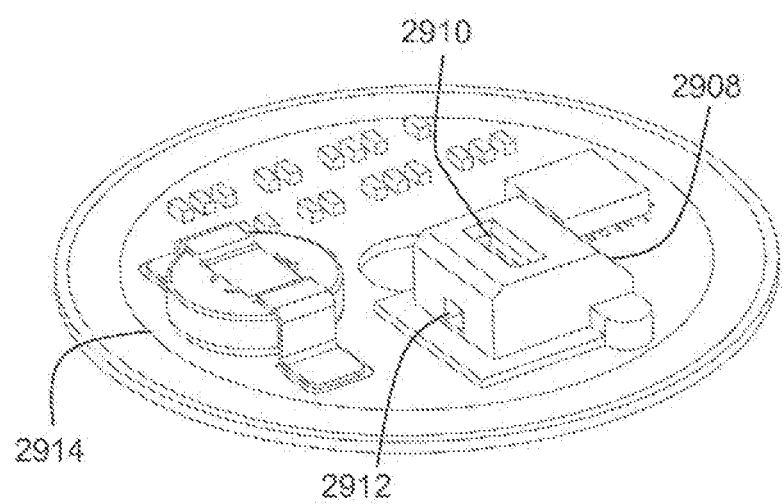

Turning to FIGS. 25A and 25B, in some embodiments, the on-body device 2502 is formed by over molding with a polymer "macromelt" (e.g., a thermoplastic hot-melt based on polyamide) or other compound and then affixing an adhesive patch with a releasable liner thereto. A completed on-body device 2502 is provided once fitted with a complimentary sensor assembly 2300, as illustrated in FIGS. 25A and 25B. Internal to such assembly, it may be desirable to include a seal or gasket 2604 as shown in assembly view FIG. 26. As shown in cross section, in FIG. 27A, and magnified in FIG. 27B, the gasket 2604 advantageously includes discrete ring/rim elements to compress and ensure sealing in critical areas, including around each circuit connection/nubbin.

FIGS. 28A-28F illustrate another advantageous sensor 2802 and sensor mount or connector 2804 arrangement. This embodiment resembles the previous approach, but is configured with a bend and a curve imparted to the sensor connection "flag." This permits package and sealing within in a roughly triangular envelope to shorten the length of the connector. Doing so results in a generally more compact sensor assembly body and the ability to downsize all associated components. Yet, it does not significantly complicate manufacture. FIG. 28A depicts the sensor 2802 before it is shaped to fit within the connector 2804. FIG. 28B depicts the bent and curved sensor connection "flag." FIG. 28C depicts the relative orientation of the sensor 2802 as it is inserted into the connector 2804. FIG. 28D depicts a wedge 2806 that is press-fit into the connector 2804 to retain the sensor 2802 and press the connector's electrical contacts against the electrical contacts of the sensor 2802. FIG. 28E depicts the relative orientation of the sharp 2808 as it is inserted into the connector 2804 and FIG. 28F depicts the completed sensor assembly including potting 2810 (e.g., UV potting) used to seal the electrical contacts.

An alternative embodiment is contemplated in connection with the sensor approach illustrated in FIGS. 29A-29D. Using a sensor 2902 with a vertically disposed "flag" connector portion that is supported by coupling 2904, coupling 2904 is configured to snap into connector block 2908 which is attached to PCB 2914. Connector block 2908 includes a connector socket 2910 to receive the contacts portion of the sensor 2902. Connector block 2908 also includes a coupling feature 2912 to receive snap-fit tab 2906 on the coupling 2904 which retains the sensor 2902 in the connector socket 2910.

Figure 30A:
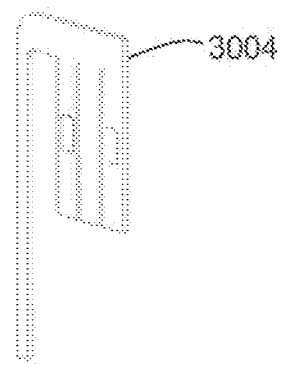
FIGS. 30A-30B are perspective views illustrating yet another advantageous sensor approach with the sensor as originally produced and modified for use, respectively.
Figure 30B:
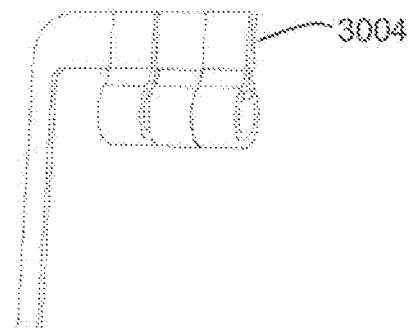
Figure 30C:
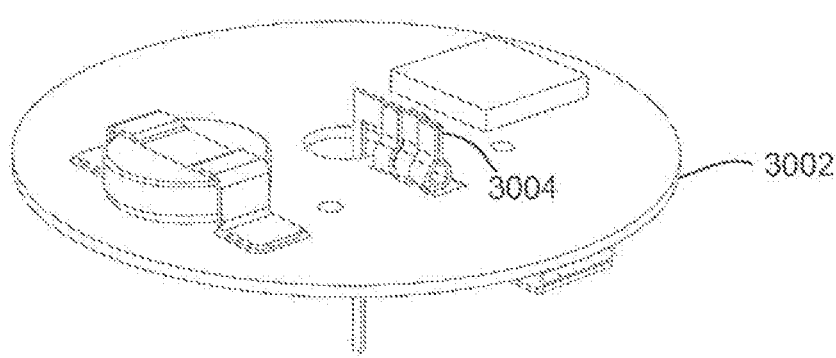
FIG. 30C is a perspective view illustrating the sensor as configured in FIGS. 30A and 30B coupled to a PCB.

Another alternative embodiment is contemplated in connection with the sensor approach illustrated in FIGS. 30A-30C. Here, a design is provided that eliminates a connection element and the need for separate spring contacts (be they metal or elastomeric as above). In addition, the approach offers the advantage of effectively converting a sensor with contacts on two sides into a sensor with contacts on a single side after folding. The sensor 3004 shown in FIG. 30A initially has two electrical contacts facing a first direction on the split contact area and one contact facing in a second, opposite direction (obscured by the view). When folded and optionally clamped, glued or otherwise affixed in the orientation shown in FIG. 30B, all of the electrical contacts lie in a single plane, facing the same direction (e.g., downward in the drawing). Set within a housing (not shown) to restrain and/or seal the sensor 3004, the sensor 3004 is coupled to electrical contacts on the PCB 3002 as shown in FIG. 30C.

Figure 31:
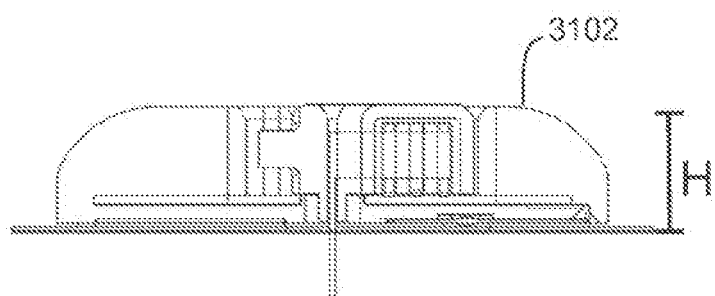
FIG. 31 is a side-section view showing a comparative approach, in a final on-body sensor assembly.

Such an approach in some embodiments includes a thinner (e.g., lower profile) on-body device relative to the on-body device 3102 variation shown in FIG. 31. The reduced thickness dimension is represented by height H. In FIG. 31, a flag type sensor is shown in a housing with separate electrical connectors. The "stack height" in FIG. 31 includes these connectors as well as the housing. The approach shown in FIG. 30 enables eliminating the connector height above the sensor 3004. Thus, elements are eliminated without losing functionality. Moreover, the elimination of parts reduces cost, and impedance (relative at least to the inclusion of elastomeric connectors as shown in FIG. 22, etc.) between the sensor 3004 and the PCB. Another useful aspect is allowing a sensor with contacts on two sides to connect to the PCB without requiring vias or holes in the sensor, thereby helping with sealing considerations and ease of electrical connection.

Figure 32A:
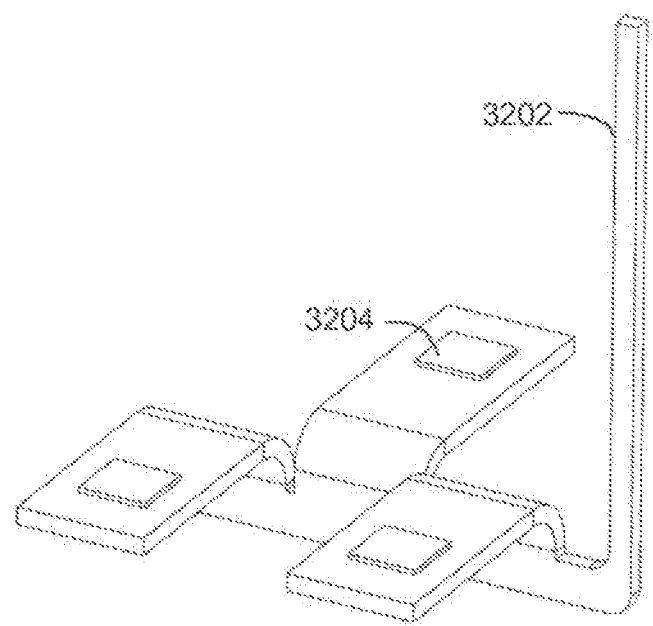
FIGS. 32A and 32B are perspective views of still other advantageous sensor configurations, these figures illustrating split-sensor approaches.
Figure 32B:
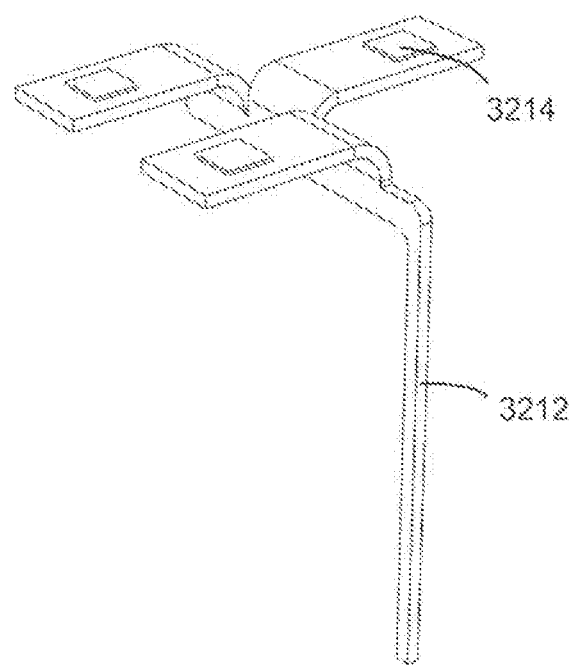

FIGS. 32A and 32B illustrate two additional sensor configurations. In these embodiments, sensors 3202, 3212 with contacts on two sides are split and bent in opposite directions to orient the electrical contacts 3204, 3214 onto a single face or plane. As above, orienting the electrical contacts 3204, 3214 onto a single plane facilitates ease of sealing the electrical connections. Moreover, overall sensor assembly height can be reduced relative to other approaches. Any of conductive adhesives, conductive films and/or mechanical contacts may be used to electrically connect with the sensor contacts so arranged.

Figures 33A, 33B:
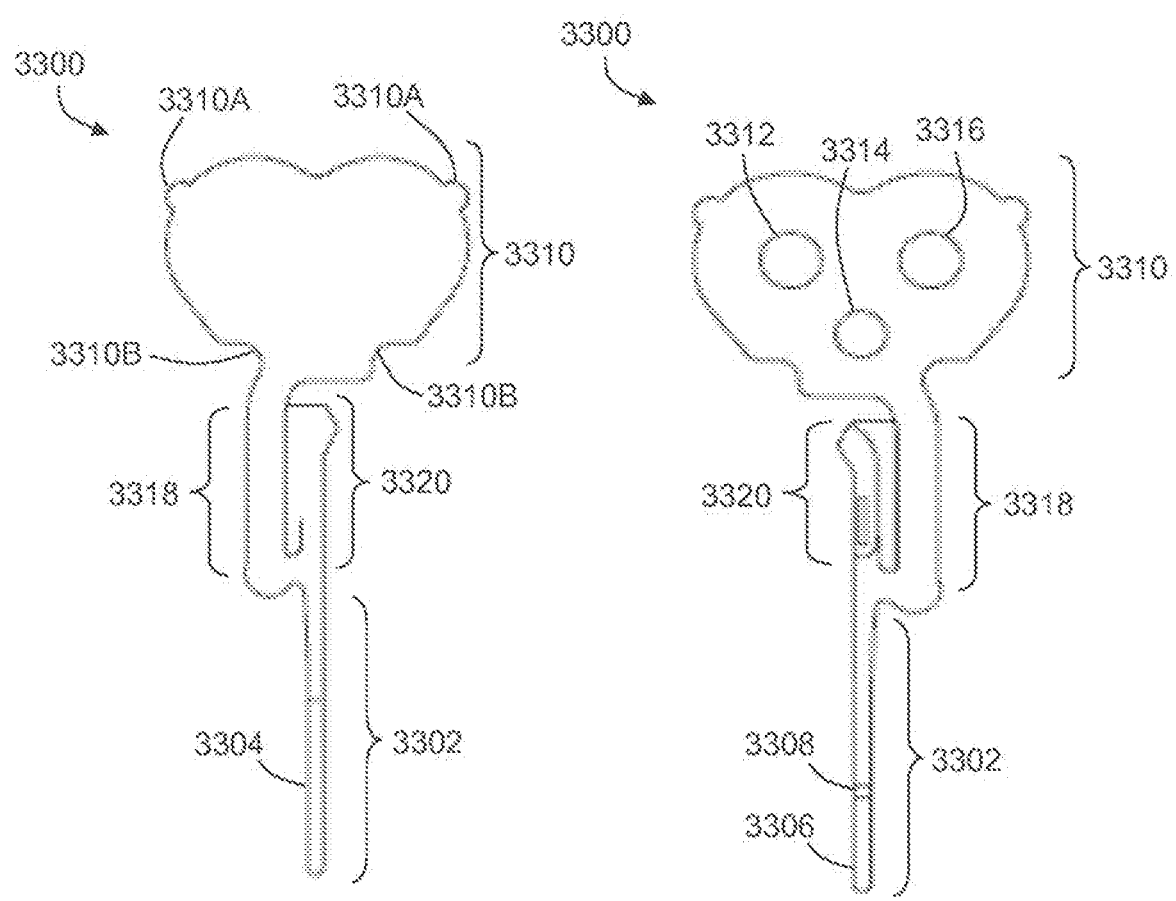

FIGS. 33A-33G depict a low-profile multilayer sensor configuration with the electrical contacts all on one side and some details of its construction. FIGS. 33A and 33B illustrate the two sides of this embodiment of a sensor 3300 and its overall shape. The example sensor 3300 includes a tail portion 3302 that is initially supported by a sharp and then disposed within the user's interstitial fluid or dermal space below the skin upon application of the on-body device. The tail portion 3302 includes electrodes 3304, 3306, 3308 that are used to contact the interstitial fluid and to sense (e.g., transmit and receive) the electrical signals used to measure the analyte concentration within the interstitial fluid. The sensor 3300 also includes an electrical contacts portion 3310 which includes electrical contacts 3312, 3314, 3316 that are disposed all on one side of the sensor 3300 and are in electrical communication with the electrodes 3304, 3306, 3308 via conductive traces (not visible in FIGS. 33A and 33B but see FIG. 33F). Note also that the electrical contacts portion 3310 is shaped to facilitate being securely held and sealed into a connector support that will be described below. For example, the electrical contacts portion 3310 includes securement features that hold the sensor to be secured to the connector support by friction fit, interference fit, etc., herein shown as tabs 3310A and notches 3310B that allow the electrical contacts portion 3310 to be held securely in the connector support which includes mating features.

The sensor 3300 also includes a bendable portion 3318 that allows the electrical contacts portion 3310 to be arranged parallel to the circuit board of the electronics assembly to facilitate a relatively flat or low profile within the electronics assembly. The bendable portion 3318 also allows the tail portion 3302 to extend down from the electronics assembly so that it can be inserted below the skin of the user while the electrical contacts portion 3310 lays parallel to the circuit board. Lastly, the sensor 3300 includes an armature portion 3320 that allows the sensor 3300 to be held securely to the connector support of the sensor assembly. The armature portion 3320 also provides a leverage point to apply a biasing force to compel the tail portion 3302 into a channel of the sharp as described below in FIG. 35D and the associated text.

Figures 33C, 33D, 33E:
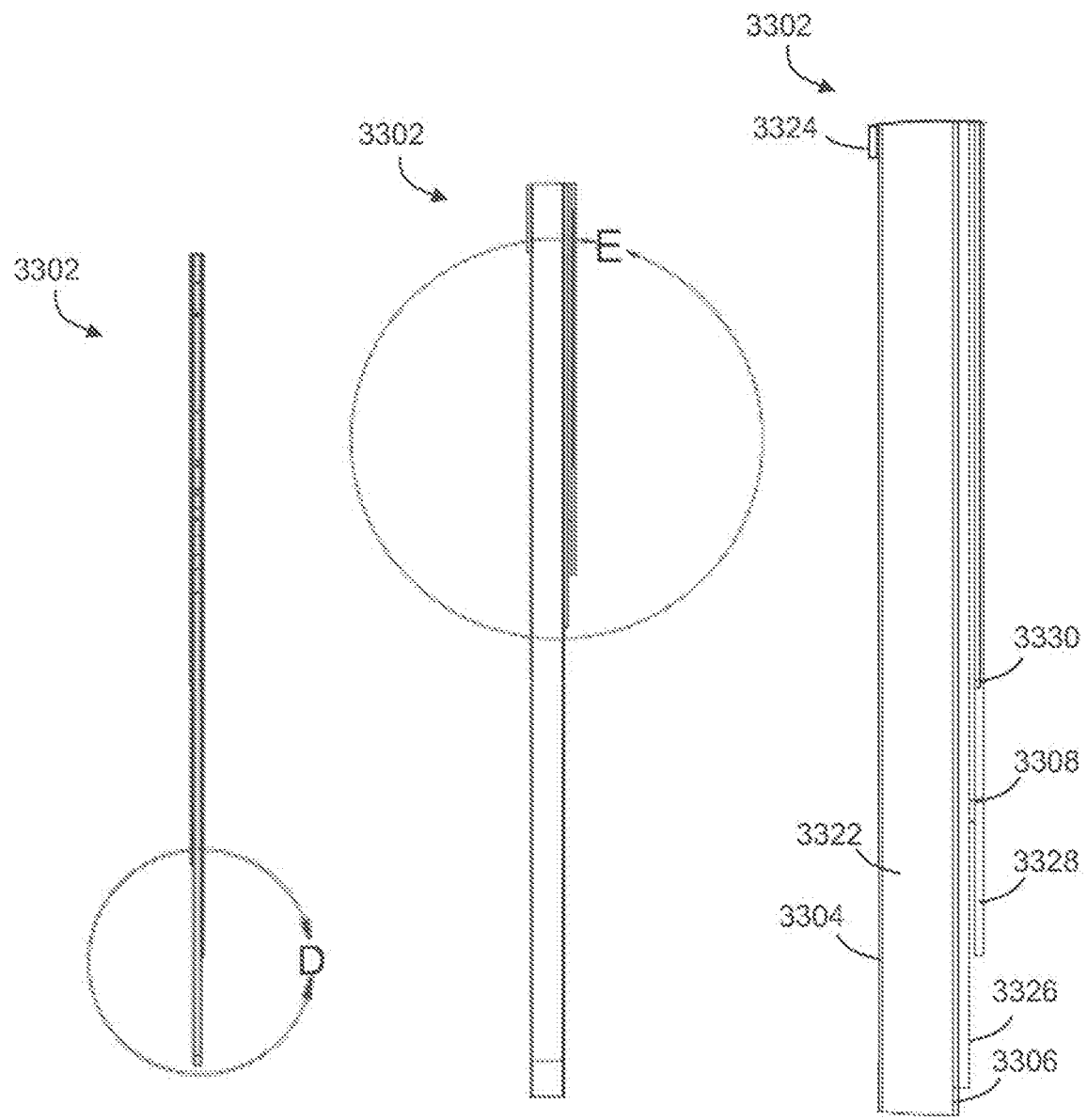

FIG. 33C depicts a side view of the sensor 3300. The encircled portion labeled D is shown in more detail in FIG. 33D. FIG. 33D provides a magnified side view of the distal most part of the tail portion 3302 of the sensor 3300. The encircled portion labeled E is shown in more detail in FIG. 33E. FIG. 33E provides an even further magnified view of the electrodes 3304, 3306, 3308 of the tail portion 3302. As can be seen in FIG. 33E, the electrodes 3304, 3306, 3308 are formed as layers on a substrate 3322. The substrate 3322 is made of a flexible, non-conductive dielectric material. In some embodiments, a clear, high-gloss, heat stabilized polyester film may be used for the substrate 3322 and conductive carbon ink can be used to create the trace layers used for the electrodes 3304, 3306, 3308. In other embodiments, other materials may be used for the substrate 3322 such as polymeric or plastic materials and ceramic materials and for the trace layers such as carbon or gold.

Dielectric layers 3324, 3326, 3328 are disposed between and upon the electrodes 3304, 3306, 3308 to insulate the electrodes 3304, 3306, 3308 from each other. In some embodiments, an ultraviolet (UV) light curable dielectric material may be used for the dielectric layers 3324, 3326, 3328. In other embodiments, other practicable materials may be used. In the particular example embodiment shown, electrode 3304 is a counter electrode, electrode 3306 is a working electrode, and electrode 3308 is a reference electrode. Note that reference electrode 3308 also includes a secondary conductive layer 3330, e.g., an Ag/AgCl layer. In certain embodiments, the lateral surface of the secondary conducive layer 3330 is covered by a dielectric layer 3328 resulting in only the side edges the secondary conductive layer 3330, which extend along the side edges of the substrate 3322, being uncovered by dielectric layer 3328 and, as such, are exposed to the environment when in operative use. In such embodiments, dielectric layer 3328 covers the entire lateral surface of the secondary conducive layer 3330, i.e., 100% of the lateral surface of the secondary conducive layer 3330 is covered by dielectric layer 3328. As such, dielectric layer 3328 has at least the same lateral width and at least the same length as conductive layer 3330.

Further details of the arrangement, dimensions, chemistry, and manufacturing methods of the sensor 3300 may be found in U.S. patent application Ser. No. 13/526,136, entitled "Connectors For Making Connections Between Analyte Sensors And Other Devices," which was filed Jun. 18, 2012, and which is incorporated by reference herein in its entirety and for all purposes.

FIG. 33F depicts a view of the sensor 3300 of FIGS. 33A and 33B including hidden lines representing different layers of electrically conductive trace lines 3332, 3334, 3336 connecting the electrical contacts 3312, 3314, 3316 to the electrodes 3304, 3306, 3308. The electrical contacts 3314, 3316 for the electrodes on the opposite side of the sensor 3300 are coupled to the respective conductive traces 3334, 3336 using vias 3338, 3340 (only two labeled). FIG. 33G is a cross-sectional view of the sensor 3300 taken along line GG of FIG. 33F. As can be seen, conductive trace 3332 covered by dielectric layer 3324 is on one side of the substrate 3322 while conductive traces 3334, 3336 separated by dielectric layer 3326 and covered by dielectric layer 3328 is on the opposite side on the substrate 3322. The electrical contacts 3314, 3316 are accessible via openings in the dielectric layer 3328.

Figure 33H:
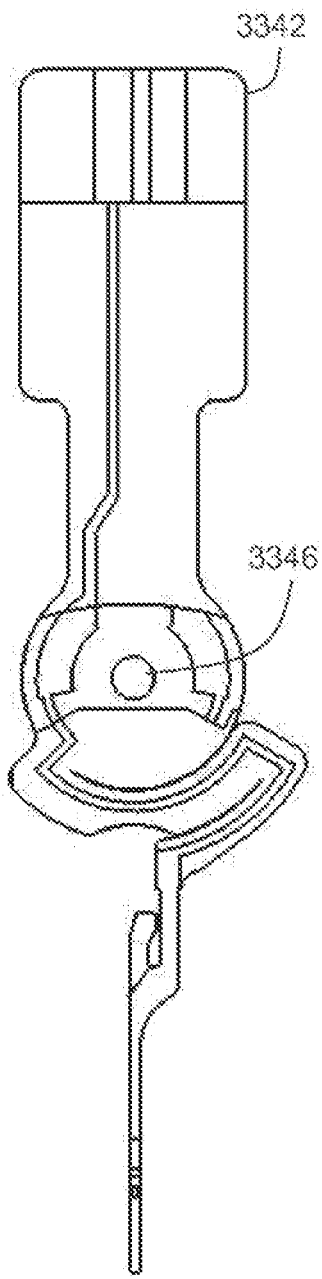
FIGS. 33H-33J are plane views of various sensor designs.
Figure 33I:
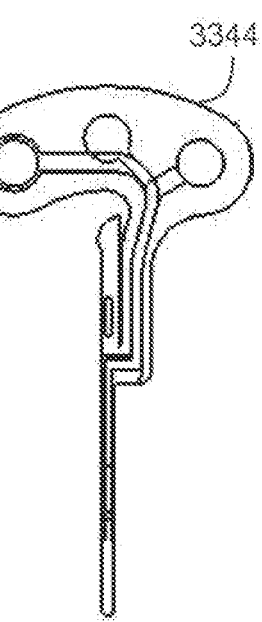
Figure 33J:
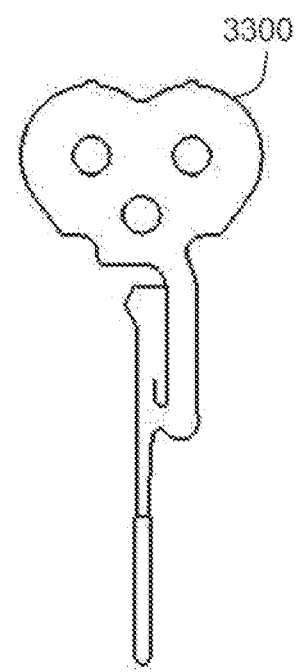

FIGS. 33H to 33J depict three alternative sensor designs 3342, 3344, 3300 side by side for comparison. Notably sensor 3342 includes an aperture 3346 to receive a rivet or other fastener for physical attachment to the PCB of the electronics assembly. Details of sensor 3342 are provided in previously incorporated U.S. patent application Ser. No. 13/526,136, entitled "Connectors For Making Connections Between Analyte Sensors And Other Devices," which was filed Jun. 18, 2012. Sensors 3344 and 3300 are suitable for use with the alternative connector arrangements described below with respect to FIGS. 34A-35D.

Figure 34A:
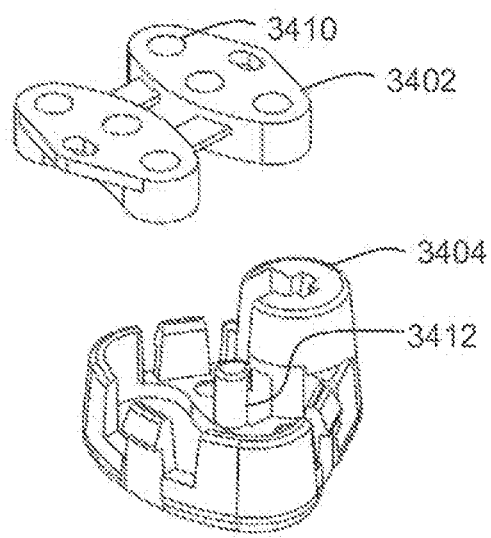
FIGS. 34A-34D are perspective views illustrating combination electrical connector and sensor isolator in yet another advantageous sensor arrangement.
Figure 34B:
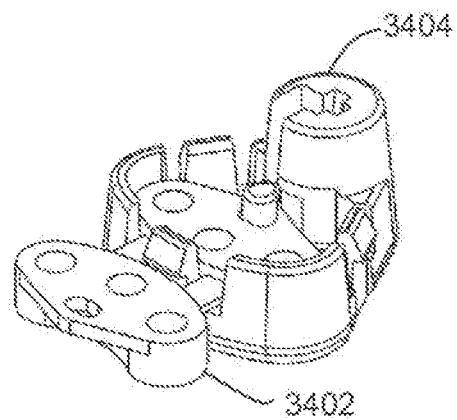
Figure 34C:
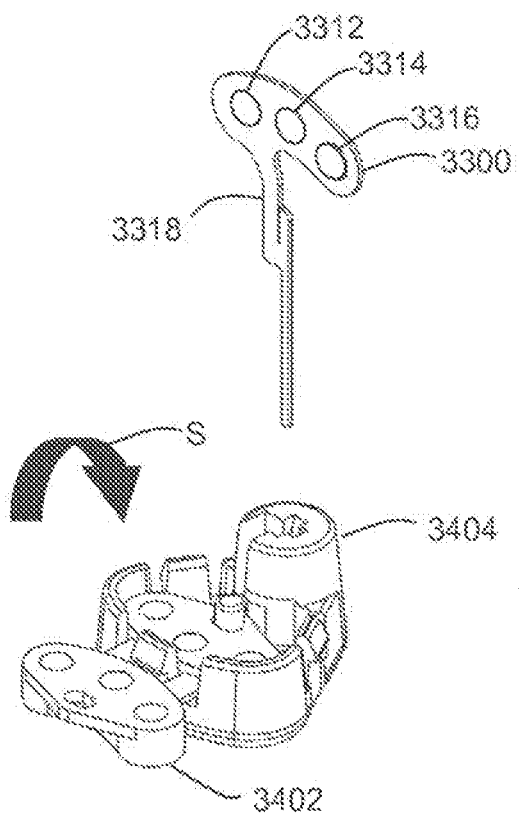

Turning now to FIGS. 34A-35D, an alternative connector arrangement for connecting a circuit board to a sensor 3300 such as depicted in FIGS. 33A, 33B, and 33J is described. As shown in FIG. 34A, a flexible one-piece seal or connector 3402 is molded in silicone or other practicable elastic material. Separate doped silicone conductive elements are set therein which provide electrical contacts 3410 for connection to a circuit board. In some embodiments, the conductive elements can alternatively be over molded or insert-molded into place. The result is a generally malleable/flexible hybrid connection and sealing unit or connector 3402 incorporating a living hinge joining two (as-shown) symmetrical sections. Alternatively, a two-piece design is possible. Yet, with the unitary design, the arrangement can be neatly secured using a single catch boss or post 3412 opposite the hinged section. In some embodiments, two or more posts can be used to secure the connector 3402 folded around and sealing both sides of the contacts portion of the sensor 3300. Thus, even if a dielectric coating on the sensor 3300 fails (e.g., pinhole leaks), the connector 3402 insures that the sensor contacts 3312, 3314, 3316 are protected from moisture or any contaminants. The one-piece design also facilitates assembly as illustrated, in which the flexible connector 3402 is set in a rigid or semi-rigid housing or connector support 3404 with one side located on the post 3412. Then a sensor 3300 is inserted, and bent approximately ninety degrees at the bendable portion 3318 of the sensor 3300. Once bent, the sensor 3300 is then captured with the upper part of the connector 3402 by folding over the connector 3402 as indicated by arrow S in FIG. 34C. The connector 3402 is illustrated as bilaterally symmetrical, however, the connector 3402 can be formed in a direction-specific orientation because in some embodiments, certain of the electrical contacts 3410 may not be necessary. In some embodiments, all the sensor's electrical contacts 3312, 3314, 3316 can be provided on a single side of the sensor 3300 or, in other embodiments, both sides of the sensor 3300.

Figure 34D:
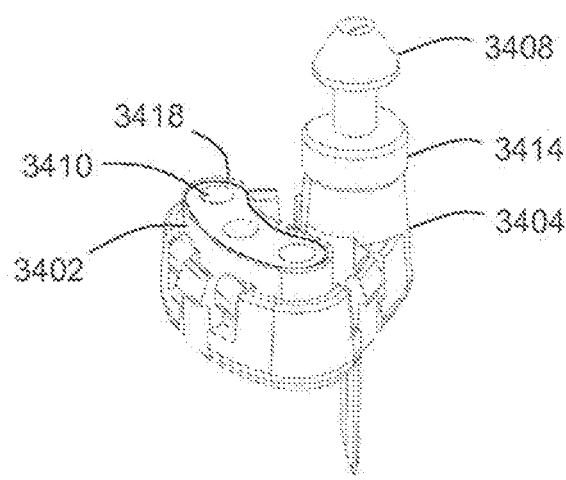

As shown in FIG. 34D, in some embodiments, the top surface of the connector 3402 includes a raised lip 3418 disposed at the top surface edge of the connector 3402 that encircles the electrical contacts 3410 of the connector 3402. The raised lip 3418 can be integrally formed in the elastomeric material that forms the connector 3402 and is thus compressible when the sensor assembly is inserted into the electronics assembly. Alternatively, the raised lip can be embodied as gasket or O-ring on the top surface of the connector 3402. The raised lip 3418 functions to ensure that a seal is formed around the electrical contacts 3410 of the connector 3402 and the electrical contacts of the PCB before any electrical connectivity between the sensor and the electronics assembly is established. Thus, the raised lip 3418 provides a failsafe against a short by insuring the order of assembly includes creating a seal and then creating electrical connectivity as the sensor assembly is mated with the electronics assembly.

Figure 35C:
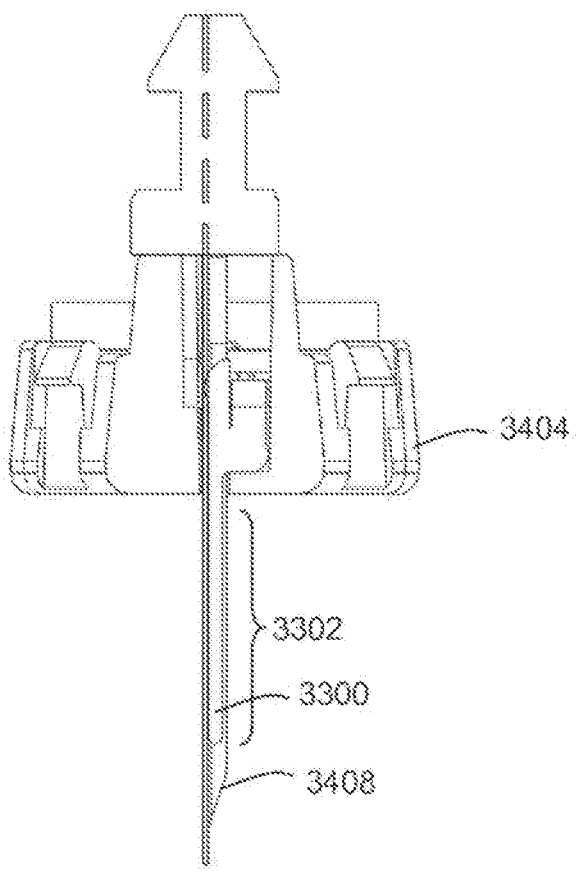
FIG. 35C is an end-section view, with detail view, FIG. 35D, illustrating additional sensor features.
Figure 35D:
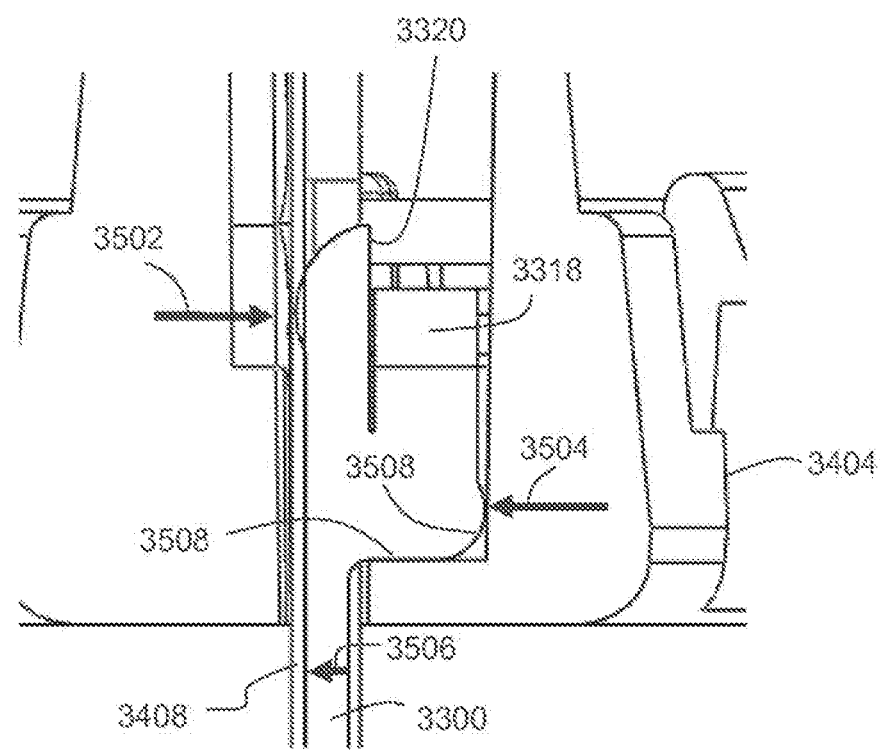
FIGS. 35A and 35B are side assembly and section views, respectively, of the system shown in FIGS. 34A-34D.

In any case, with the sensor 3300 captured within the seal 3402, a sharp 3408 is then introduced, with its hub 3414 contacting the connector support 3404 as shown in FIG. 34D. FIG. 35A illustrates the orientation of the sharp 3408 prior to the insertion of the sharp 3408 into the connector support 3404. FIGS. 35B and 35C provide a cross-sectional overview of the relationship of the sharp 3408 to the sensor 3300. Notably, once inserted in the connector support 3404, the sharp 3408 surrounds and supports the tail portion 3302 of the sensor 3300. In FIG. 35D, further details of the sensor configuration are visible. Particularly, biasing features are shown that abut surfaces of the connector support 3404 in order to center and bias the sensor 3300 into the channel of the sharp 3408. Specifically, armature portion 3320 abuts the surface at arrow 3502 of the connector support 3404 which causes the biasing feature 3508 to act as a fulcrum at arrow 3504 to push the tail portion 3302 of the sensor 3300 into the sharp 3408 at arrow 3506.

In some embodiments, the curved section 3508 of the sensor 3300 can overlie a corresponding surface of the connector support 3404 to help limit the insertion depth (i.e., provide a depth stop) for the sensor 3300. Sensor 3300 vertical placement, including insertion depth, is also controlled based on the relationship between the seal 3402 halves. As noted with respect to the other sensor assembly housings/supports discussed herein, the sensor assembly of FIG. 35C can also include various clip or snap features for its precise associations with a socket in the electronics assembly within the on-body device.

A related arrangement to that described in connection with FIGS. 34A-34D and 35A-35D is presented in FIGS. 36 to 38. In FIG. 36, a sensor 3300 with all electrical contacts on the same side is shown with a sharp 3602 for insertion in a connector support 3604. The connector support 3604 includes an elastomeric (e.g., silicone) seal backing. Once such a sensor assembly set is in a container (or alternatively in an applicator), the sensor assembly can be coupled to the sensor electronics to form an on-body device 222. As shown in FIG. 37, the sensor assembly 3702 is shaped to fit within a socket 3704 that includes a second elastomeric unit with electrical contacts in the elastomer body of the socket 3704. Note that in FIG. 37, the enclosure of the electronics assembly is not shown so that the socket can be more clearly displayed. The socket 3704 is affixed to a circuit board 3706 via any practicable method. The socket 3704 and/or the connector support 3604 can include various coupling features (e.g., a snap fit lip and hook arrangement) to ensure that the electrical contacts are pressed tightly together and sealed within the socket 3704 and sensor assembly 3702. Once the sensor assembly 3702 is received within the socket 3704, the on-body device (e.g., with the complete over-mold enclosure around the circuit board 3706 and adhesive patch 3802 as shown in FIG. 38) is ready for use.

Figure 39A:
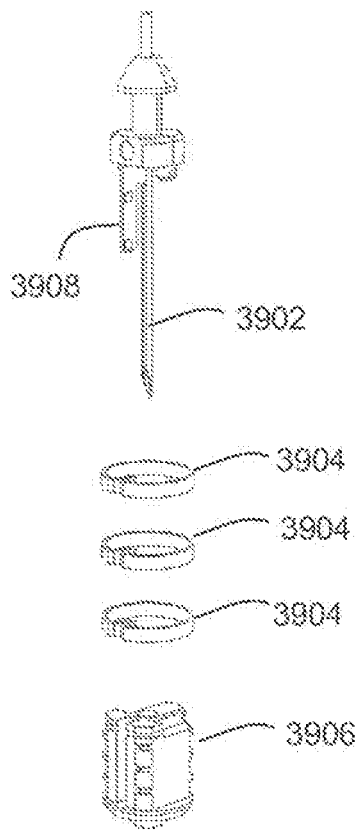
FIGS. 39A and 39B are perspective assembly and as-assembled views of a stacked non-directional sensor connect arrangement.
Figure 39B:
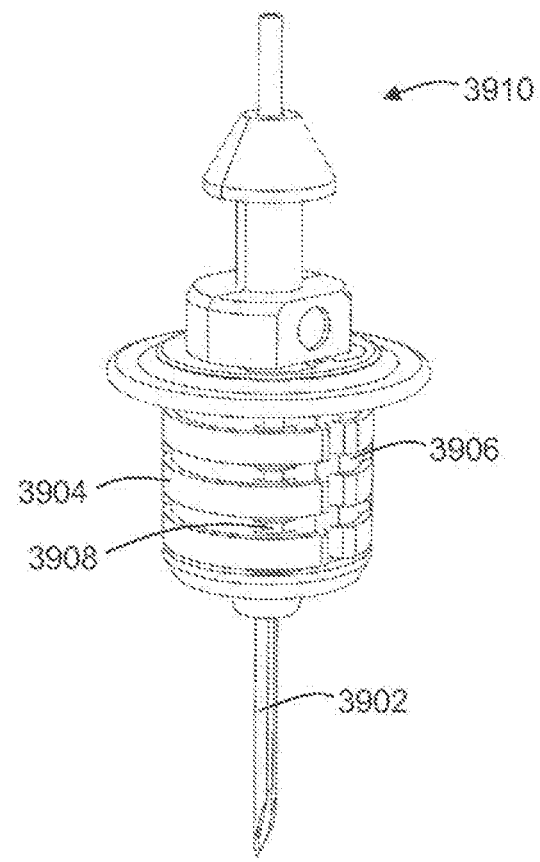
Figure 40:
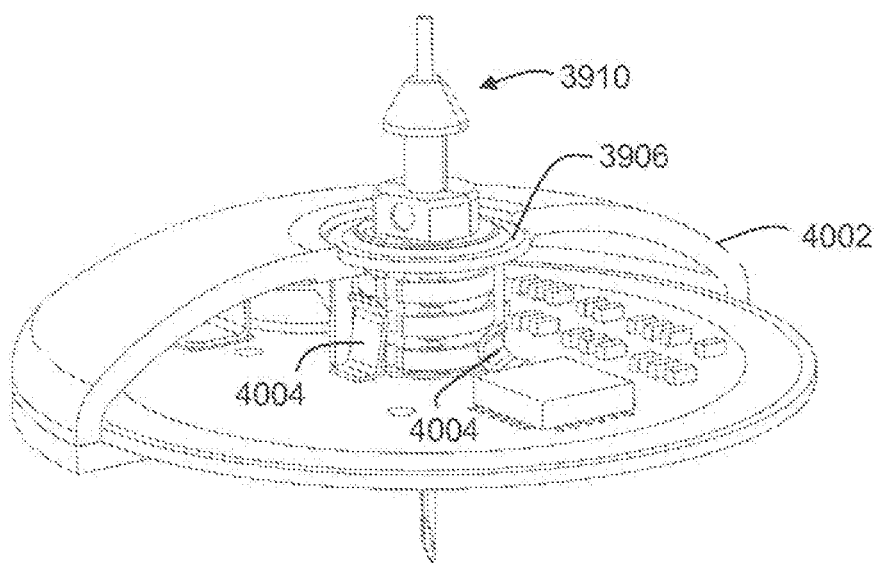
FIG. 40 is a side partial-sectional view of the sensor in FIG. 39 received within an on-body device.

The electrical contacts/connector approaches described above are "directional." In other words, before the sensor assembly is mated with the electronics assembly, the two are aligned relative to each other both longitudinally and rotationally. In some embodiments, the coupling arrangement is "non-directional" and the sensor assembly can be mated with the electronics assembly without aligning the two rotationally. For example, the sensor assembly construction shown in FIGS. 39A and 39B offers such an approach. Separate conductive (e.g., optionally metal) bands 3904 mounted on a core support 3906 connect to sensor electrical contacts 3908 as shown in FIGS. 39A and 39B. The assembled unit (i.e., the sensor assembly 3910), with sharp 3902 in place, is received in the socket of an electronics assembly 4002 to form an on-body device as illustrated in FIG. 40. In some embodiments, brush-type connectors 4004 on the circuit board in the electronics assembly 4002 reach up to the individual levels of the conductive bands 3904. Such a sensor assembly 3910 can be inserted into the socket of the electronics assembly 4002 in any radial/rotational orientation.

A "reversed" approach is illustrated in the sensor assembly 4100 of FIGS. 41A-41C. Here, the circuit board 4102 includes a socket connector 4104 that has an arrangement of stacked conductive elastomeric O-rings 4106 disposed within the inner diameter of the socket connector 4104. A sensor support 4108 is adapted to hold the electrical contacts 4110 of the sensor 4112 in a corresponding stack facing radially outward. When the sensor support 4108 is inserted into the socket connector 4104, the conductive elastomeric O-rings 4106 align vertically with the electrical contacts of the sensor as shown in FIG. 41B (with the socket connector 4104 not shown so that the conductive elastomeric O-rings 4106 are more clearly visible) and in the cross-sectional view of FIG. 41C. In some embodiments, the electrical contacts 4110 of the sensor 4112 can be formed by rolling up a sensor with contacts all on the same side or using the oppositely directed folding/rolling approach shown in connection with FIG. 40—but oriented vertically. Other approaches may be utilized as well. In any case, the electrical contacts of the sensor subtend less than 360 degrees while the conductive elastomeric O-rings on the circuit board provide a multi-level encircling relationship. As with the approach associated with FIGS. 39A to 40, such a sensor assembly 4100 can be inserted into the socket connector 4104 of the electronics assembly 4102 in any radial/rotational orientation.

The sensor connections associated with the circuit board 4404 in the embodiment shown in FIGS. 42 to 44 are arranged in concentric rings. The sensor 4202 includes electrical contacts 4204 held within housing member 4206 and base 4208. The electrical contacts 4204 include "microspring" wireform connectors. These springs provide compliance as well as a discrete top loop. Each electrical contact 4204 is disposed at a different radial distance from the center corresponding to a different concentric conductive track 4304 on a circuit board coupling 4302. Thus, no matter the rotational orientation of the sensor assembly 4200 relative to the circuit board coupling 4302, the electrical contacts 4204 of the sensor 4202 align with the correct concentric conductive tracks 4304. Very fine wire can be used for the springs, thus producing an easily miniaturized system.

Figure 45A:
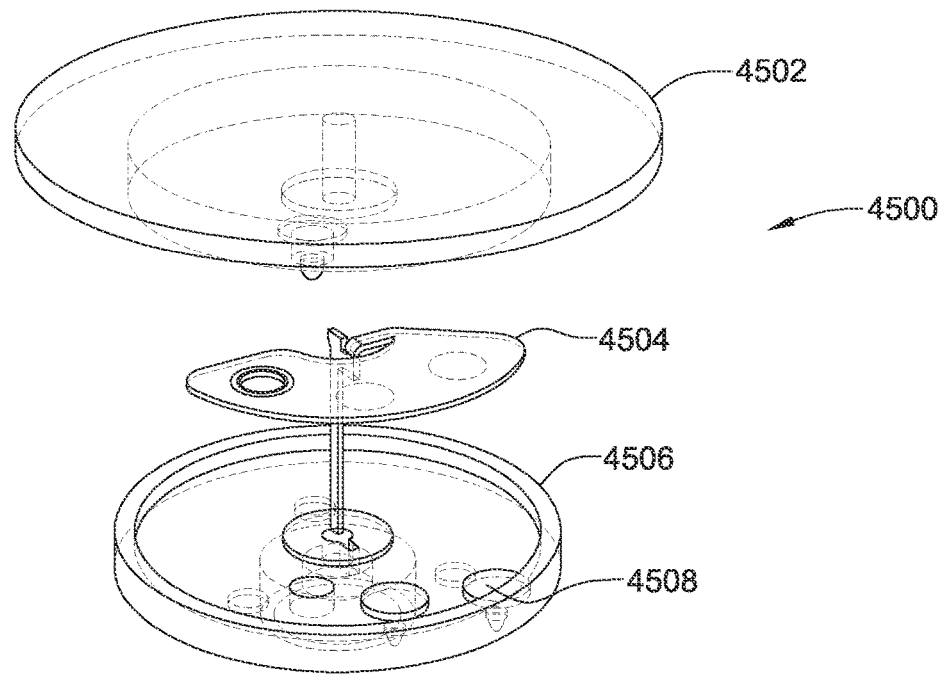
FIGS. 45A and 45B are reversed assembly views of an alternative advantageous sensor connection assembly that can be used like that in FIG. 42.
Figure 45B:
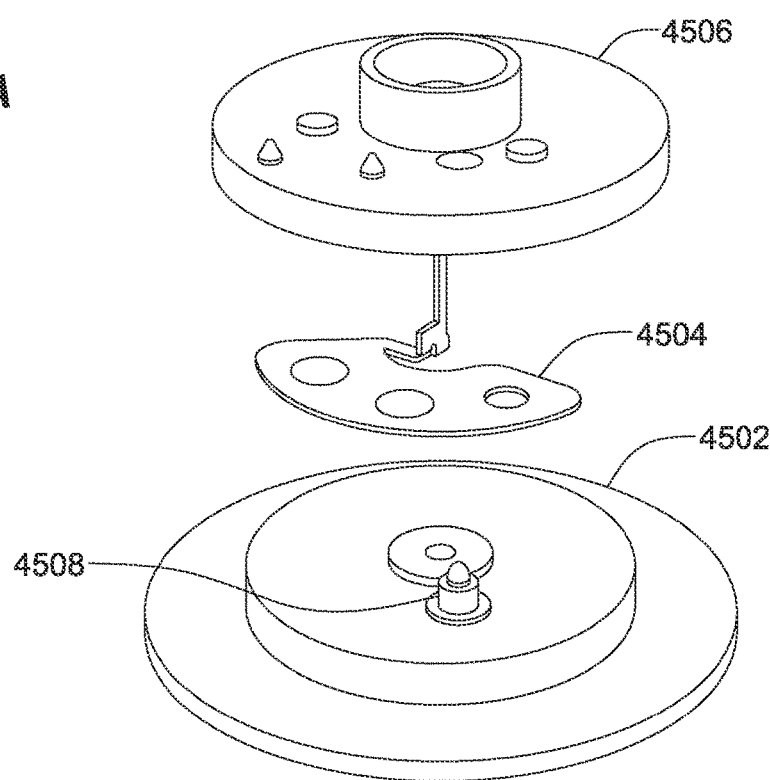
Figure 46A:
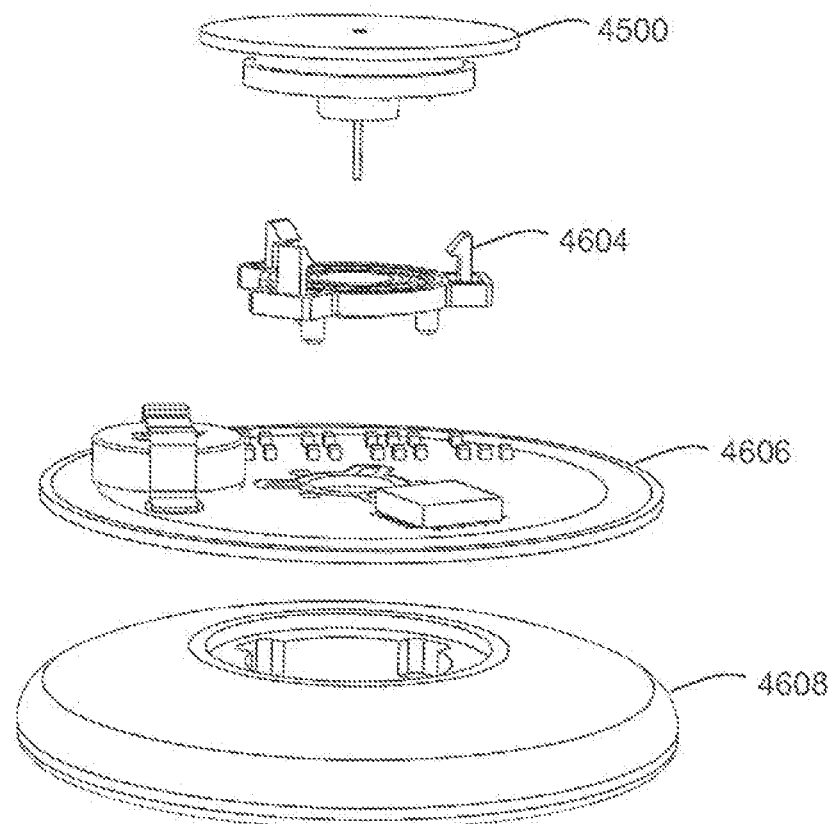
FIGS. 46A and 46B are assembly and sectional views, respectively of a complete on-body device employing the sensor and connection elements illustrated in FIGS. 45A and 45B.
Figure 46B:
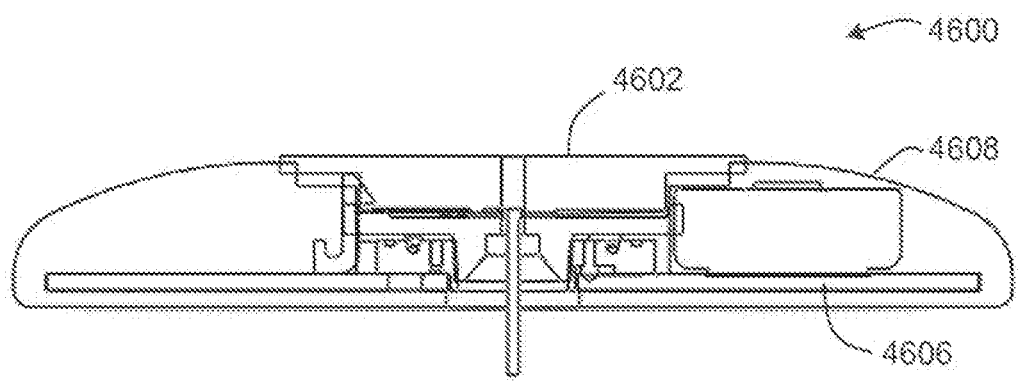

Turning now to FIGS. 45A and 45B, another non-directional sensor assembly connection approach that can be employed with a concentric electronics assembly connection is depicted. As illustrated in the isometric top and bottom views of FIGS. 45A and 45B, a sensor 4504 bent approximately ninety degrees with contacts positioned along different radial paths or arcs, connects with conductive elastomeric contacts 4508 supported by two opposing discs 4502, 4506. Two of the elastomeric contacts 4508 are set on one disc 4506, and a third, configured to pass through a sensor via, is set on the other disc 4502. As shown in FIG. 46A, this sensor assembly 4500 can then be received by a circuit board coupling 4604 which includes concentric tracks for connecting the radially disposed conductive elastomeric contacts 4508 of the sensor assembly 4500 to the circuit board 4606. The enclosure 4608 snap fits or is otherwise adhered to (e.g., using adhesive/welding) a base supporting the circuit board 4606. The as-assembled on-body device 4600 is depicted in FIG. 46B.

Turning now to FIGS. 47A to 47C, an alternative sensor assembly/electronics assembly connection approach is illustrated. As shown, the sensor assembly 4702 includes sensor 4704, connector support 4706, and sharp 4708. Notably, sensor assembly 4702 does not include a separate connector or seal to enclose the sensor's connectors within the connector support 4706 as in the embodiment depicted in FIGS. 34A to 34D (i.e., no seal 3402). Instead, a recess 4710 formed directly in the enclosure of the electronics assembly 4712 includes an elastomeric sealing member 4714 (including conductive material coupled to the circuit board and aligned with the electrical contacts of the sensor 4704). Thus, when the sensor assembly 4702 is snap fit or otherwise adhered to the electronics assembly 4712 by driving the sensor assembly 4702 into the integrally formed recess 4710 in the electronics assembly 4712, the on-body device 4714 depicted in FIG. 47C is formed. This embodiment provides an integrated connector for the sensor assembly 4702 within the electronics assembly 4712.

On-Body Device Construction Details

Figure 48A:
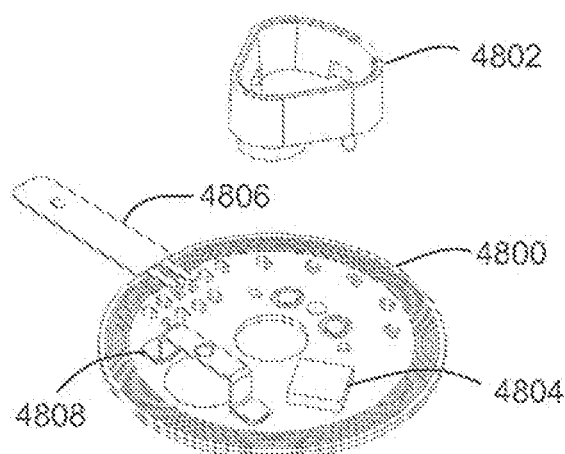
FIGS. 48A-48D are construction views of an on-body subassembly.
Figure 48B:
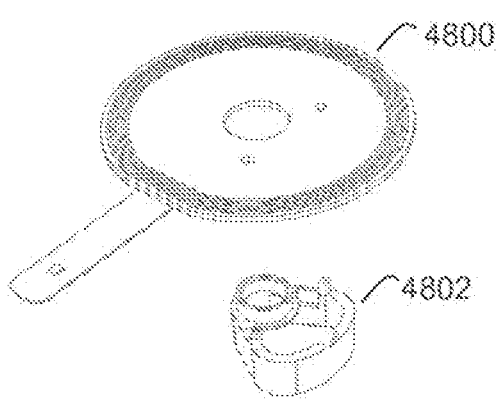
Figure 48C:
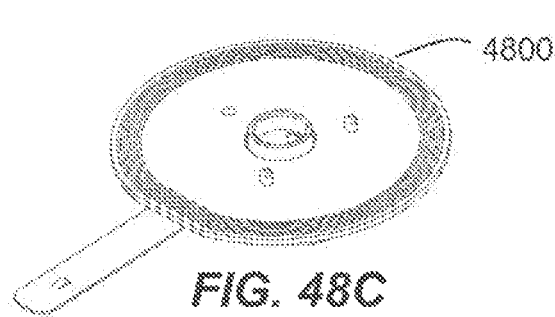
Figure 48D:
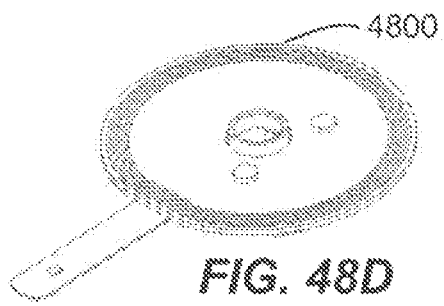
Figure 48E:
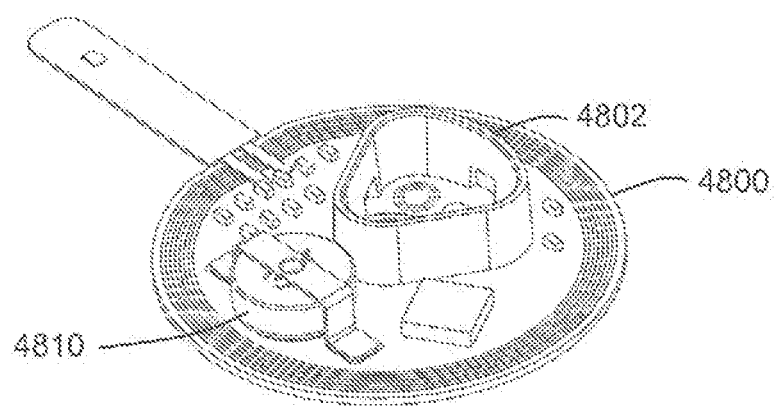
FIG. 48E is a perspective view of a complete on-body electronics subassembly.

Certain elements of the on-body device fabrication may apply to any or all of the above electrical connection configurations. FIGS. 48A-48D provide top (FIG. 48A) and bottom (FIG. 48B-48D) construction views of an exemplary on-body device subassembly. A socket 4802 or mount is fit through vias in a printed circuit board 4800 along with other associated components including a processor 4804 (e.g., an ASIC including a communications facility), thermistor/thermocouple 4806, a battery mount 4808, etc. Once the circuit board 4800 has been populated with these components as shown in FIG. 48C, the socket 4802 is adhered to the circuit board 4800 (e.g., using heat stakes). Once a battery 4810 is set in place, the circuit board 4800 as shown in FIG. 48E is prepared for incorporation into an on-body device.

Figure 49B:
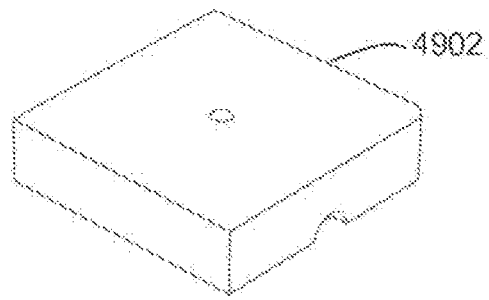
FIGS. 49A-49D illustrate the process of co-molding/ overmolding the assembly in FIG. 48E.
Figure 49B:
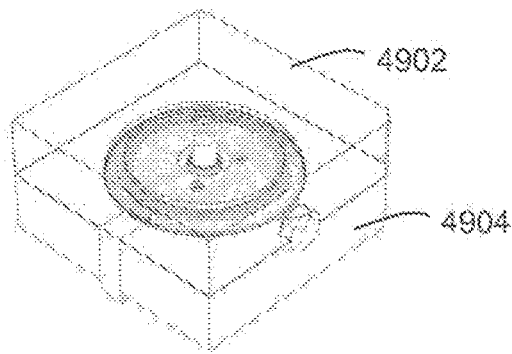
Figure 49A:
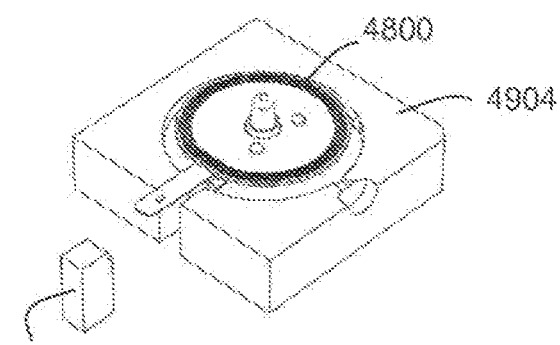
Figure 49C:
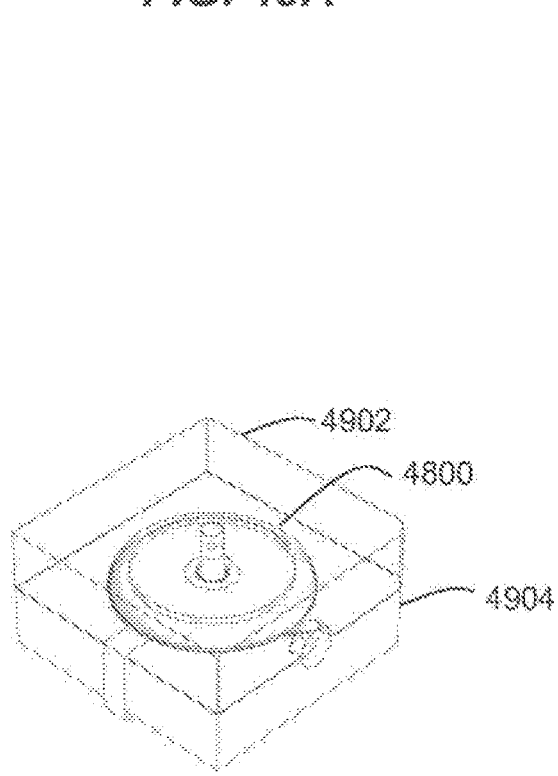
Figure 49D:
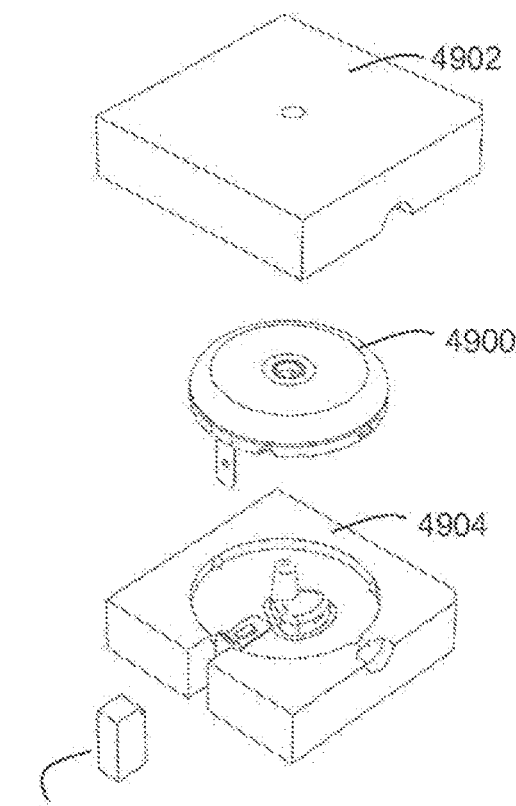

The circuit board 4800 is ready for an over-mold process or other sealing method. As illustrated in FIGS. 49A-49D, the circuit board 4800 is first set in the two-piece mold 4902, 4904. With the mold slide 4906 inserted and mold 4902, 4904 closed as shown in FIG. 49B. As depicted in FIG. 49C, a thermoplastic material is injected into the mold 4902, 4904, encasing the circuit board 4800. The mold 4902, 4904 is opened and the near-final part ejected as shown in FIG. 49D.

Figure 50A:
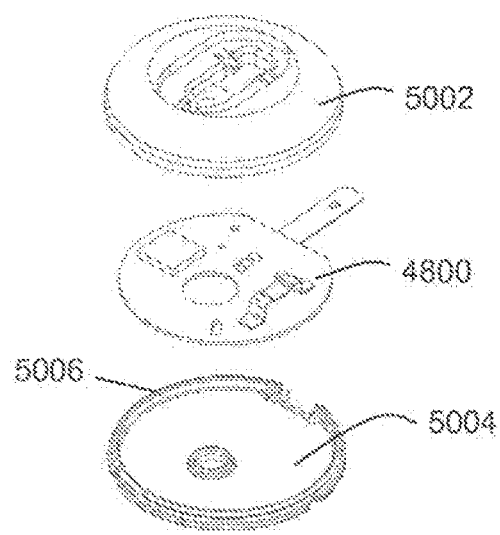
FIGS. 50A-50C are assembly and sectional views of an alternative snap-together approach with the assembly in FIG. 48E.
Figure 50B:
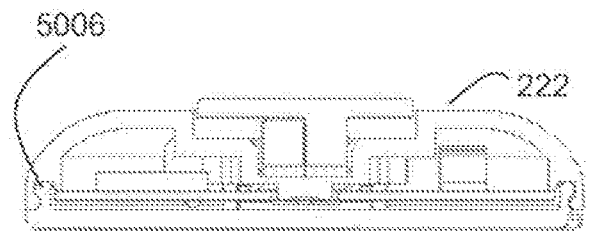
Figure 50C:
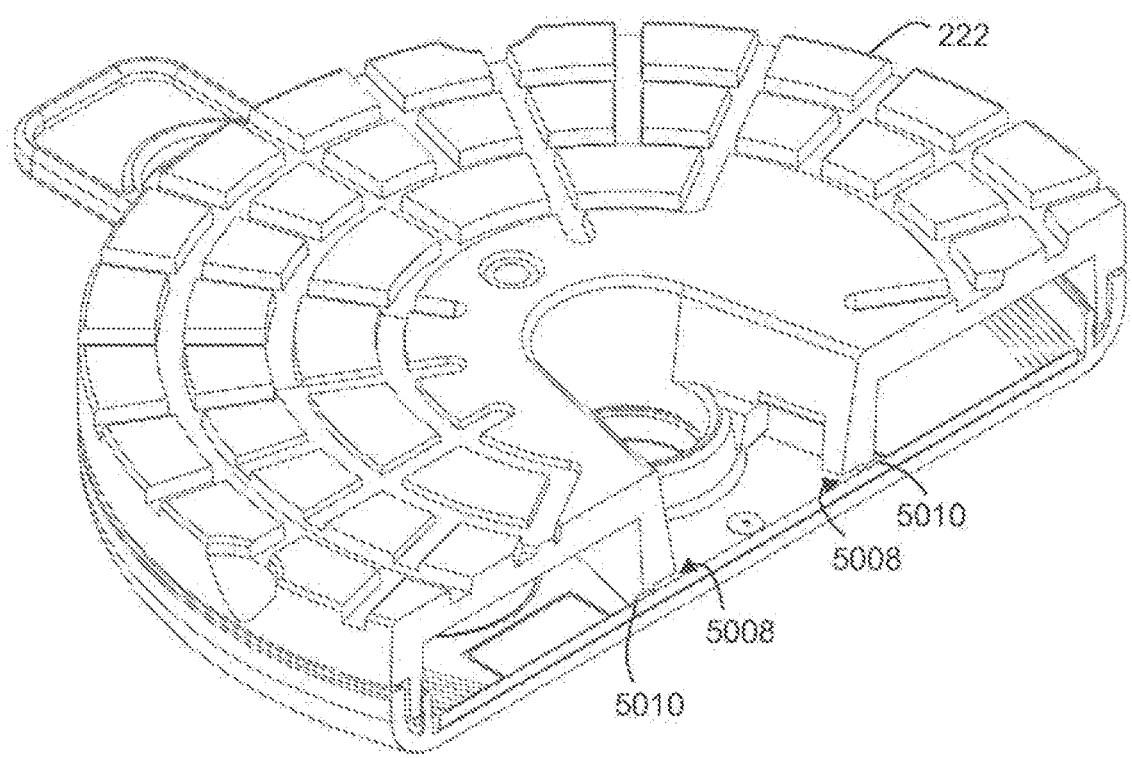

Alternatively, the enclosure of the electronics assembly of the on-body device 222 may include elements snap-fit (or welded/adhered) together as illustrated in the assembly view of FIG. 50A, the as-assembled view of FIG. 50B, and in cross-sectional perspective view of FIG. 50C. An enclosure including a top shell 5002 and a mounting base 5004 can be used to sealably enclose and protect the circuit board 4800. When snap-fit, various interference or snap fit elements (e.g., annular rims 5006) may be provided around the entirety of the periphery of the enclosure or as discrete snap-fit connectors (not shown). Notably, such an approach may benefit from additional O-ring sealing elements to avoid fluid intrusion. Alternatively or additionally, adhesive set at the snap junction(s) may be used to ensure good sealing, especially in connection with continuous annular snap-fit features 5006. As seen in FIG. 50C, a trough 5008 or other features can be provided to insure that adhesive 5010 that may be squeezed out during assembly is not forced into areas that could interfere with operation or assembly of the on-body device 222. In some embodiments, when a top shell 5002 and a mounting base 5004 are fit together with a bead of adhesive 5010 in place as shown, the trough 5008 not only provides space to capture the adhesive 5010 squeezed out but also provides additional surface area for a thicker layer of adhesive 5010 to seal the joint.

Figure 51C:
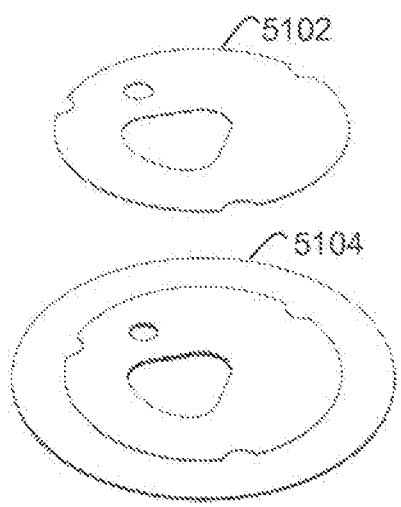
FIGS. 51A-51B are assembly views illustrating adhesive backing application in producing a final on-body device ready for use as shown in perspective-view FIG. 51C.
Figure 51C:
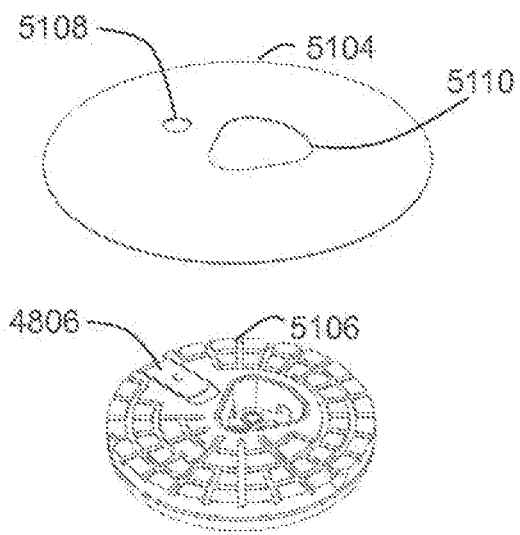
Figure 51C:
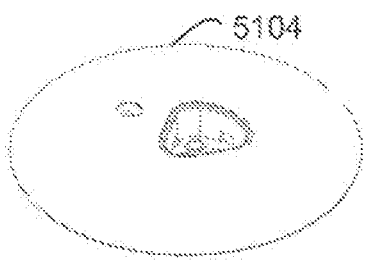

However constructed, final assembly of the electronics assembly of on-body device 222 involves adhesive patch installation. An exemplary approach is illustrated in FIGS. 51A-51C. First, a double-sided adhesive patch 5104 has the inner liner 5102 removed. This exposed adhesive is set over the on-body device body 5106 (with the temperature sensor 4806 folded to seat within a complimentary pocket) and adhered with a first window 5108 aligned for temperature sensing and second window 5110 for sensor assembly receipt. As such, it is ready for placement in an applicator assembly upon removal of the outer release liner, or alternatively ready for placement in a container with or without the outer liner in place, depending on the presence or absence of any liner-puller features provided therein.

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

What is claimed is:

1. A method for assembling an on-body device comprising a glucose sensor assembly, a housing, and sensor electronics,
    wherein the glucose sensor assembly comprises a proximal section comprising a connector support coupled with a proximal portion of a glucose sensor,
    wherein the housing comprises a top portion, a base portion, and a first space defined by the top portion and the base portion, wherein the base portion comprises a recess in a bottom exterior surface, wherein the recess comprises a distal-facing opening, and wherein the recess defines a second space different from the first space,
    the method comprising:
        positioning the sensor electronics within the first space of the on-body device, wherein the sensor electronics comprise a processor, a wireless communications facility, a battery, and a printed circuit board;
        after positioning the sensor electronics within the first space, inserting the connector support through the distal-facing opening of the recess in the bottom exterior surface of the base portion and into the recess, causing the glucose sensor to electrically couple with the sensor electronics.

2. The method of claim 1, wherein positioning the sensor electronics within the first space comprises injecting a thermoplastic material into a mold to form a single integral unit configured to seal the sensor electronics within the first space.

3. The method of claim 2, wherein the mold is a two-piece mold.

4. The method of claim 3, wherein the two-piece mold comprises a first mold piece corresponding with the top portion of the housing and a second mold piece corresponding with the base portion of the housing.

5. The method of claim 1, wherein positioning the sensor electronics within the first space comprises coupling the top portion with the base portion by a snap-fit mechanism such that the sensor electronics are sealed within the first space.

6. The method of claim 1, wherein positioning the sensor electronics within the first space comprises welding the top portion and the base portion together such that the sensor electronics are sealed within the first space.

7. The method of claim 1, wherein positioning the sensor electronics within the first space comprises coupling the top portion with the base portion using an adhesive such that the sensor electronics are sealed within the first space.

8. The method of claim 1, further comprising applying an adhesive patch to the base portion, wherein the adhesive patch comprises a window aligned with the distal-facing opening.

9. The method of claim 1, further comprising causing a first set of mating features of the sensor electronics to couple with a second set of mating features of the glucose sensor assembly when the connector support is inserted into the recess.

10. The method of claim 1, further comprising causing a first set of mating features contained in the recess to couple with a second set of mating features of the glucose sensor assembly when the connector support is inserted into the recess.

11. The method of claim 1, further comprising causing the connector support to come into contact with an elastomeric sealing member when the connector support is disposed in the recess.

12. The method of claim 1, further comprising aligning a polygonal shape of the connector support with a corresponding polygonal cross-sectional area of the distal-facing opening before inserting the connector support through the distal-facing opening.

13. The method of claim 12, wherein the connector support comprises a planar surface.

14. The method of claim 1, wherein the glucose sensor assembly further comprises a distal tail section comprising a distal portion of the glucose sensor configured to be positioned under a skin surface and in contact with a bodily fluid of a subject.

15. The method of claim 14, wherein the distal portion of the glucose sensor of the distal tail section is external to the recess after the connector support is inserted into the recess.

16. The method of claim 14, wherein the glucose sensor assembly further comprises a bent section between the proximal section and the distal tail section, wherein the proximal section and the distal tail section are approximately perpendicular to each other.

17. The method of claim 1, wherein causing the glucose sensor to electrically couple with the sensor electronics comprises causing the connector support to electrically couple with the sensor electronics.

18. The method of claim 17, wherein the connector support is electrically coupled with the sensor electronics via an interface that is external to the first space.

19. The method of claim 18, wherein the interface between the connector support and the sensor electronics is disposed within the recess.

20. The method of claim 1, wherein the housing further comprises a plurality of engagement recesses circumferentially disposed thereon, wherein the plurality of engagement recesses comprises a first engagement recess in a spaced relation to a second engagement recess, and wherein the plurality of engagement recesses is configured to be detachably engaged to an applicator.

21. The method of claim 20, wherein each of the plurality of engagement recesses comprises a concave portion.

22. The method of claim 20, wherein each of the plurality of engagement recesses is disposed on a side wall of the housing.

23. The method of claim 1, wherein the housing further comprises a side wall, wherein the top portion of the housing comprises a top exterior surface, and wherein the side wall is located between the top exterior surface of the top portion of the housing and the bottom exterior surface of the base portion of the housing.

24. The method of claim 23, wherein the side wall comprises a first portion and a second portion, wherein the first portion of the side wall is substantially orthogonal to the bottom exterior surface of the base portion of the housing, and wherein the second portion of the side wall is non-orthogonal to the top exterior surface of the top portion of the housing.

25. The method of claim 1, wherein the top portion of the housing comprises an aperture, and wherein a longitudinal insertion axis extends through the aperture and the recess of the base portion.

26. The method of claim 25, wherein the printed circuit board comprises an aperture, and wherein the longitudinal insertion axis extends through the aperture of the printed circuit board.

27. The method of claim 1, wherein the connector support comprises a planar surface.

\* \* \* \* \*